(12) United States Patent
Kusaka et al.

(10) Patent No.: US 7,795,370 B2
(45) Date of Patent: Sep. 14, 2010

(54) TETRACARBOXYLIC ACID COMPOUND, POLYIMIDE THEREOF, AND PRODUCTION METHOD THEREOF

(75) Inventors: Haruhiko Kusaka, Kanagawa (JP); Yuji Ohgomori, Kanagawa (JP); Masashi Yamanashi, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 114 days.

(21) Appl. No.: 12/093,685

(22) PCT Filed: Nov. 14, 2006

(86) PCT No.: PCT/JP2006/322614

§ 371 (c)(1),
(2), (4) Date: May 14, 2008

(87) PCT Pub. No.: WO2007/058156

PCT Pub. Date: May 24, 2007

(65) Prior Publication Data

US 2009/0182114 A1 Jul. 16, 2009

(30) Foreign Application Priority Data

| Nov. 15, 2005 | (JP) | 2005-330427 |
| Feb. 23, 2006 | (JP) | 2006-046955 |
| Mar. 29, 2006 | (JP) | 2006-091426 |
| Jul. 6, 2006 | (JP) | 2006-186825 |

(51) Int. Cl.
*C08G 73/16* (2006.01)
*C08G 63/12* (2006.01)

(52) U.S. Cl. ............ 528/289; 428/411.1; 428/412; 528/210; 528/211; 528/296; 248/435

(58) Field of Classification Search .......... 428/411.1, 428/412; 528/210, 211, 289, 296; 548/435
See application file for complete search history.

(56) References Cited

FOREIGN PATENT DOCUMENTS

| JP | 1 239525 | 9/1989 |
| JP | 6 51316 | 2/1994 |
| JP | 07-138205 | * 5/1995 |
| JP | 7 138205 | 5/1995 |
| JP | 2002 79634 | 3/2002 |
| JP | 2002 322275 | 11/2002 |
| JP | 2003 96070 | 4/2003 |
| JP | 2003 168800 | 6/2003 |

OTHER PUBLICATIONS

JP 07-138205 May 5, 1995, Norbornanes production by reacting norbornenes with an alcohol carbon, Aoki et al. abstract.*
Jun Sakai, et al., "Preparation and Dielectric properties of siloxane-modified hyperbranched polyimides", 54th Symposium on Macromolecules Polymer Preprints 2 Pc095, vol. 54, No. 2, 2005, p. 4123.
G. Hougham, et al., "Polarization Effects of Fluorine on the Relative Permittivity in Polyimides", Macromolecules, vol. 27, 1994, pp. 5964-5971.
J. L. Hedrick, et al., "High temperature nanofoams derived from rigid and semi-rigid polyimides", Polymer, vol. 36, No. 14, 1995, pp. 2685-2697.

* cited by examiner

*Primary Examiner*—Terressa M Boykin
(74) *Attorney, Agent, or Firm*—Oblon, Spivak, McClelland, Maier & Neustadt, L.L.P.

(57) ABSTRACT

A tetracarboxylic acid compound of formula (1) or (2)

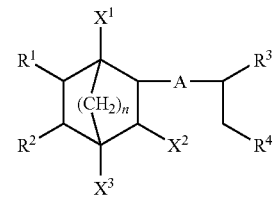

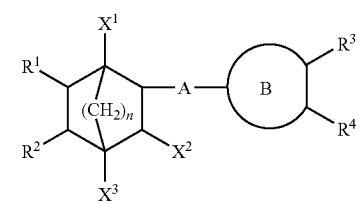

wherein A represents a divalent group; $X^1$, $X^2$ and $X^3$ respectively represent a hydrogen atom or the like; $R^1$, $R^2$, $R^3$ and $R^4$ respectively represent a carboxyl group or an acid anhydride group; n represents 1 or 2; and B represents a cyclic group.

28 Claims, 10 Drawing Sheets

TETRACARBOXYLIC ACID COMPOUND, POLYIMIDE THEREOF, AND PRODUCTION METHOD THEREOF

TECHNICAL FIELD

The present invention relates to a new tetracarboxylic acid compound containing a bicycloalkane structure, e.g., norbornane, that is, a tetracarboxylic acid, a monohydride thereof, or dihydride thereof, and a method for producing the new tetracarboxylic acid compound.

The present invention also relates to a new acid halide serving as an intermediate in the production of the new tetracarboxylic acid compound, a polymer produced by using the new tetracarboxylic acid compound as at least a part of raw material monomers, and a production method thereof.

BACKGROUND ART

Polyimide resins obtained by polymerizing a tetracarboxylic dihydride and a diamine exhibit excellent heat resistance, chemical resistance, mechanical strength, and electric characteristics and, therefore, have been used for various purposes. However, in general, aromatic polyimides have structures including long conjugated systems composed of aromatic rings and imide groups on a consecutive basis and, thereby, the light in a visible region is absorbed, so that the resins are colored with yellow to brown. Consequently, there are limitations on the use for purposes in which achromatic transparency is particularly required, for example, optical material system purposes.

As for resins for optical materials, polymethyl methacrylates and polycarbonates have been used previously. They exhibit excellent transparency, but each exhibits low heat resistance. Therefore, it is difficult to apply them to the purpose of using at high temperatures. Furthermore, polycarbonates exhibit heat resistance slightly higher than the heat resistance of the polymethyl methacrylates, but exhibit high birefringence. Therefore, there is a problem in application to high-precision optical elements.

Polyimide resins have also been used for printed wiring boards, interlayer insulating films, and the like previously. The polyimide resins which have been used for these purposes are aromatic. In typical cases, the dielectric constants of these aromatic polyimides are assumed to be 3.0 to 4.0 (refer to Non-Patent Document 1 as described below).

In recent years, regarding the development of the large scale integrated circuit (LSI), wirings have become finer because of increases in operation speed, and still higher insulating property is required of interlayer insulating films to be used for these purposes. However, known polyimide resins cannot be applied because of high dielectric constants.

Consequently, research has been conducted on reduction in dielectric constant while the heat resistance of the polyimide resin is maintained. One of which is introduction of an atom having a small molar polarizability. Typically, it is a method in which a fluorine atom is introduced (refer to Non-Patent Document 2 as described below). However, industrial production of a polyimide resin containing a fluorine atom has problems in availability of raw materials and cost.

Research has also been conducted on reduction in dielectric constant by forming fine holes in a polyimide resin. However, the formation of such a structure requires a production step of dispersing templates formed from a heat-decomposable material into a polyimide resin homogeneously and thermally decomposing the templates after film formation. Therefore, there is an essential problem in that the production process becomes complicated (refer to Non-Patent Document 3 as described below).

In general, the polyimide resin has a low degree of solubility in a solvent. Consequently, a precursor, in the state of polyamic acid, of the polyimide resin is usually applied as a solution and is converted to the polyimide by a heat treatment at high temperatures. Therefore, there are workability limitations. In particular, there are problems in that, for example, the polyamide cannot be used in the case where a portion, at which the polyimide is intended to be disposed, tends to be irreversibly damaged by heat. Usually, shrinking occurs during cooling after the high temperature treatment and in many cases, serious problems, e.g., peeling and cracking of a film, occur because of a thermal stress originating therefrom.

Under these circumstances, some proposals have been made regarding achromatic, transparent, low-dielectric, solvent-soluble polyimide resins while the heat resistance is maintained. In one of the methods thereof, a polyamide resin is produced by using a tetracarboxylic dihydride not including an aromatic ring, but including an aliphatic group or a diamine. For example, a polyamide resin derived from a tetracarboxylic dihydride having a structure in which alicyclic ring skeletons are condensed on a consecutive basis has been proposed (Patent Document 1 as described below). However, the birefringence of this polyimide resin is not always sufficient. Furthermore, synthesis of the raw material is multistage and complicated and, therefore, industrial production has a problem.

A polyamide resin derived from 1,2,4,5-cyclohexanetetracarboxylic dihydride has been proposed as a substrate material for a thin film transistor (Patent Document 2 as described below). However, according to the examples described therein, the resulting polyimide resin has high transparency, but is colored with light brown. Therefore, it cannot be used for purposes in which high achromatic transparency is required.

In general, introduction of the aliphatic group contributes to improve the transparency and reduce the dielectric property. On the other hand, there are problems in that the heat resistance is reduced and high thermal stability which is a feature intrinsic to the polyimide resin is lost. Furthermore, the imide group itself has high water absorption property, and the water absorption property of general polyimide resins are assumed to be 3 percent by weight or more. This high hygroscopic property is based on the imide group and, therefore, cannot be overcome by merely introducing the aliphatic group.

Patent Document 1: Japanese Unexamined Patent Application Publication No. 2003-96070

Patent Document 2: Japanese Unexamined Patent Application Publication No. 2003-168800

Non-Patent Document 1: 54th (2005) Symposium on Macromolecules Preprints 2Pc095

Non-Patent Document 2: Macromolecules, 27, 5964 (1994).

Non-Patent Document 3: Polymer, 36, 2685 (1995).

DISCLOSURE OF INVENTION

The present invention provides a resin which can exhibit excellent properties, e.g., high transparency, low dielectric property, low water absorption property, low thermal expansion property, solvent solubility, and etching characteristics, while high heat resistance is maintained, and which can be used as a resin for electronic materials, e.g., an electrically insulating film and a flexible printed wiring board, and a resin for optical materials, e.g., a liquid crystal display substrate, an organic electroluminescence (EL) display substrate, an electronic paper substrate, a solar cell substrate, a light-emitting diode sealant, and an optical waveguide. Furthermore, the present invention provides a resin composition containing a polyesterimide or polyamideimide structure, which is a specific example of the above-described resin, a new tetracarboxylic acid compound useful as a raw material monomer for producing the above-described resins and a production method thereof, and a new acid halide useful as a material for producing the tetracarboxylic acid compound.

In order to overcome the above-described known problems, the present inventors conducted intensive research and, as a result, found a tetracarboxylic acid compound represented by the following general formula (1) or (2), and developed a method for producing the tetracarboxylic acid compound simply, as well as a new polymer produced by using them as at least a part of raw material monomers. Consequently, the present invention has been completed.

A resin related to a first aspect of the present invention has a glass transition temperature of 250° C. or higher, a transmittance of light of 400 nm of 70% or more on a film having a film thickness of 30 μm basis, and a water absorption coefficient after the film having a film thickness of 30 μm is immersed in water at 25° C. for 24 hours of 2.0% or less.

A tetracarboxylic acid compound related to a second aspect of the present invention is represented by the following general formula (1) or (2).

[Chemical formula 1]

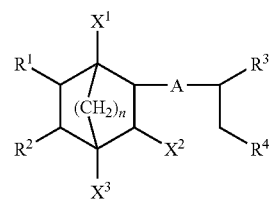

(1)

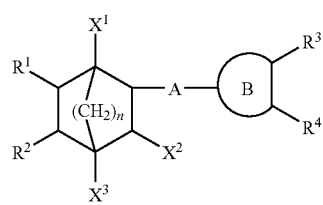

(2)

In the formulae (1) and (2), A represents a divalent group.

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group. However, these groups may further have substituents, and the carbon number of the carbon-containing group is 10 or less.

$R^1$, $R^2$, $R^3$, and $R^4$ represent independently a carboxyl group (—C(O)OH), or $R^1$ and $R^2$ represent an acid anhydride group (—C(O)OC(O)—) formed therefrom and/or $R^3$ and $R^4$ represent an acid anhydride group (—C(O)OC(O)—) formed therefrom.

Subscript n represents an integer of 1 or 2.

In the formula (2), a ring B represents a circular group which is trivalent or more and which may have a substituent.

The compound represented by the above-described general formula (2) may be represented by the following general formula (2A), (2B), or (2C).

[Chemical formula 2]

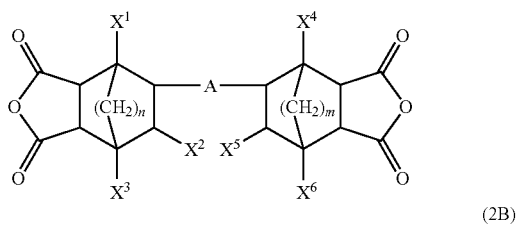

(2A)

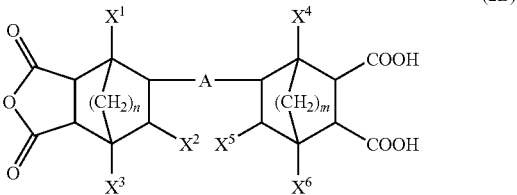

(2B)

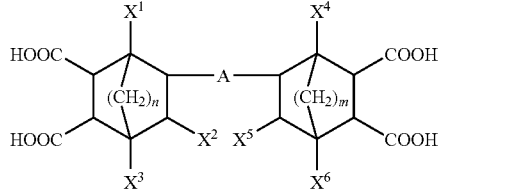

(2C)

In the formulae (2A), (2B), and (2C), each of A, $X^1$, $X^2$, $X^3$, and n represents the same as that in the general formula (2).

$X^4$, $X^5$, and $X^6$ represent independently a hydrogen atom, a halogen atom, a nitrile group, a nitro group, an alkyl group, an alkenyl group, an alkynyl group, an alkoxy group, an amino group, or an amide group. However, these groups may further have substituents, and the carbon number of the carbon-containing group is 10 or less.

Subscript m represents an integer of 1 or 2.

In the above-described general formulae (2A), (2B), and (2C), A may be represented by the following formula (3).

[Chemical formula 3]

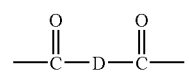

(3)

In the formula (3), D represents a divalent group.

In the above-described general formulae (2A), (2B), and (2C), A may be represented by the following formula (3A) or (3B).

[Chemical formula 4]

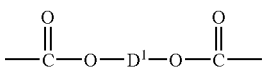

(3A)

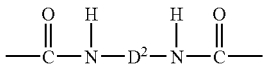

(3B)

In the formulae (3A) and (3B), $D^1$ and $D^2$ represent a divalent group.

In the above-described general formulae (2A), (2B), and (2C), $X^1$, $X^2$, $X^3$, $X^4$, $X^5$, and $X^6$ may represent a hydrogen atom, and A may represent a divalent group including at least one cyclic structure.

An acid halide related to a third aspect of the present invention is represented by the following general formula (4).

[Chemical formula 5]

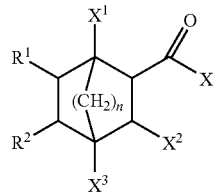

(4)

In the formula (4), $X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group. However, these groups may further have substituents, and the carbon number of the carbon-containing group is 10 or less.

$R^1$ and $R^2$ represent independently a carboxyl group (—C(O)OH) or $R^1$ and $R^2$ represent an acid anhydride group (—C(O)OC(O)—) formed therefrom.

Subscript n represents an integer of 1 or 2.

X represents a chlorine atom or a bromine atom.

According to a fourth aspect of the present invention, a method for producing the tetracarboxylic acid compound related to the second aspect is provided. The method including the step of reacting the acid halide related to the third aspect with a divalent alcohol or amine or a monovalent alcohol or amine, which has a carboxylic anhydride group.

A polymer related to a fifth aspect of the present invention is produced by polymerizing or copolymerizing a raw material monomer containing the tetracarboxylic acid compound related to the second aspect as at least a part thereof.

A polyimide precursor related to a sixth aspect of the present invention includes a structural unit represented by the following general formula (5) as at least a part thereof.

[Chemical formula 6]

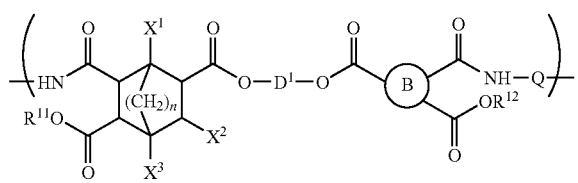

(5)

In the formula (5), $D^1$ represents a divalent group.

A ring B represents a circular group which is trivalent or more and which may have a substituent.

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group.

Q represents a divalent aromatic group or a divalent aliphatic group.

$R^{11}$ and $R^{12}$ represent independently a hydrogen atom or an alkyl group or a silyl group, which has the carbon number of 1 to 10.

Subscript n represents an integer of 1 or 2.

A polyimide precursor related to seventh aspect of the present invention includes a structural unit represented by the following general formula (6) as at least a part thereof.

(6)

[Chemical formula 7]

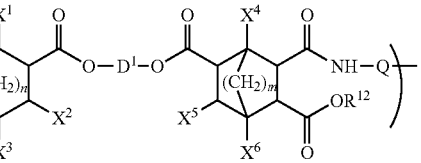

In the formula (6), $D^1$ represents a divalent group. $X^1$, $X^2$, $X^3$, $X^4$, $X^5$, and $X^6$ represent independently a hydrogen atom, a halogen atom, a nitrile group, a nitro group, an alkyl group, an alkenyl group, an alkynyl group, an alkoxy group, an amino group, or an amide group.

Q represents a divalent aromatic group or a divalent aliphatic group.

$R^{11}$ and $R^{12}$ represent independently a hydrogen atom or an alkyl group or a silyl group, which has the carbon number of 1 to 10.

Subscripts n and m represent independently an integer of 1 or 2.

A polyimide related to an eighth aspect of the present invention includes a structural unit represented by the following general formula (7) as at least a part thereof.

(7)

[Chemical formula 8]

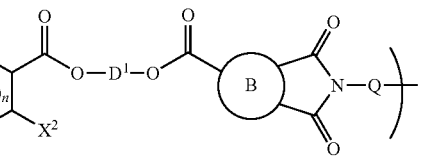

In the formula (7), $D^1$ represents a divalent group.

A ring B represents a circular group which is trivalent or more and which may have a substituent.

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group.

Q represents a divalent aromatic group or a divalent aliphatic group.

Subscript n represents an integer of 1 or 2.

A polyimide related to a ninth aspect of the present invention includes a structural unit represented by the following general formula (8) as at least a part thereof.

(8)

[Chemical formula 9]

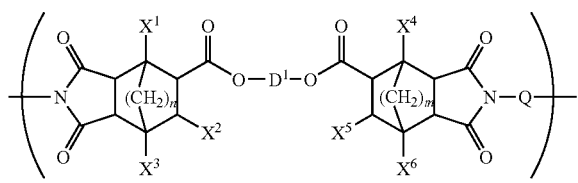

In the formula (8), $D^1$ represents a divalent group.

$X^1$, $X^2$, $X^3$, $X^4$, $X^5$, and $X^6$ represent independently a hydrogen atom, a halogen atom, a nitrile group, a nitro group, an alkyl group, an alkenyl group, an alkynyl group, an alkoxy group, an amino group, or an amide group.

Q represents a divalent aromatic group or a divalent aliphatic group.

Subscripts n and m represent independently an integer of 1 or 2.

According to a method for producing the polyimide related to the tenth aspect, the polyamide related to the eighth or the ninth aspect is produced by reacting the tetracarboxylic acid compound related to the second aspect with diamines and, thereafter, conducting a cyclization and imidization reaction.

According to a method for producing the polyimide related to an eleventh aspect of the present invention, the polyimide related to the eighth or the ninth aspect is produced by subjecting the polyimide precursor related to the sixth or seventh aspect to a cyclization and imidization reaction.

This cyclization and imidization reaction may be conducted by using heating and/or a dehydration reagent.

A film related to a twelfth aspect of the present invention is produced from a resin including a structural unit represented by the following general formula (7) as at least a part thereof.

(7)

[Chemical formula 10]

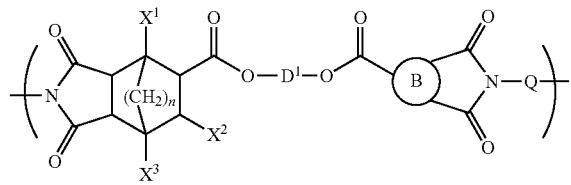

In the formula (7), $D^1$ represents a divalent group.

A ring B represents a circular group which is trivalent or more and which may have a substituent.

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group.

Q represents a divalent aromatic group or a divalent aliphatic group.

Subscript n represents an integer of 1 or 2.

A film related to a thirteenth aspect of the present invention is produced from the resin related to the first aspect.

A liquid crystal component related to a fourteenth aspect of the present invention includes the film related to the twelfth or the thirteenth aspect.

According to the present invention, a raw material monomer for producing a resin can be provided, the resin exhibiting high heat resistance, high transparency, low dielectric property, low water absorption property, organic solvent solubility, and alkali etching characteristics in combination.

That is, the tetracarboxylic acid compound according to the present invention has a structure in which an acid anhydride group has condensed to form a ring on a bicycle[2.2.1]heptane ring (norbornane ring) or a bicycle[2.2.2]octane ring. Therefore, in the case where a resin is produced by using this tetracarboxylic acid compound as a raw material monomer, pi electron conjugation and intramolecular-intermolecular charge transfer interaction in the resulting resin are restricted because of this characteristic fused ring structure, the transparency is enhanced, and the dielectric constant is reduced.

Particularly in the case where a resin is produced by using tetracarboxylic dianhydride, in which two bicycle[2.2.1]heptane rings or bicycle[2.2.2]octane rings with a fused ring of acid anhydride group are bonded with an ester group, as a raw material monomer, the transparency is enhanced, the flexibility is provided to the resin, and the solubility in a solvent is improved significantly while the high heat resistance of a polyimide is maintained.

Furthermore, in the case where a resin produced by polarizing such a compound, if a polymerization functional group having photopolymerizability is introduced, a function of enabling the fine processing, e.g., pattern formation, can be provided.

DETAILED DESCRIPTION

Figure 1:
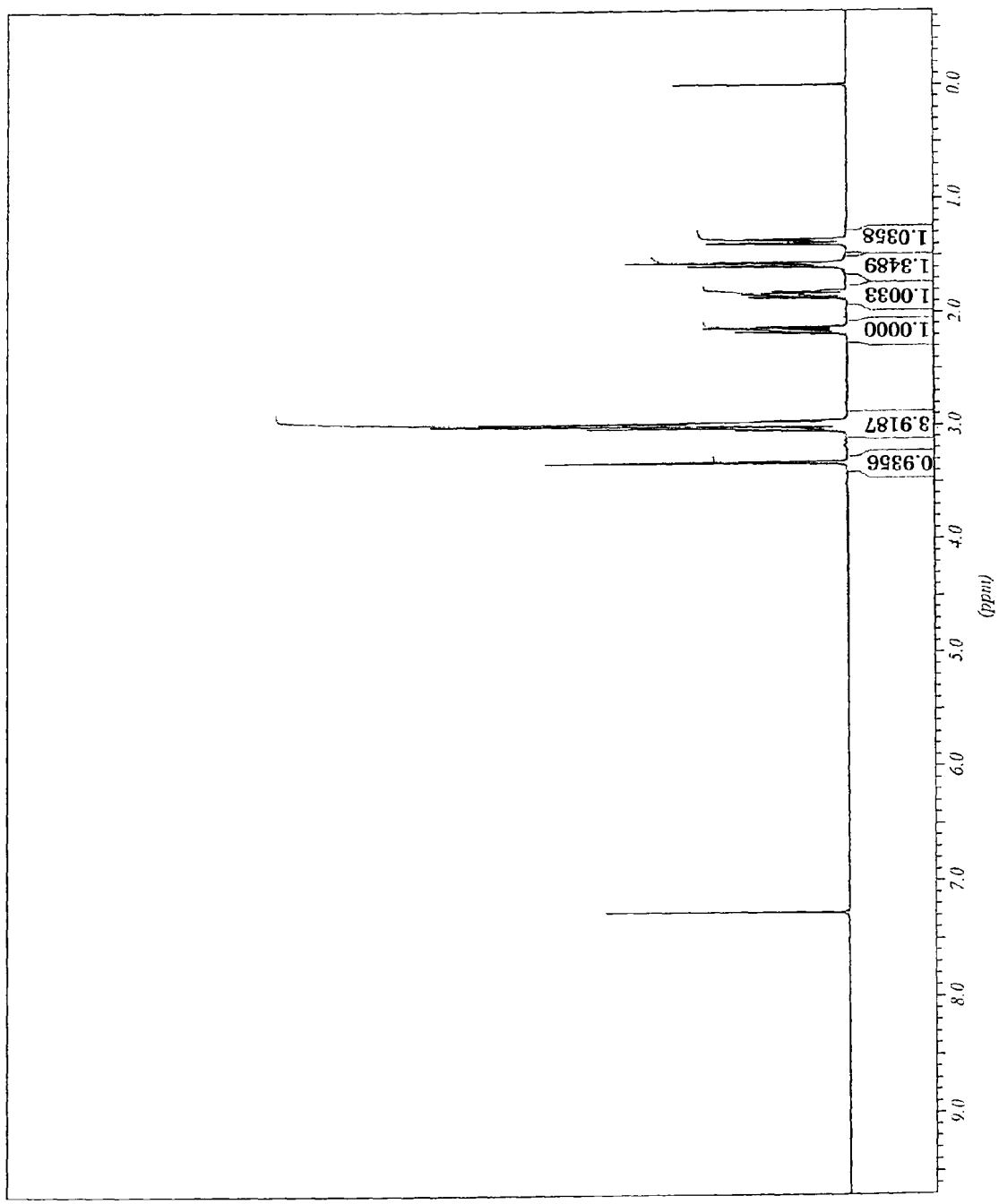
FIG. 1 is a diagram showing a $^1$H-NMR spectrum (CDCl$_3$, MHz) of 5-exo-chloroformyl-norbornane-2-exo,3-exo-dicarboxylic anhydride produced in Example 2.

The embodiments according to the present invention will be described below in detail. However, the explanation of the constituent features described below are one example (typical example) of the embodiment according to the present invention. The present invention is not limited to these contents within the bounds of not departing from the gist thereof and can be variously modified and executed.

[Resin Exhibiting Excellent Properties, e.g., Heat Resistance, Transparency, and Absorption Property in Combination]

The present invention provides a resin exhibiting high heat resistance, high transparency, low dielectric property, low water absorption property, organic solvent solubility, and alkali etching characteristics in combination.

Specifically, the resin satisfies the following conditions.

(1) Glass Transition Temperature

Usually, the glass transition temperature is 200° C. or higher, preferably 230° C. or higher, more preferably 250° C. or higher, and particularly preferably 270° C. or higher.

If this temperature is too low, the heat resistance is reduced. Therefore, the process temperature during working is restricted and some steps may not be adopted.

The glass transition temperature (Tg) can be determined from the change in the amount of tensile elongation at a temperature raising rate of 10° C./min on the basis of the tensile measurement by using Thermomechanical Analyzer (TMA4000) produced by Bruker AXS K.K., as described later in the section of EXAMPLES.

(2) Transmittance of Light of 400 nm on a Film having a Film Thickness of 30 μm Basis Usually, the transmittance is 70% or more, preferably 75% or more, more preferably 80% or more, and particularly preferably 85% or more.

If this transmittance is too low, an application to optical purposes is restricted significantly.

The light transmittance of the light with a wavelength of 400 nm can be measured by using Spectrophotometer for ultraviolet and visible region (UV-3100S) produced by SHIMADZU CORPORATION, as described later in the section of EXAMPLES.

(3) Water Absorption Coefficient After Immersion in Water for 24 Hours

Usually, the water absorption coefficient is 2.0 percent by weight or less, preferably 1.5 percent by weight or less, and particularly preferably 1.0 percent by weight or less. The lower limit is usually 0.01 percent by weight or more, and preferably 0.1 percent by weight or more.

If this absorption coefficient is too high, problems occur in that the electrical conductivity is varied depending on the amount of water in the surroundings, the dimension is changed, and the like. If the absorption coefficient is too low, problems occur in that, for example, water cannot be removed in specific uses.

As described later in the section of EXAMPLES, a film formed having a film thickness of 30 μm is vacuum-dried at 80° C. for 3 hours, the film is immersed in water at 25° C. for 24 hours, the film is pulled up and sandwiched between dry paper (pulp 100%) having good water absorption property, followed by standing for 1 minute, so as to allow the water adhered to the film surface to soak into the paper, the paper is changed two times so as to repeat the same operation, and the weight is measured, so that the water absorption coefficient can be determined from an increment of the weight between before and after the immersion.

Examples of resins exhibiting the above-described characteristics include polycondensed polymer, preferably resins having amide groups or imide groups, more preferably resins having imide groups, and particularly preferably resins having imide groups and ester groups.

[Tetracarboxylic Acid Compound]

The tetracarboxylic acid compound according to the present invention has a structure which is represented by the following general formula (1) or (2) and in which at least one bicycle[2.2.1]heptane ring or bicycle[2.2.2]octane ring is included in the molecule and both terminals are dicarboxylic acids or acid anhydrides thereof.

[Chemical formula 11]

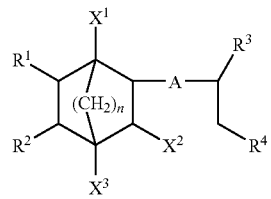
(1)

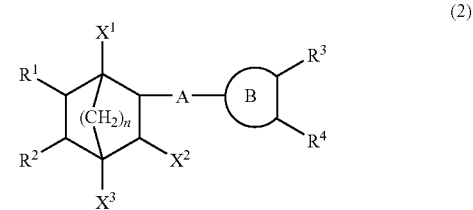
(2)

In the formulae (1) and (2), A represents a divalent group. $X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group. However, these groups may further have substituents, and the carbon number of the carbon-containing group is 10 or less.

$R^1$, $R^2$, $R^3$, and $R^4$ represent independently a carboxyl group (—C(O)OH), or $R^1$ and $R^2$ represent an acid anhydride group (—C(O)OC(O)—) formed therefrom and/or $R^3$ and $R^4$ represent an acid anhydride group (—C(O)OC(O)—) formed therefrom.

Subscript n represents an integer of 1 or 2.

In the formula (2), a ring B represents a circular group which is trivalent or more and which may have a substituent.

The general formula (1) is more specifically represented by the following formula (1a), (1b), or (1c), and the general formula (2) is more specifically represented by the following formula (2a), (2b), or (2c). Hereafter, $X^1$, $X^2$, $X^3$, A, B, and n are the same as those in the general formulae (1) and (2).

[Chemical formula 12]

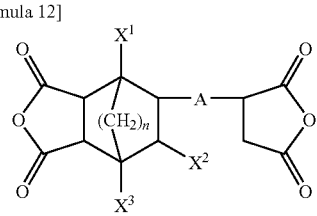
(1a)

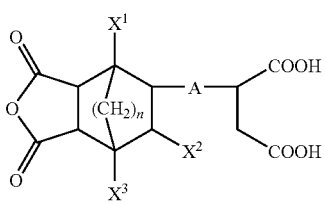
(1b)

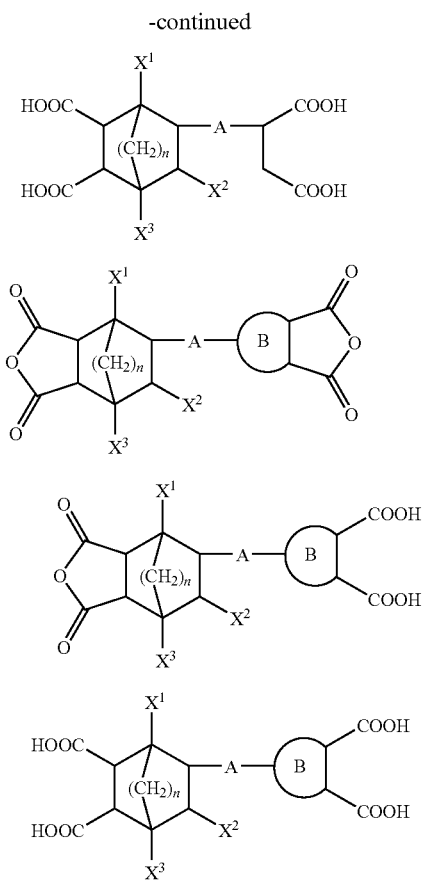

The tetracarboxylic acid compound according to the present invention represented by the above-described general formula (1) or (2) has a characteristic structure in which an acid anhydride and a norbornane ring or a bicycle[2.2.2] octane ring constitute a fused ring and this is bonded to other acid anhydride through a divalent group A. This structure contributes to the resulting polymer exhibiting properties of high transparency, high heat resistance, low absorption property, and high dimension stability in combination. That is, these properties of the tetracarboxylic acid compound according to the present invention tend to be not influenced significantly when the structure of A is any divalent group. Therefore, the structure of A is not specifically limited insofar as it is any divalent group.

In the general formula (1) or (2), A represents a divalent group, and preferably A has the structure represented by the following general formula (3). Here, D may be any divalent group. However, it is more preferable that D has a structure including at least one cyclic structure because the heat resistance of the resin produced by using the tetracarboxylic acid compound according to the present invention as a raw material monomer is improved.

[Chemical formula 13]

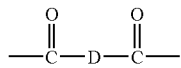

(3)

In the formula (3), D represents a divalent group.

Among the structures represented by the general formula (3), it is preferable that the structure represented by the following general formula (3A) or (3B) is included.

[Chemical formula 14]

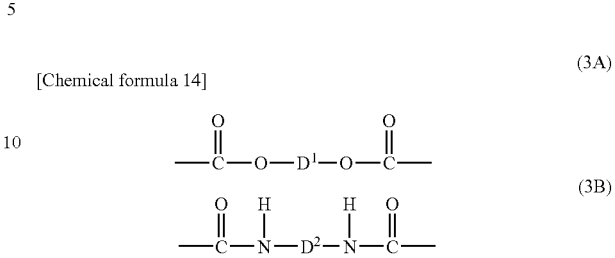

In the formulae (3A) and (3B), $D^1$ and $D^2$ represent a divalent group.

In the general formulae (3A) and (3B), $D^1$ and $D^2$ represent any divalent group.

In the case where D is represented by the general formula (3A) or (3B), the tetracarboxylic acid compound according to the present invention represented by the above-described general formula (1) or (2) has a characteristic structure in which an acid anhydride and a norbornane ring or a bicycle [2.2.2]octane ring constitute a fused ring and this is bonded to another acid anhydride through a group represented by (3A) or (3B). This structure contributes to the resulting polymer exhibiting properties of high transparency, high heat resistance, low absorption property, high dimension stability, and furthermore, high toughness and high solvent solubility in combination. That is, these properties of the tetracarboxylic acid compound according to the present invention tend to be not influenced significantly when the structure of $D^1$ or $D^2$ is any divalent group. Therefore, the structure of $D^1$ or $D^2$ is not specifically limited insofar as it is any divalent group.

However, most of all, it is more preferable that $D^1$ or $D^2$ has a structure including at least one cyclic structure because the heat resistance and the dimension stability of the resin produced by using the tetracarboxylic acid compound according to the present invention as at least a part of raw material monomers is further improved.

As for the above-described divalent cyclic structure, either a structure containing an aromatic ring structure or a structure containing an aliphatic ring structure may be employed. Specific examples of structures containing the divalent aromatic ring structure include groups, e.g., a phenylene group and a naphthylene group, having a structure composed of a single aromatic ring or a fused ring of a plurality of aromatic rings; groups, e.g., a biphenylene group (-Ph-Ph-: Ph represents a phenylene group, the same goes for the following description), having a structure in which a plurality of aromatic rings are bonded directly; and groups, e.g., a diphenyl ether group (-Ph-O-Ph-), a diphenylsulfone group (-Ph-SO$_2$-Ph-), a methanediphenyl group (-Ph-CH$_2$-Ph-), a propane-2,2-diphenyl group (-Ph-C(CH$_3$)$_2$-Ph-), a 9,9-fluorene group, a fluorene-9,9-diphenyl group (-Ph-Fl-Ph-: Fl represents a 9,9-fluorene group), and a 3,3',5,5'-tetramethyl-(1,1'-biphenyl) group, having a structure in which a plurality of aromatic groups are bonded through any divalent bonding group. Any substituent may be included in the aromatic rings of these structures. Furthermore, specific examples of structures containing the divalent aliphatic ring structure include divalent monocyclic alicyclic groups, e.g., a cyclohexylene group, a cyclopentylene group, a cycloheptylene group, and a cyclohexanedimethylene group; cyclic groups, e.g., a tetrahydrofuranyl group and a tetrahydrothiophnyl group, having a heteroatom in a ring; groups, e.g., a cyclohexanedimethyl group (—CH$_2$—Ch-CH$_2$—: Ch represents a cyclohexylene group), having a structure in which bonding is conducted with substituents substituted for groups of an alicyclic; polycyclic alicyclic groups, e.g., a decahydronaphthylene group, a norbornane group, a norbornene group, and an adamantyl group; and groups, e.g., a dicyclohexyl ether group (—Ch-O-Ch-), a methane dicyclohexyl group (—Ch-CH$_2$—Ch-), a propane-2,2-dicyclohexyl group (—Ch-C(CH$_3$)$_2$—Ch-), and a dicyclohexylsulfone group (—Ch-SO$_2$—Ch-), having a structure in which a plurality of alicyclic groups are bonded with any bonding group.

Examples of "any divalent bonding group" for bonding aromatic groups or aliphatic groups in the above-described description include a methylene group (—CH$_2$—), a 2,2-propylene group (—C(CH$_3$)$_2$—), an ether group (—O—), an ester group (—C(O)O—), a keto group (—C(O)—), a sulfonyl group (—SO$_2$—), a sulfinyl group (—SO—), a sulfenyl group (—S—), and 9,9-fluorenylidene, including the groups mentioned as the specific examples.

In the case where the above-described divalent D, D$^1$, and D$^2$ are groups containing a cyclic structure, the position of substitution is not specifically limited. For example, in the case of a phenylene group, substitution at positions 1 and 4 is preferable because the structures of -D-, -D$^1$-, and -D$^2$- become straight and it is expected that the heat resistance increases and the coefficient of linear expansion decreases. On the other hand, substitution at positions 1 and 3 in the phenylene group is preferable because the structure is bent at those positions and it is expected that the solubility in a solvent is improved. Therefore, it is preferable that the positions of substitution are selected appropriately in such a way as to allow D, D$^1$, and D$^2$ to have structures suitable for the required properties.

Among these D, D$^1$, and D$^2$, in the case where the aromatic ring structure is contained, a structure containing at least a phenylene group is more preferable, and in the case where the aliphatic ring structure is contained, a structure containing at least a six-membered ring structure or a five-membered ring structure is more preferable. More specifically, among them, particularly preferable examples include a phenylene group, a biphenylene group, a diphenyl ether group, a diphenylsulfone group, a propane-2,2-diphenyl group, a fluorene-9,9-diphenyl group, a 3,3',5,5'-tetramethyl-(1,1'-biphenyl) group, a cyclohexylene group, a cyclohexanedimethyl group, a propane-2,2-dicyclohexyl group, and a divalent norbornane group because the structure becomes more rigid.

Regarding the structures of D, D$^1$, and D$^2$, as they become relatively large constituents, the density of the imide group of the resulting resin is reduced and, therefore, the water absorption coefficient tends to decrease. Consequently, it is preferable that the D, D$^1$, and D$^2$ having a larger structure are selected for the uses in which a low water absorbing property is required.

In the formula (2), a ring B represents a circular group which is trivalent or more and which may have a substituent. The upper limit of the valence of the circular group of the ring B is not specifically limited, and is usually 20 or less, preferably 10 or less, more preferably 5 or less, and particularly preferably 3.

Specific examples of the cyclic structures of the ring B include aromatic rings, e.g., a benzene ring and a naphthalene ring, and aliphatic rings, e.g., a cyclohexane ring, a cyclopentane ring, a norbornane ring [bicycle[2.2.1]heptane ring), and a bicycle[2.2.2]octane ring. In the case where they have substituents, examples of substituents include specific examples of substituents of X$^4$ to X$^6$ as described later. Most of all, those represented by the following general formula (2A), (2B), or (2C) are preferable.

[Chemical formula 15]

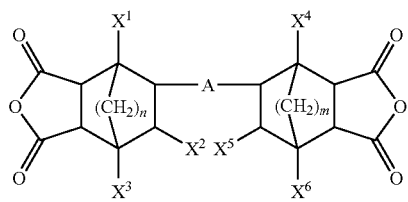

(2A)

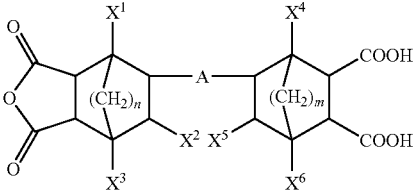

(2B)

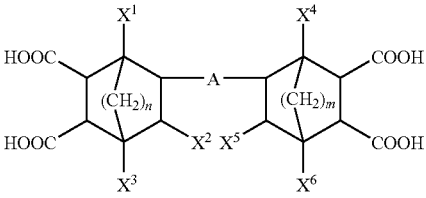

(2C)

In the formulae (2A), (2B), and (2C), each of A, X$^1$, X$^2$, X$^3$, and n represents the same as that in the general formula (2).

X$^4$, X$^5$, and X$^6$ represent independently a hydrogen atom, a halogen atom, a nitrile group, a nitro group, an alkyl group, an alkenyl group, an alkynyl group, an alkoxy group, an amino group, or an amide group. However, these groups may further have substituents, and the carbon number of the carbon-containing group is 10 or less.

Subscript m represents an integer of 1 or 2.

Furthermore, a norbornane ring represented by the above-described general formula (2A), (2B), or (2C), in which a cyclohexane ring is crosslinked with a methylene group and n=m=1, is more preferable because synthesis is relatively easy and the resulting resin exhibits high transparency and improved heat resistance.

As described above, X$^1$, X$^2$, X$^3$, X$^4$, X$^5$, and X$^6$ in the general formulae (1), (2), (2A), (2B), and (2C) represent independently a hydrogen atom, a halogen atom, a nitrile group, a nitro group, an alkyl group, an alkenyl group, an alkynyl group, an alkoxy group, an amino group, or an amide group. However, these groups may have any substituent in the case where substituents can be further included. The carbon number of the carbon-containing group is 10 or less.

Specific examples of alkyl groups of X$^1$ to X$^6$ include a methyl group, an ethyl group, a n-propyl group, an i-propyl group, and n-butyl group.

Specific examples of alkenyl groups include a vinyl group, a propenyl group, and a butenyl group.

Specific examples of alkynyl groups include an ethynyl group, a propynyl group, and a butynyl group.

Specific examples of alkoxy groups include a methoxy group, an ethoxy group, a n-propoxy group, an i-propoxy group, and a n-butoxy group.

Specific examples of halogen atoms include a fluorine atom, a chlorine atom, a bromine atom, and an iodine atom.

Specific examples of nitrile groups include a cyano group, an acetonitrile group, and a propionitrile group.

Specific examples of amide groups include a formamide group and an acetamide group.

In the case where these groups further have substituents, examples of substituents include an alkyl group, an alkenyl group, an alkoxy group, a halogen atom, a nitrile group, and an amide group.

Regarding $X^1$ to $X^6$, most of all, a hydrogen atom and a halogen atom is preferable from the viewpoint of ease of availability of raw materials.

Regarding the structure in which A, $X^1$, $X^2$, $X^3$, $X^4$, $X^5$, $X^6$, n, and m are in preferable combination in the general formulae (2A), (2B), and (2C), A is a group having a circular structure, $X^1$, $X^2$, $X^3$, $X^4$, $X^5$, and $X^6$ are independently composed of a halogen atom or a hydrogen atom, and n=m=1 or n=m=2. In more preferable configuration, A is a group having a circular structure, all $X^1$, $X^2$, $X^3$, $X^4$, $X^5$, and $X^6$ are hydrogen atoms, and n=m=1.

[Acid Halide]

The acid halide according to the present invention is represented by the following general formula (4).

[Chemical formula 16]

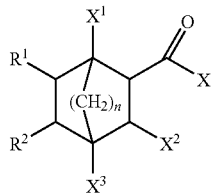

(4)

In the formula (4), $X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group. However, these groups may further have substituents, and the carbon number of the carbon-containing group is 10 or less.

$R^1$ and $R^2$ represent independently a carboxyl group (—C(O)OH) or $R^1$ and $R^2$ represent an acid anhydride group (—C(O)OC(O)—) formed therefrom.

Subscript n represents an integer of 1 or 2.

X represents a chlorine atom or a bromine atom.

In the above-described general formula (4), specific examples and preferable examples of $X^1$ to $X^3$ are the same as those for $X^1$ to $X^3$, respectively, in the above-described general formulae (1) and (2).

[Polymer Produced by Polymerizing or Copolymerizing Raw Material Monomers Containing Tetracarboxylic Acid Compound as at Least a Part Thereof]

Polymers produced by polymerizing or copolymerizing raw material monomers containing the above-described tetracarboxylic acid compound according to the present invention as at least a part thereof include both polyimide precursors produced by polymerizing the raw material monomers and polyimides produced by subjecting the resulting precursors to a dehydration treatment or produced by subjecting the raw material monomers to a dehydration treatment directly.

[Polyimide Precursor, Polyimide]

The polyimide precursor and the polyimide according to the present invention refer to a polyimide precursor represented by the following general formula (5) and a polyimide represented by the following general formula (7).

[Chemical formula 17]

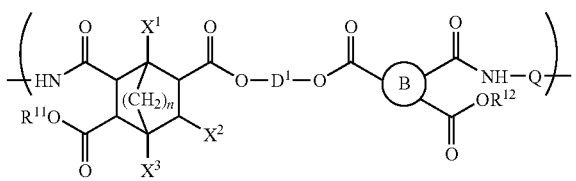

(5)

In the formula (5), $D^1$ represents a divalent group.

A ring B represents a circular group which is trivalent or more and which may have a substituent.

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group.

Q represents a divalent aromatic group or a divalent aliphatic group.

$R^{11}$ and $R^{12}$ represent independently a hydrogen atom or an alkyl group or a silyl group, which has the carbon number of 1 to 10.

Subscript n represents an integer of 1 or 2.

[Chemical formula 10]

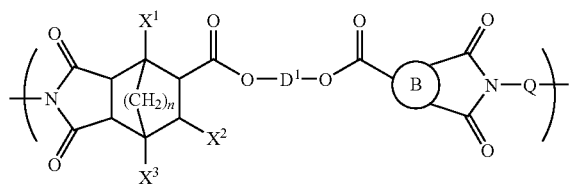

(7)

In the formula (7), $D^1$ represents a divalent group.

A ring B represents a circular group which is trivalent or more and which may have a substituent.

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group.

Q represents a divalent aromatic group or a divalent aliphatic group.

Subscript n represents an integer of 1 or 2.

Preferably, the polyimide precursor represented by the above-described general formula (5) is represented by the following general formula (6). Preferably, the polyimide represented by the above-described general formula (7) is represented by the following general formula (8).

[Chemical formula 19]

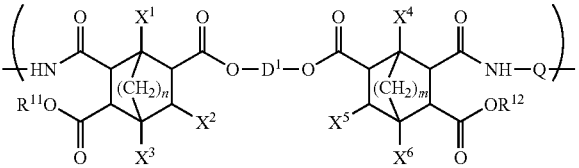

(6)

In the formula (6), $D^1$ represents a divalent group.

$X^1$, $X^2$, $X^3$, $X^4$, $X^5$, and $X^6$ represent independently a hydrogen atom, a halogen atom, a nitrile group, a nitro group, an alkyl group, an alkenyl group, an alkynyl group, an alkoxy group, an amino group, or an amide group.

Q represents a divalent aromatic group or a divalent aliphatic group.

$R^{11}$ and $R^{12}$ represent independently a hydrogen atom or an alkyl group or a silyl group, which has the carbon number of 1 to 10.

Subscripts n and m represent independently an integer of 1 or 2.

(8)

[Chemical formula 20]

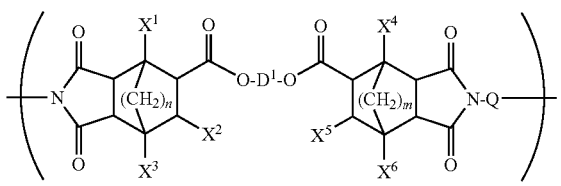

In the formula (8), $D^1$ represents a divalent group.

$X^1$, $X^2$, $X^3$, $X^4$, $X^5$, and $X^6$ represent independently a hydrogen atom, a halogen atom, a nitrile group, a nitro group, an alkyl group, an alkenyl group, an alkynyl group, an alkoxy group, an amino group, or an amide group.

Q represents a divalent aromatic group or a divalent aliphatic group.

Subscripts n and m represent independently an integer of 1 or 2.

In the above-described general formulae (5) to (8), $D^1$, B, n, $X^1$, $X^2$, $X^3$, $X^4$, $X^5$, and $X^6$ are the same as the contents described in the section of Tetracarboxylic acid compound. In general formula (5), the bonding positions of the —CONH— group and the —COOR group bonded to each norbornane ring or bicycle[2.2.2]octane ring may be mutually changed.

$R^{11}$ and $R^{12}$ represent independently a hydrogen atom or an alkyl group or a silyl group, which has the carbon number of 1 to 10.

In the general formulae (5) and (7), Q is any divalent group.

The polyimide (7) represented by the general formula (7) according to the present invention is characterized by having a partial structure in which a norbornane ring or a bicycle [2.2.2]octane ring and an imide group constitute a fused ring, and this is bonded to Q through —C(O)—O-$D^1$-O—C(O)— and B to form a polymer. This partial structure in which a norbornane ring or a bicycle[2.2.2]octane ring and an imide group constitute a fused ring contributes to the resulting polymer exhibiting properties of high transparency, high heat resistance, and high dimension stability in combination. That is, these properties of the present compound tend to be not influenced significantly when the structure of Q is any divalent group. Therefore, the structure of Q is not specifically limited insofar as it is any divalent group.

Among these divalent groups, groups having a cyclic structure are preferable as the structure of Q. The structure having a cyclic structure refers to a structure in which Q includes an aromatic group and a structure in which Q includes an aliphatic structure. If Q includes a cyclic structure, the heat resistance and the dimension stability of the resulting polyimide resin are improved. In the case where the aliphatic structure is included, it is also possible to obtain such a feature that absorption of light in the ultraviolet region can be reduced while the heat resistance is maintained.

Regarding specific structures, examples of aromatic groups of Q include a phenylene group, a naphthylene group, a biphenylene group, a diphenyl ether group, a diphenylsulfone group, a 4,4'-(9,9-fluorenylidene)diphenyl group, a methylenediphenyl group, an isopropylidenediphenyl group, a 3,3'-dimethyl-1,1'-biphenyl group, a 3,3',5,5'-tetramethyl-1,1'-biphenyl group, and 2,2'-bis(trifluoromethyl)-1,1'-biphenyl group. Examples of aliphatic structure groups include a cyclohexylene group, a cyclohexanedimethylene group, a dicyclohexyl ether group, a methylenedicyclohexyl group, and a decahydronaphthylene group. In the structure, these groups may be mutually bonded or these groups may be bonded to a plurality of other groups through bonding groups. Specific examples of applicable bonding groups can include a methylene group (—$CH_2$—), an ether group (—O—), an ester group (—C(O)O—), a keto group (—C(O)—) group, a sulfonyl group (—$SO_2$—), a sulfinyl group (—SO—), a sulfenyl group (—S—), and a 9,9-fluorenylidene group.

Regarding the above-described divalent groups containing a cyclic structure, the position of substitution is not specifically limited. For example, in the case of a phenylene group, substitution at positions 1 and 4 is preferable because the structure of -Q- becomes straight and it is expected that the heat resistance increases and the coefficient of linear expansion decreases. On the other hand, substitution at positions 1 and 3 in a phenylene group is preferable because the -Q- structure is bent and it is expected that the solubility in a solvent is improved. Therefore, it is preferable that the positions of substitution are selected appropriately in such a way as to allow Q to have structures suitable for the required properties.

In a more preferable structure, Q is a group including an aromatic group. If Q includes an aromatic group, the heat resistance and the dimension stability of the resulting polyimide resin are further improved and, in addition, an improvement of the refractive index is achieved. As for the aromatic group of Q, specifically, those described above can be applied. Among them, a phenylene group, a biphenylene group, a diphenyl ether group, a diphenylsulfone group, a 4,4'-(9,9-fluorenylidene)diphenyl group, a 3,3',5,5'-tetramethyl-1,1'-biphenyl group, and the like are particularly preferable because the structure becomes more rigid.

$R^{11}$ and $R^{12}$ represent independently a hydrogen atom or an alkyl group or a silyl group, which has the carbon number of 1 to 12. Examples of usable alkyl groups include a methyl group, an ethyl group, a n-propyl group, and an i-propyl group. Examples of usable silyl groups include a trimethylsilyl group, a triethylsilyl group, and a dimethyl-t-butylsilyl group. Most of all, a trimethylsilyl group and a dimethyl-t-butylsilyl group are preferable because the leaving ability is high. $R^{11}$ and $R^{12}$ may be the same or be different. However, it is preferable that they are the same.

Regarding the structure in which B, Q, $R^{11}$, $R^{12}$, n, $X^1$, $X^2$, $X^3$, $X^4$, $X^5$, and $X^6$ are in preferable combination, B and Q are independently a group having a circular structure, $X^1$, $X^2$, $X^3$, $X^4$, $X^5$, and $X^6$ are independently composed of a halogen atom or a hydrogen atom, n is 1, and $R^{11}$ and $R^{12}$ are composed of any one of a hydrogen atom, a methyl group, an ethyl group, a trimethylsilyl group, and a dimethyl-t-butylsilyl group. More preferably, Q has a structure containing a circular structure, B is a norbornane ring, all $X^1$, $X^2$, $X^3$, $X^4$, $X^5$, and $X^6$ are a hydrogen atom, n is 1, and $R^{11}$ and $R^{12}$ are any one of a hydrogen atom, a methyl group, and a trimethylsilyl group.

[Method for Producing Tetracarboxylic Acid Compound]

The tetracarboxylic acid compound according to the present invention can be produced by using, for example, commercially available 5-norbornene-2,3-dicarboxylic anhydride as a raw material. That is, a carboxyl group is introduced into an olefin portion of 5-norbornene-2,3-dicarboxylic anhydride, this carboxyl group is reacted with a divalent alcohol or amine, or a monovalent alcohol or amine containing dicarboxylic anhydride to effect esterification or amidation, so that the tetracarboxylic anhydride represented by the general formula (1) or (2) can be synthesized.

This method will be described below.

In the following description, the tetracarboxylic anhydride is produced by using 5-norbornene-2,3-dicarboxylic anhydride as a raw material. A tetracarboxylic anhydride including a bicycle[2.2.2]octane ring can be similarly produced by using bicycle[2.2.2]octane-5-ene-2,3-dicarboxylic anhydride, which is a product of a Diels-Alder reaction between cyclohexadiene and maleic anhydride, as a raw material.

(Method for Producing Norbornane-2,3,5-Tricarboxylic Acid)

[1] Synthesis of Norbornane-2,3,5-tricarboxylic Acid (2,3,5-norbornane Carboxylic Acid) from 5-norbornene-2,3-dicarboxylic Anhydride

[Chemical formula 21]

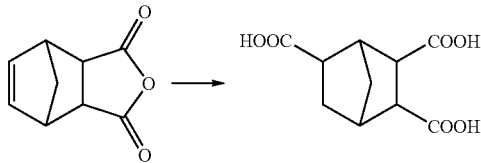

The olefin portion of 5-norbornene-2,3-dicarboxylic anhydride is carboxylated so as to synthesize 2,3,5-norbornanetricarboxylic acid.

The olefin portion of a norbornene ring of 5-norbornene-2,3-dicarboxylic anhydride exhibits high activity and easily undergoes various addition reactions. Taking advantage of this, 5-cyanonorbornane-2,3-dicarboxylic anhydride is obtained by addition of HCN, for example. The nitrile group thereof is hydrolyzed so as to obtain norbornanetricarboxylic acid. The method described in, for example, Japanese Unexamined Patent Application Publication No. 5-58946 can be applied to the addition reaction of HCN to the olefin of the norbornene ring and the hydrolysis of the nitrile group.

The carboxyl group can also be introduced by hydroesterification of the olefin of 5-norbornene-2,3-dicarboxylic anhydride and following hydrolysis of the ester group. As for the condition of this reaction, the method described in, for example, U.S. Pat. No. 3,413,317 can be adopted. This is a method for conducting the reaction in a nitrogen atmosphere by using Ni $(CO)_4$ as a carbonyl source.

On the other hand, it is also possible to adopt a method in which pressurized carbon monoxide and alcohol are reacted in the presence of a Pd, Ni, or Co catalyst as another method of hydroesterification. Regarding the method for adding the Pd catalyst used at that time, there are two addition methods, i.e. a method in which a Pd-phosphine complex is added to the reaction system and a method in which an inorganic salt of Pd or a Pd metal supported by an elementary substance and an alkylphosphine are added separately, and a Pd-phosphine complex is formed in the system. Examples of Pd compounds in the former case where a Pd-phosphine complex is added to the system include alkylphosphine palladium complexes, e.g., tetrakis(triphenylphosphine)palladium(0); halogenated alkylphosphine palladium complexes, e.g., dichlorobis(trimethylphosphine)palladium(II); carbonylalkylphosphine palladium complexes, e.g., carbonyltris(triphenylphosphine)palladium(0); and dichlorobis(acetonitrile)palladium(II). Examples of favorably used Pd compounds in the latter case where an inorganic salt of Pd is added to the system include salts of inorganic acid or organic acid of palladium, e.g., palladium chloride and palladium acetate.

On the other hand, examples of Ni catalysts include nickel carbonyl complexes, e.g., tetracarbonyl nickel(0); nickel carbonyl alkylphosphine complexes, e.g., dicarbonylbis(triphenylphosphine)nickel(0); and nickel alkylphosphine complexes, e.g., tetrakis(triphenylphosphine)nickel(0).

Examples of Co catalysts include cobalt carbonyl complexes, e.g., cobalt carbonyl.

The hydroesterification reaction is usually conducted in the presence of an alcohol solvent. The alcohol solvent not only serves a function as a dissolving agent for a substrate and a catalyst, but also serves a function as a reaction reagent to constitute the resulting ester portion. Examples of alcohol solvents usable for the present reaction include methanol, ethanol, isopropanol, n-propanol, and n-butanol, which are lower alcohols having the carbon number of 6 or less.

The hydroesterification reaction in this case is conducted in the presence of carbon monoxide. The pressure of monoxide carbon used may be normal pressure. However, the reaction may be conducted under pressure in order to increase the reaction speed. The lower limit of the pressure used is 0.1 MPa or more, preferably 0.5 MPa or more, and more preferably 1.0 MPa or more. The upper limit is not particularly specified. However, usually 30 MPa or less, preferably 20 MPa or less, and more preferably 15 MPa or less is adopted from the viewpoint of equipment problems. The reaction is conducted usually under heating, and the lower limit of the reaction temperature adopted is 20° C. or higher, preferably 50° C. or higher, and more preferably 70° C. or higher. The upper limit is usually 300° C. or lower, preferably 250° C. or lower, and more preferably 200° C. or lower in consideration of the restriction based on the equipment.

Regarding the reaction time, the lower limit is usually 10 minutes or more, preferably 30 minutes or more, and more preferably 1 hour or more. The upper limit is usually 100 hours or less, preferably 50 hours or less, and more preferably 25 hours or less.

In the reaction, a copper salt or a tin salt serving as a reaction promoter may be added so as to conduct the reaction. As for the copper salt used at that time, salts of inorganic acids of copper, e.g., copper chloride ($CuCl_2$) and copper acetate, are preferable. As for the tin salt, halides of tin, e.g., tin chloride ($SnCl_2$) and tin bromide ($SnBr_2$), are preferable.

Furthermore, the reaction can also be conducted by adding an acid in order to facilitate the reaction. Examples of acids usable at that time include organic sulfonic acid, e.g., p-toluenesulfonic acid and methanesulfonic acid, and inorganic acids, e.g., hydrochloric acid and sulfuric acid.

The yield of hydroesterification of the olefin portion of 5-norbornene-2,3-dicarboxylic anhydride in a typical case is 40% or more, preferably 50% or more, and more preferably 60% or more although depending on the type of alcohol used.

The purity of the desired hydroester body is usually 50 percent by weight or more, preferably 60 percent by weight or more, and more preferably 70 percent by weight or more.

The acid anhydride ring of the norbornane acid anhydride with the olefin portion hydroesterified as described above has been converted to a half ester or diester of the alcohol used as the solvent. Specific products at this time are as described below.

<Use of Endo-5-norbornene-2,3-dicarboxylic Anhydride as Raw Material>

[Chemical formula 22]

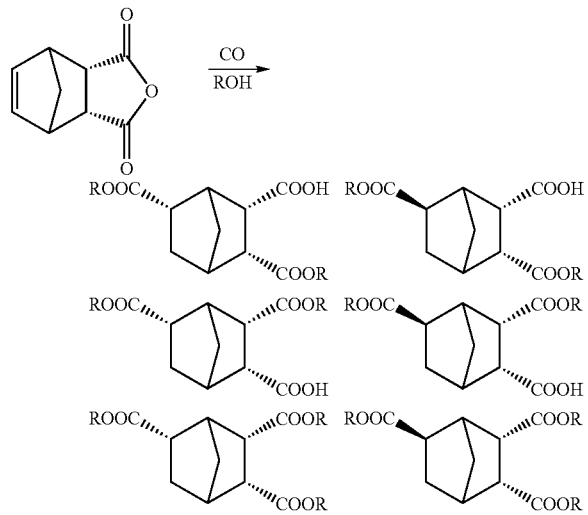

<Use of Exo-5-norbornene-2,3-dicarboxylic Anhydride as Raw Material>

[Chemical formula 23]

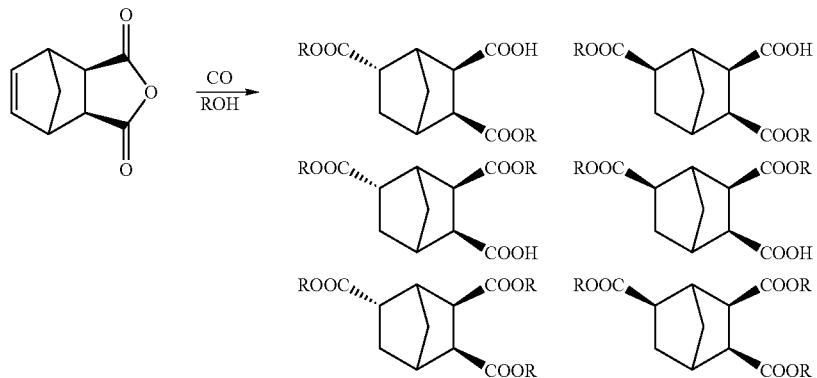

In addition to these products, stereoisomers thereof (products in which endo-exo of a part of or all substituents on the norbornane ring are inverted) are further produced. However, in a usual hydroesterification reaction, the compounds having the above-described structure are primarily produced, and a total content of the above-described products contained in the entire products is usually 50% or more, preferably 70% or more, and more preferably 80% or more.

Furthermore, among the above-described compounds, regarding solids of newly introduced carboalkoxy groups (position 5), primary products are usually of exo type. The proportion of compounds, in which solids of carboalkoxy groups at position 5 are of exo type, contained in the entire products is usually 60% or more, preferably 70% or more, and more preferably 80% or more.

The hydroester body obtained through hydroesterification, that is, norbornane diester carboxylic acid or norbornane triester is converted to norbornanetricarboxylic acid by hydrolysis of the ester group. At that time, either an alkaline condition or an acidic condition can be adopted.

For example, in the case where the hydrolysis is conducted under the alkaline condition, the hydrolysis is conducted in the presence of water and an alkaline component. The alkaline components usable at this time are aqueous solutions of hydroxides of alkali metals or alkaline earth metals, e.g., sodium hydroxide, potassium hydroxide, and calcium hydroxide; carbonates of alkali metals and alkaline earth metals, e.g., sodium hydrogencarbonate and sodium carbonate; and the like. The reaction may be conducted by using these aqueous solutions of alkaline compounds alone, but organic solvents may be added. The solvents usable at that time are not specifically limited. However, lower alcohols, e.g., methanol and ethanol; ether solvents, e.g., tetrahydrofuran and dimethoxyethane; nitrile solvents, e.g., acetonitrile; and the like are preferable because they are compatible with water-based solvents. Furthermore, the reaction may be conducted in a two-phase system by using solvents not compatible with water, for example, aromatic hydrocarbons, e.g., toluene and xylene; aliphatic hydrocarbons, e.g., heptane, hexane, and cyclohexane; halogen solvents, e.g., dichloromethane and 1,2-dichloroethane; and the like.

The reaction temperature in the hydrolysis is not specifically limited. However, regarding the reaction, the lower limit of the reaction temperature is $-10°$ C. or higher, preferably $0°$ C. or higher, and more preferably $10°$ C. or higher. The upper limit is $150°$ C. or lower, preferably $100°$ C. or lower, and more preferably $80°$ C. or lower.

Regarding the reaction time, the lower limit is usually 10 minutes or more, preferably 30 minutes or more, and more preferably 1 hour or more. The upper limit is not particularly specified, but is usually 100 hours or less, preferably 50 hours or less, and more preferably 25 hours or less.

The product after the reaction is a metal salt of 2,3,5-norbornanetricarboxylic acid. Therefore, this is taken out as a carboxylic acid by using an acid. For this purpose, the acid is added to the solution of the metal salt of 2,3,5-norbornanetricarboxylic acid so as to convert the metal salt of the carboxylic acid to the carboxylic acid. Examples of acids usable at that time include aqueous solutions of inorganic acids, e.g., hydrochloric acid, sulfuric acid, nitric acid, and phosphoric acid.

On the other hand, in the case where the hydrolysis is conducted under the acidic condition, the reaction may be conducted in the presence of water and an acidic component. In particular, known methods can be adopted as the method therefor without modification. Examples of usable acids include inorganic acids, e.g., sulfuric acid, hydrochloric acid, nitric acid, and phosphoric acid, and organic acids, e.g., p-toluenesulfonic acid and methanesulfonic acid.

Regarding the usage of the acidic component relative to the weight of the hydroester body serving as a substrate, the lower limit is 5 percent by weight, and preferably 10 percent by weight. The upper limit is 200 percent by weight, and preferably 100 percent by weight, although not specifically limited.

A solvent may be used in the reaction. The solvents usable at that time are not specifically limited. However, lower alcohols, e.g., methanol and ethanol; ether solvents, e.g., tetrahydrofuran and dimethoxyethane; nitrile solvents, e.g., acetonitrile; sulfur-atom-containing solvents, e.g., sulfolane and dimethylsuloxide, and the like are preferable because they are compatible with water-based solvents. Furthermore, the reaction may be conducted in a two-phase system by using solvents not compatible with water, for example, aromatic hydrocarbons, e.g., toluene and xylene; aliphatic hydrocarbons, e.g., heptane, hexane, and cyclohexane; halogen solvents, e.g., dichloromethane and 1,2-dichloroethane; and the like.

At that time, regarding the usage of the solvent, the amount is determined in such a way that the lower limit of the weight concentration of the hydroester body serving as a substrate is 1%, preferably 5%, and more preferably 10%. The upper limit thereof is 80%, preferably 70%, and more preferably 60%.

The amount of water used in the charge for reaction is determined in such a way that the lower limit of the hydroester body serving as a substrate is 30 percent by weight or more, preferably 50 percent by weight or more, and more preferably 100 percent by weight or more. The upper limit thereof is 300 percent by weight or less, and preferably 200 percent by weight or less, although not specifically limited.

The reaction temperature in the hydrolysis is not specifically limited. However, regarding the reaction, the lower limit of the reaction temperature is 20° C. or higher, preferably 40° C. or higher, and more preferably 60° C. or higher. The upper limit is 200° C. or lower, preferably 150° C. or lower, and more preferably 120° C. or lower.

Regarding the reaction time, the lower limit is usually 10 minutes or more, preferably 30 minutes or more, and more preferably 1 hour or more. The upper limit is not particularly specified, but is usually 100 hours or less, preferably 50 hours or less, and more preferably 25 hours or less.

It is preferable that the reaction is conducted while by-product alcohol derived from the ester is removed during the reaction because the equilibrium shifts to the production system (tricarboxylic acid) side. In the case where the water serving as the reaction reagent is also removed in the removal of the alcohol, it is preferable that the reaction is conducted while water is supplied successively.

The yield of the thus obtained norbornane-2,3,5-tricarboxylic acid is usually 60% or more, preferably 70% or more, and more preferably 80% or more.

The primary components of the product have the following structures.

<Use of Hydroesterification Product of Endo-5-norbornene-2,3-dicarboxylic Anhydride as Raw Material>

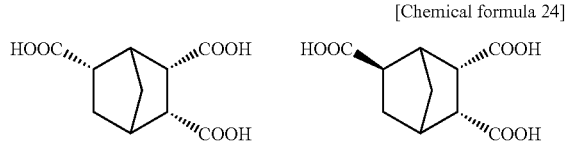

[Chemical formula 24]

<Use of Hydroesterification Product of Exo-5-norbornene-2,3-dicarboxylic Anhydride as Raw Material>

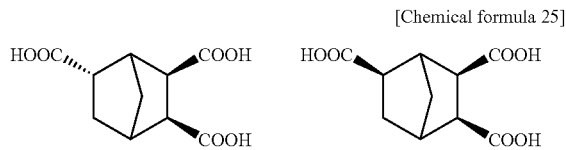

[Chemical formula 25]

In addition to the compounds having the above-described structures, stereoisomers thereof (products in which endo-exo of a part of or all substituents on the norbornane ring are inverted) are present together. However, usually, the compounds having the above-described structure are primarily produced, and a total content of the above-described products contained in the entire products is usually 50% or more, preferably 70% or more, and more preferably 80% or more.

The thus obtained norbornane-2,3,5-tricarboxylic acid can be used in the following esterification step without being treated, but may be used after being refined to increase the purity. The refining method is not specifically limited, and common methods, e.g., a sublimation method, a recrystallization method, column chromatography, and extraction refining, can be adopted at will. Most of all, the recrystallization method is preferable because of simpleness and low cost.

The solvent usable in the recrystallization is not specifically limited insofar as norbornane-2,3,5-tricarboxylic acid is dissolved into the solvent. Specifically, ether solvents, e.g., tetrahydrofuran, dimethoxyethane, and dioxane; nitrile solvents, e.g., acetonitrile; aprotic polar solvents, e.g., sulfolane, dimethylsuloxide, and N-methylpyrrolidone; halogen solvents, e.g., dichloromethane and 1,2-dichloroethane; ester solvents, e.g., ethyl acetate and butyl acetate; and the like can be used. Furthermore, in addition to these good solvents, poor solvents, for example, aromatic hydrocarbons, e.g., toluene and xylene; aliphatic hydrocarbons, e.g., heptane, hexane, and cyclohexane; and the like may be added and used. The recovery factor of the desired product can be increased by addition of the poor solvent.

The purity of the thus refined norbornane-2,3,5-tricarboxylic acid is usually 80% or more, preferably 90% or more, and more preferably 95% or more.

[2] Synthesis of Tetracarboxylic Acid Compound According to the Present Invention from 2,3,5-Norbornanetricarboxylic acid

[Chemical formula 26]

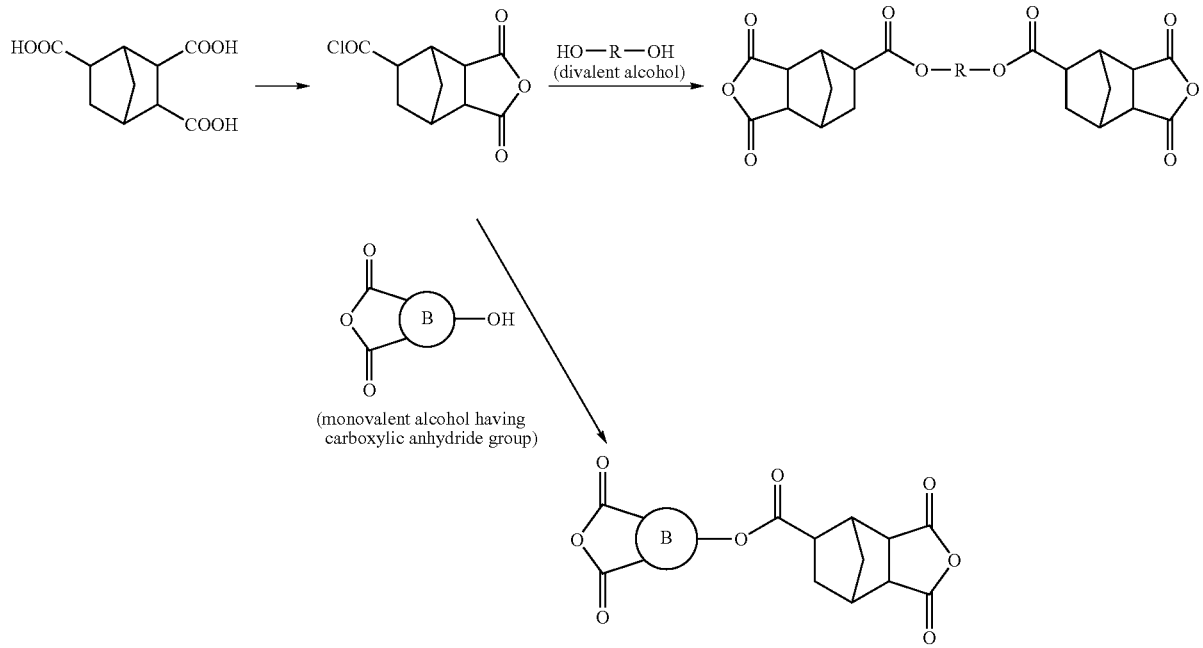

The tetracarboxylic acid compound according to the present invention can be derived from 2,3,5-norbornanetricarboxylic acid by, for example, converting the carboxyl groups at positions 2 and 3 to acid anhydrides and, thereafter, condensing the carboxyl group at position 5 with a divalent alcohol or amine, or an alcohol or amine containing a dicarboxylic anhydride group.

As for the method for converting the carboxyl groups at positions 2 and 3 of 2,3,5-norbornanetricarboxylic acid to acid anhydrides, a method in which heating is conducted under reduced pressure or a method in which a treatment is conducted together with an acid anhydride of an organic acid can be adopted.

In the case where the heat treatment is conducted under reduced pressure, the lower limit of the adopted temperature is 50° C. or higher, and preferably 120° C. or higher. The upper limit is 250° C. or lower, and preferably 200° C. or lower.

There is no lower limit of the reduced pressure. The upper limit is 0.1 MPa or less, and preferably 0.05 MPa or less.

Examples of acid anhydrides of organic acids used in the case where the treatment is conducted together with an acid anhydride of an organic acid include acetic anhydride, propionic anhydride, maleic anhydride, and phthalic anhydride. Preferably, acetic anhydride is used because removal is easy when it is used excessively.

Regarding the temperature adopted in the treatment, the lower limit is 30° C. or higher, and preferably 50° C. or higher. The upper limit is 200° C. or lower, and preferably 150° C. or lower.

Subsequently, the carboxyl group at position 5 of the thus obtained 5-carboxynorbornane-2,3-dicarboxylic anhydride is condensed with a divalent alcohol or amine, or an alcohol or amine containing a dicarboxylic anhydride group. As for the condensation reaction at that time, organic synthesis reactions usually known as an esterification reaction or an amidation reaction can be adopted at will. For example, a method in which a carboxylic acid, an alcohol, and an amine are dehydrated directly so as to condense, a method in which dehydration and condensation are conducted by using dehydration reagents, e.g., dicyclohexylcarbodiimide (abbreviated as DCC) and a combination of diethylazocarboxylate/triphenylphosphine, and the like are included. Furthermore, a method in which a carboxylic acid is converted to an acid halide or acid anhydride exhibiting higher reactivity (higher electrophilicity) and reacted with an alcohol or amine in the presence of a base can also be adopted. It is also possible to use a method in which a carboxylic acid and an alcohol ester of carboxylic acid are subjected to an ester exchange reaction as a method for synthesizing an ester.

Among the above-described methods, the method by using direct dehydration, the method by using ester exchange, and the method by using conversion to an acid halide are preferable from the viewpoint of economic efficiency and reactivity. A method for producing tetracarboxylic anhydride containing a norbornane structure by way of an acid chloride will be described below.

In this case, the carboxyl group at position 5 of 5-carboxynorbornane-2,3-dicarboxylic anhydride is converted to an acid chloride, and this is reacted with a divalent alcohol or amine, or an alcohol or amine containing a dicarboxylic anhydride group, so as to effect esterification or amidation.

As for a method for converting the carboxyl group at position 5 to an acid chloride in order to synthesize 5-chloroformylnorbornane-2,3-dicarboxylic anhydride, a common organic synthesis technique for synthesizing an acid chloride from a corresponding carboxylic acid can be used. Specific examples thereof include a method by using thionyl chloride, a method by using oxalyl chloride, a method by using phosphorous trichloride, and a method by using other acid chloride, e.g., benzoic acid chloride. Most of all, the method by using thionyl chloride is preferable because excessively used reagent is easily removed.

A method by way of an acid bromide can be conducted in a similar manner by using thionyl bromide, oxalyl bromide, phosphorous trichloride, benzoic acid bromide, and the like.

In the chlorination of the carboxylic acid at position 5 by using these chlorination reagents, a catalyst, e.g., N,N-dimethylformamide or pyridine, can be used as well. However, in some cases, there is no harm in proceeding of the reaction without using the catalysts. If anything, the resulting chloride may be colored significantly because of the presence of the catalyst. In the use where the transparency of the polyimide film is important, it is required to care to avoid coloring of the product. In that case, it is preferable that the production is conducted without using these catalysts.

Regarding the usage of the chlorination reagent, the amount larger than or equal to the amount of the substrate is adopted. The lower limit is usually 1 molar equivalent or more, preferably 5 molar equivalent or more, and more preferably 10 molar equivalent or more. The upper limit is not particularly specified. However, the amount of 100 molar equivalent or less, and preferably 50 molar equivalent or less is used from the viewpoint of economic efficiency.

The reaction of conversion to the acid chloride by using the chlorination reagent may be conducted by using a catalyst. The solvent usable at that time is not specifically limited insofar as the chlorination reagent and the product, i.e. acid anhydride chloride, are dissolved into the solvent and the chlorination reagent do not react with the solvent. Examples of usable solvents include aromatic hydrocarbon solvents, e.g., toluene and xylene; aliphatic hydrocarbon solvents, e.g., hexane and heptane; ether solvents, e.g., diethyl ether, tetrahydrofuran, monoethylene glycol dimethyl ether, and diethylene glycol dimethyl ether; ketone solvents, e.g., acetone, methyl ethyl ketone, and methyl isobutyl ketone; ester solvents, e.g., ethyl acetate, butyl acetate, and gamma-butyrolactone; and amide solvents, e.g., dimethylformamide, dimethylacetamide, and N-methylpyrrolidone. Most of all, toluene, heptane, and tetrahydrofuran are preferable from the viewpoint of the solubility and the stability. These solvents may be used alone, or any mixture of a plurality of solvents may be used. Regarding the usage of the solvent, the lower limit of the weight concentration of 5-carboxynorbornane-2, 3-dicarboxylic anhydride serving as a substrate is usually 5 percent by weight, and preferably 10 percent by weight. The upper limit thereof is 50 percent by weight, and preferably 40 percent by weight.

The reaction can be conducted at room temperature, but is conducted usually under heating. The lower limit of temperature adopted is 30° C. or higher, and preferably 50° C. or higher. The upper limit is a reflux temperature of the chlorination reagent used.

After the reaction, an excessively used chlorination reagent is removed. The method of removal is not specifically limited, and distillation, extraction, and the like can be applied. In the case where removal is conducted by distillation, in order to increase the efficiency, a solvent which forms an azeotropic composition with the chlorination reagent may be added so as to conduct the removal by distillation. For example, in the case where thionyl chloride is removed by distillation, benzene or toluene is added and, thereby, removal by azeotropic distillation can be conducted.

The purity of the resulting chlorinated acid can be increased through recrystallization by using a nonpolar solvent, e.g., hexane or cyclohexane. However, there is no problem in using for the following reaction step without such a refining operation and the like.

Specific examples of nonpolar solvents usable for the recrystallization of the resulting chlorinated acid include ether solvents, e.g., tetrahydrofuran, dimethoxyethane, and dioxane; nitrile solvents, e.g., acetonitrile; aprotic polar solvents, e.g., sulfolane, dimethylsuloxide, and N-methylpyrrolidone; halogen solvents, e.g., dichloromethane and 1,2-dichloroethane; ester solvents, e.g., ethyl acetate and butyl acetate. Furthermore, in addition to these good solvents, poor solvents, for example, aromatic hydrocarbons, e.g., toluene and xylene; aliphatic hydrocarbons, e.g., heptane, hexane, and cyclohexane; and the like may be added and used. The recovery factor of the desired product can be increased by addition of the poor solvent.

The purity of the thus refined, if necessary, 5-chloroformylnorbornane-2,3-dicarboxylic anhydride is usually 90% or more, preferably 95% or more, and more preferably 98% or more. Major impurities include diacid chloride bodies and triacid chloride bodies (including stereoisomers) produced by acid chlorination of a plurality of carboxyl groups of tricarboxylic acid due to cleavage of the acid anhydride and decomposition products of dimethylformamide and dimethylamide bodies of 2,3,5-norbornanetricarboxylic acid in the case where dimethylformamide is used as a catalyst. It is preferable that the amount of presence of them is smaller. The amount is usually 5 percent by weight or less, further preferably 3 percent by weight or less, and more preferably 1 percent by weight or less.

In the method explained in the above description, the tricarboxylic acid is converted to the acid anhydride and, thereafter conversion to the acid chloride is conducted stepwise. However, it is also possible that the tricarboxylic acid is treated with the above-described chlorination reagent directly and, thereby, conversion to 5-chloroformylnorbornane-2,3-dicarboxylic anhydride is conducted by one operation. Regarding the usage of chlorination reagent at that time, the lower limit is usually 2 molar equivalent or more, preferably 5 molar equivalent or more, and more preferably 10 molar equivalent or more. On the other hand, the upper limit is not specifically limited. However, the amount of 100 molar equivalent or less, and preferably 50 molar equivalent or less is used from the viewpoint of economic efficiency. As for the type, the reaction temperature, and the reaction and refining techniques, the above-described conditions can be adopted without modification.

The thus obtained 5-chloroformylnorbornane-2,3-dicarboxylic anhydride, which is the acid halide according to the present invention, is reacted with a divalent alcohol or amine, or a monovalent alcohol or amine containing a dicarboxylic anhydride group to effect esterification or amidation, so that a norbornane-structure-containing tetracarboxylic anhydride, which is represented by the general formula (1) or (2) and which is a compound according to the present invention can be synthesized.

The reaction between these alcohols or amines and acid chloride is conducted as described below.

Regarding the method for introducing the reaction reagent into a reaction container, a method in which alcohols or amines and a base are dissolved into a solvent, and 5-chloroformylnorbornane-2,3-dicarboxylic anhydride dissolved into the same solvent is dropped thereto slowly, a method in which, conversely, a mixed solution of alcohols or amines and a base is dropped to 5-chloroformylnorbornane-2,3-dicarboxylic anhydride dissolved into a solvent, if necessary, a method in which a base is dropped to a mixed solution of 5-chloroformylnorbornane-2,3-dicarboxylic anhydride and alcohols or amines, or the like can be adopted.

A white precipitation occurs as the reaction proceeds. After this is filtrated, the precipitate is washed with water sufficiently to remove generated hydrochloric acid salts. The precipitate of diester is heated and vacuum-dried, so that a crude product of desired ester-containing tetracarboxylic dianhydride can be obtained at a high yield. Furthermore, if necessary, recrystallization is conducted with an appropriate solvent and, thereby, tetracarboxylic dianhydride having an improved purity can be obtained.

Diols usable for the synthesis of tetracarboxylic acid compound according to the present invention are not specifically limited. Usually, diols having two hydroxyl groups on a single core aromatic ring, diols having two hydroxyl groups on an alicyclic skeleton, diols having one hydroxyl group on each of two cores of a biphenyl skeleton, diols having a structure in which two phenol residues or alicyclic alcohol residues are bonded with functional groups, e.g., a methylene group (—$CH_2$—), an ether group (—O—), an ester group (—C(O)O—), a keto group (—C(O)—) group, a sulfonyl group (—$SO_2$—), a sulfinyl group (—SO—), a sulfenyl group (—S—), and a 9,9-fluorenylidene group, diols having two hydroxyl groups on a naphthalene skeleton, and diols having two hydroxyl groups on a chain skeleton, and the like are used.

Specifically, examples of diols having two hydroxyl groups on a single core aromatic ring include hydroquinone, 2-methylhydroquinone, resorcinol, catechol, and 2-phenylhydroquinone. Examples of diols having one hydroxyl group on each of two cores of a biphenyl structure include 4,4'-biphenol, 3,4'-biphenol, 2,2'-biphenol, and 3,3',5,5'-tetramethyl-4,4'-biphenol. Examples of diols in which aromatic cores are bonded with divalent functional group include 4,4'-dihydroxybiphenyl ether, 4,4'-dihydroxydiphenylsulfone, 9,9'-bis(4-hydroxyphenyl)fluorene, 9,9'-bis(hydroxymethyl)fluorene, and 9,9'-bis(2-hydroxyethyl)fluorene. Examples of diols having two hydroxyl groups on a naphthalene skeleton include 2,6-naphthalenediol, 1,4-naphthalenediol, 1,5-naphthalenediol, and 1,8-naphthalenediol. Examples of diols having two hydroxyl groups on an alicyclic skeleton include 1,4-dihydroxycyclohexane, 1,3-dihydroxycyclohexane, 1,2-dihydroxycyclohexane, 1,3-adamantanediol, and dicycopentadiene dihydride. Examples of diols having hydroxyl groups in substituents on an alicyclic skeleton include cyclohexanedimethanol and tricycle[$5.2.1.0^{2,6}$]decanedimethanol. Examples of diols having hydroxyl groups on a ring including a hetero atom include 2,3-dihydroxytetrahydrofurane and isosorbide. Examples of diols having two hydroxyl groups on a chain skeleton include ethylene glycol and propylene glycol. More preferably, diols having a chain skeleton are mentioned. Furthermore, from the viewpoint of characteristics required of polymers, hydroquinone, 4,4'-biphenol, 1,4-dihydroxycyclohexane, 9,9'-bis(4-hydroxyphenyl)fluorene, 9,9'-bis(hydroxymethyl)fluorene, and 9,9'-bis(2-hydroxyethyl)fluorene are particularly preferable. At least two types of these diols can also be used in combination.

The tetracarboxylic acid compound according to the present invention can also be produced by reacting 5-chloroformylnorbornane-2,3-dicarboxylic anhydride with dicarboxylic anhydride containing a hydroxyl group. Examples of dicarboxylic anhydrides containing a hydroxyl group used at that time include 3-hydroxysuccinic anhydride, 3-hydroxymethylsuccinic anhydride, 5-hydroxynorbornane-2,3-dicarboxylic anhydride, and 4-hydroxyphthalic anhydride.

Diamines used for producing tetracarboxylic acid compound according to the present invention can be selected basically freely. Specific examples of usable diamines include aromatic diamines, e.g., 3,5-diaminobenzotrifluoride, 2,5-diaminobenzotrifluoride, 3,3'-bistrifluoromethyl-4,4'-diaminobiphenyl, 3,3'-bistrifluoromethyl-5,5'-diaminobiphenyl, bis(trifluoromethyl)-4,4'-diaminodiphenyl, bis(fluorinated alkyl)-4,4'-diaminodiphenyl, dichloro-4,4'-diaminodiphenyl, dibromo-4,4'-diaminodiphenyl, bis(fluorinated alkoxy)-4,4'-diaminodiphenyl, diphenyl-4,4'-diaminodiphenyl, 4,4'bis(4-aminotetrafluorophenoxy)tetrafluorobenzene, 4,4'-bis(4-aminotetrafluorophenoxy)octafluorobiphenyl, 4,4'-binaphthylamine, o-,m-,p-phenylenediamine, 2,4-diaminotoluene, 2,5-diaminotoluene, 2,4-diaminoxylene, 2,4-diaminodurene, dimethyl-4,4'-diaminodiphenyl, dialkyl-4,4'-diaminodiphenyl, dimethoxy-4,4'-diaminodiphenyl, diethoxy-4,4'-diaminodiphenyl, 4,4'-diaminodiphenylmethane, 4,4'-diaminodiphenyl ether, 3,4'-diaminodiphenyl ether, 4,4'-diaminodiphenylsulfone, 3,3'-diaminodiphenylsulfone, 4,4'-diaminobenzophenone, 3,3'-diaminobenzophenone, 1,3-bis(3-aminophenoxy)benzene, 1,3-bis(4-aminophenoxy)benzene, 1,4-bis(4-aminophenoxy)benzene, 4,4'-bis(4-aminophenoxy)biphenyl, bis(4-(3-aminophenoxy)phenyl)sulfone, bis(4-(4-aminophenoxy)phenyl)sulfone, 2,2-bis(4-(4-aminophenoxy)phenyl)propane, 2,2-bis(4-(4-aminophenoxy)phenyl)hexafluoropropane, 2,2-bis(4-(3-aminophenoxy)phenyl)propane, 2,2-bis(4-(3-aminophenoxy)phenyl)hexafluoropropane, 2,2-bis(4-(4-amino-2-trifluoromethylphenoxy)phenyl)hexafluoropropane, 2,2-bis(4-(3-amino-5-trifluoromethylphenoxy)phenyl)hexafluoropropane, 2,2-bis(4-aminophenyl)hexafluoropropane, 2,2-bis(3-aminophenyl)hexafluoropropane, 2,2-bis(3-amino-4-hydroxyphenyl)hexafluoropropane, 2,2-bis(3-amino-4-methylphenyl)hexafluoropropane, 4,4'-bis(4-aminophenoxy)octafluorobiphenyl, and 4,4'-diaminobenzanilide. At least two types thereof can also be used in combination.

Examples of aliphatic amines include 4,4'-methylenebis(cyclohexylamine), isophoronediamine, trans-1,4-diaminocyclohexane, cis-1,4-diaminocyclohexane, 1,4-cyclohexanebis(methylamine), 2,5-bis(aminomethyl)bicyclo[2.2.1]heptane, 2,6-bis(aminomethyl)bicyclo[2.2.1]heptane, 3,8-bis(aminomethyl)tricyclo[5.2.1.0]decane, 1,3-diaminoadamantane, 2,2-bis(4-aminocyclohexyl)propane, 2,2-bis(4-aminocyclohexyl)hexafluoropropane, 1,3-propanediamine, 1,4-tetramethylenediamine, 1,5-pentamethylenediamine, 1,6-hexamethylenediamine, 1,7-heptamethylenediamine, 1,8-octamethylenediamine, and 1,9-nonamethylenediamine. At least two types thereof can be used in combination, and the above-described aromatic diamines can be used in combination.

Among these diamines, as for aromatic diamines, monophenyldiamine compounds, e.g., o-,m-,p-phenylenediamine; diaminodiphenyl compounds, e.g., 4,4'-diaminodiphenyl, 4,4'-diaminodiphenylsulfone, 4,4'-diaminodiphenylmethane, and 4,4'-diaminodiphenyl ether; and the like are preferable. Most of all, p-phenylenediamine, 4,4'-diaminodiphenyl ether, and 4,4'-diaminodiphenyl are more preferable because of ease of availability and good properties of the resulting resins. As for aliphatic diamines, alicyclic diamines, e.g., 4,4'-methylenebis(cyclohexylamine) and trans-1,4-diaminocyclohexane, are more preferable because of a ring structure and ease of availability. Furthermore, trans-1,4-diaminocyclohexane is more preferable because of good properties of the resulting resins.

Regarding the usage of the diol or diamines relative to 5-chloroformylnorbornane-2,3-dicarboxylic anhydride, the upper limit is usually 0.6 molar equivalent or less, and preferably 0.5 molar equivalent or less. If the usage is larger than this, unfavorably, a high proportion of half esters or half amides, in which merely one diol or diamine is esterified, are generated. The lower limit is 0.3 molar equivalent or more, and preferably 0.45 molar equivalent or more. If the usage is smaller than this, unfavorably, excess 5-chloroformylnorbornane-2,3-dicarboxylic anhydride presents in the system. Usually, about 0.5 molar equivalent of diol or diamines is used relative to 5-chloroformylnorbornane-2,3-dicarboxylic anhydride.

The solvent usable in the synthesis of the norbornane-structure-containing tetracarboxylic anhydride by reacting 5-chloroformylnorbornane-2,3-dicarboxylic anhydride with alcohols or amines is not specifically limited. Examples thereof include ether solvents, e.g., tetrahydrofuran, 1,4-dioxane, and 1,2-dimethoxyethane-bis(2-methoxyethyl)ether; aromatic amine solvents, e.g., picoline and pyridine; ketone solvents, e.g., acetone and methyl ethyl ketone; aromatic hydrocarbon solvents, e.g., toluene and xylene; halogen-containing solvents, e.g., dichloromethane, chloroform, and 1,2-dichloroethane; amide solvents, e.g., N-methyl-2-pyrrolidone, N,N-dimethylacetamide, N,N-diethylacetamide, and N,N-dimethylformamide; phosphorus-containing solvents, e.g., hexamethylphosphonamide; sulfur-containing solvents, e.g., dimethylsulfoxide; ester solvents, e.g., γ-butyrolactone, ethyl acetate, and butyl acetate; nitrogen-containing solvents, e.g., 1,3-dimethyl-2-imidazolidinone; and aromatic solvents having a hydroxyl group, e.g., phenol, o-cresol, m-cresol, p-cresol, o-chlorophenol, m-chlorophenol, and p-chlorophenol. One type of these solvents may be used alone, or at least two types may be used as a mixture.

Regarding the concentration of a solute in a reaction solution in the reaction for obtaining the tetracarboxylic acid compound according to the present invention, the lower limit is 1 percent by weight or more, and preferably 10 percent by weight or more. The upper limit is 50 percent by weight or less, and preferably 40 percent by weight or less. It is more preferable that the reaction is conducted within the range of 10 percent by weight or more, and 40 percent by weight or less in consideration of the control of side reactions and the step of filtration of precipitation.

Regarding the reaction temperature adopted in the synthesis of the tetracarboxylic acid compound according to the present invention, the lower limit is −10° C. or higher, preferably −5° C. or higher, and more preferably 0° C. or higher. The upper limit is 30° C. or lower, preferably 20° C. or lower, and more preferably 10° C. or lower. If the reaction temperature is higher than 30° C., unfavorably, side reactions may occur partly, and the yield may be reduced.

The reaction is usually conducted at normal pressure. If necessary, the reaction can be conducted under pressure or under reduced pressure. Usually, the reaction is conducted in a nitrogen atmosphere.

The reaction container may be either a closed type reaction container or an open type reaction container. In order to keep the reaction system in an inert atmosphere, a reaction container which can be sealed with an inert gas is used in the case of the open type.

In the reaction, the base is used for neutralizing hydrogen chloride generated as the reaction proceeds.

The type of the base used at this time is not specifically limited. Organic tertiary amines, e.g., pyridine, triethylamine, and N,N-dimethylaniline, and inorganic bases, e.g., potassium carbonate and sodium hydroxide, can be used.

[Method for Refining Tetracarboxylic Acid Compound According to the Present Invention]

The precipitate generated by the above-described reaction is a mixture of the desired product and hydrochloric acid salts. In order to remove the hydrochloric acid salts, it is possible to conduct a method in which the precipitate is extracted and dissolved with chloroform, ethyl acetate, or the like, and an organic layer is washed with water by using a separating funnel. However, the hydrochloric acid salts can be completely removed simply by washing the precipitate sufficiently. The removal of the hydrochloric acid salts is judged by adding a silver nitrate aqueous solution to a washing solution and checking whether a white precipitate of silver chloride is generated or not.

In the water washing operation, a part of tetracarboxylic anhydride undergoes hydrolysis and is converted to tetracarboxylic acids. However, they can easily be returned to tetracarboxylic dianhydride according to the present invention by a heat treatment under reduced pressure.

Regarding the temperature adopted at that time, the lower limit is 50° C. or higher, and preferably 120° C. or higher. The upper limit is 250° C. or lower, and preferably 200° C. or lower.

Regarding the degree of the reduced pressure adopted for the ring closure treatment, there is no lower limit, and the upper limit is 0.1 MPa or less, and preferably 0.05 MPa or less.

As for a method for reclosing the ring in the case where tetracarboxylic acid is produced because of the hydrolysis, in addition to the above-described method in which heating is conducted under reduced pressure, a method in which a treatment with an acid anhydride of an organic acid is conducted can be adopted. Examples of acid anhydrides of organic acids used at that time include acetic anhydride, propionic anhydride, maleic anhydride, and phthalic anhydride. Preferably, acetic anhydride is used because removal is easy when it is used excessively.

The thus obtained tetracarboxylic anhydride according to the present invention can be further refined. As for the refining method in that case, recrystallization, sublimation, washing, an activated carbon treatment, column chromatography, and the like can be conducted at will. These refining methods can be repeated, and also be conducted in combination.

The solvent usable in the recrystallization is not specifically limited insofar as tetracarboxylic anhydride is dissolved into the solvent.

Specifically, ether solvents, e.g., tetrahydrofuran, dimethoxyethane, and dioxane; nitrile solvents, e.g., acetonitrile; aprotic polar solvents, e.g., sulfolane, dimethylsuloxide, N-methylpyrrolidone, γ-butyrolactone, dimethylformamide, and dimethylacetamide; halogen solvents, e.g., dichloromethane and 1,2-dichloroethane; and ester solvents, e.g., ethyl acetate and butyl acetate. Furthermore, in addition to these good solvents, poor solvents, for example, aromatic hydrocarbons, e.g., toluene and xylene; aliphatic hydrocarbons, e.g., heptane, hexane, and cyclohexane; and the like may be added and used. The recovery factor of the desired product can be increased by addition of the poor solvent.

In the recrystallization, a dehydrating agent may be present together to prevent ring cleavage of the acid anhydride. Examples of dehydrating agent usable at that time include acetic anhydride, propionic anhydride, and maleic anhydride.

The purity of the thus obtained tetracarboxylic anhydride according to the present invention is, for example, usually 90% or more, preferably 95% or more, and more preferably 98% or more in terms of peak area ratio obtained by the analysis with, for example, a high-speed liquid chromatography with differential fractometer.

Examples of impurities include a monoester body which is resulted from esterification of only one part of diol and a ring closure agent in the case where an acid anhydride, e.g., acetic anhydride, is used as the ring closure agent in the refining. Since these impurities have one acid anhydride structure in the molecule, they function as a polymerization terminator in polymerization with diamines. Therefore, it is necessary that the impurities are removed from the tetracarboxylic anhydride as much as possible. The content of the acid anhydride, e.g., acetic anhydride, contained in the tetracarboxylic anhydride is preferably 10 percent by mole or less, more preferably 5 percent by mole or less, and further preferably 2 percent by mole or less. If the content of impurities is more than this, the degree of polymerization may not increase in the polymerization with diamines.

The yield of synthesis of ester-containing alicyclic tetracarboxylic anhydride according to the present invention by esterification of the above-described 5-chloroformylnorbornane-2,3-dicarboxylic anhydride and diol after refining is usually 10 percent by mole or more, preferably 20 percent by mole or more, more preferably 30 percent by mole or more, and further preferably 50 percent by mole or more.

[Preservation Method]

Regarding the preservation of, in particular, tetracarboxylic dianhydride among the tetracarboxylic anhydrides according to the present invention, it is desirable that the preservation is conducted at low temperatures avoiding high humidity in order to prevent ring cleavage of the acid anhydride ring because of hydrolysis. Specifically, it is possible to endure a long term of preservation by conducting the preservation with a highly sealed container in a refrigerator.

The tetracarboxylic acid according to the present invention can be preserved at room temperature for the long term without particularly controlling the humidity.

[Method for Producing Polyimide Precursor]

The method for producing a polyimide precursor represented by the above-described general formula (5) or (6) according to the present invention is not specifically limited, and known methods can be applied. Usually, the polyimide precursor can easily be produced by reacting substantially equal mole of diamines and tetracarboxylic acid compounds according to the present invention in a polymerization solvent. At this time, it is preferable that a compound represented by the above-described general formula (1) or (2) (where $R^1$ and $R^2$ form an acid anhydride (—C(O)OC(O)—) and $R^3$ and $R^4$ form another acid anhydride) is used as a tetracarboxylic dianhydride. At that time, different acid dianhydride represented by the general formula (1) or (2) may be used as a mixture. A mixture of an acid dianhydride represented by the general formula (1) or (2) and an acid dianhydride represented by the general formula (1) or (2) where n=0 may be used.

Furthermore, compounds represented by any one of the following general formulae (9) to (12) derived from the above-described general formula (1) and compounds represented by any one of the following general formulae (13) to (16) derived from the above-described general formula (2) can be used as the tetracarboxylic acids.

[Chemical formula 27]

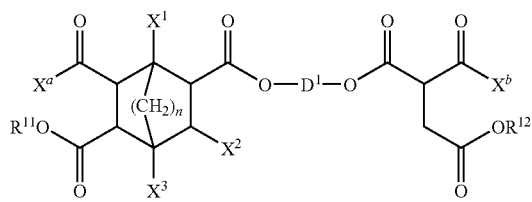

(9)

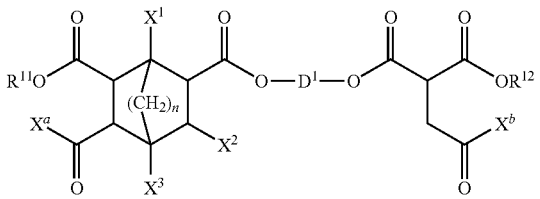

(10)

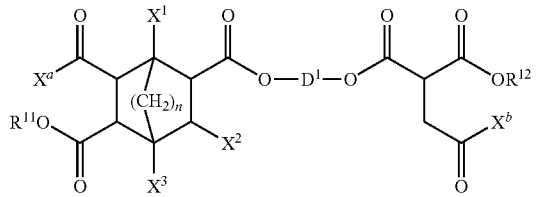

(11)

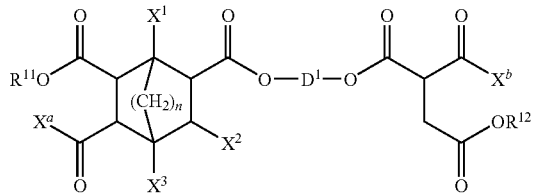

(12)

[Chemical formula 28]

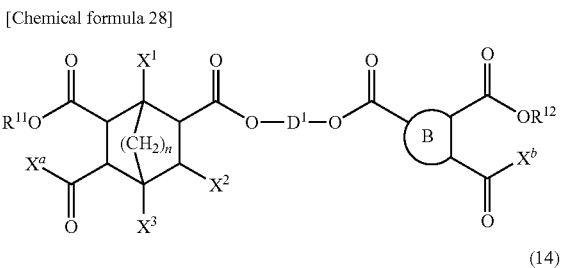

(13)

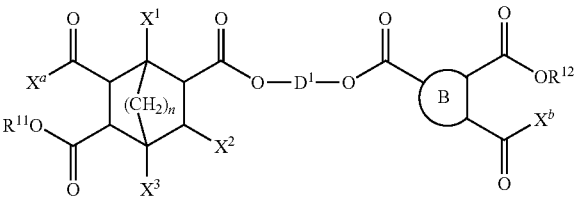

(14)

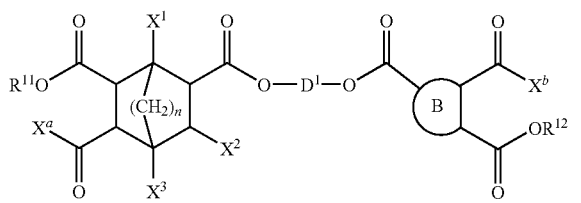

(15)

-continued (16)

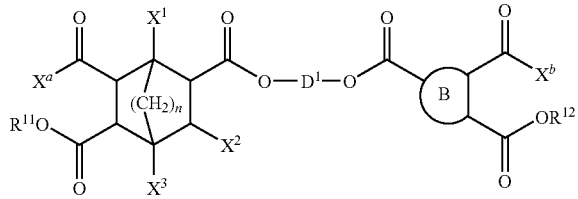

In the above-described general formulae (9) to (16), $R^{11}$ and $R^{12}$ represent independently an alkyl group having the carbon number of 1 to 12, and $X^a$ and $X^b$ represent independently a hydroxyl group or a halogen atom (any one of fluorine, chlorine, bromine, and iodine). $D^1$, B, $X^1$, $X^2$, $X^3$ and n are the same as those in the above-described general formulae (1) and (2).

Regarding the structure in which $D^1$, B, $X^a$, $X^b$, $R^{11}$, $R^{12}$, and n, and $X^1$, $X^2$, and $X^3$ are in preferable combination, D is a group having a circular structure, B is a circular structure including a cross-linking structure, $X^a$ and $X^b$ are a chlorine atom or a bromine atom, $R^{11}$ and $R^{12}$ are an alkyl group having the carbon number of 6 or less, n is 1, and $X^1$, $X^2$, and $X^3$ are independently composed of a halogen atom or a hydrogen atom. More preferably, $D^1$ is a group having a circular structure, B is a norbornane ring, $X^a$ and $X^b$ are a chlorine atom, $R^{11}$ and $R^{12}$ are a methyl group, and all $X^1$, $X^2$, $X^3$ are composed of a hydrogen atom.

The compounds represented by the above-described general formulae (9) to (16) can be synthesized as dicarboxylic acid dialkyl esters by reacting the compound represented by the above-described general formula (1) or (2) with alcohols dehydrated in advance so as to cleave an acid anhydride ring (where $X^a = X^b = OH$). At this time, products are usually obtained as a mixture of the compounds represented by the general formulae (9) to (12) or the general formulae (13) to (16). Furthermore, acid chlorides can be synthesized by chlorinating a carboxylic acid site generated through cleavage of an acid anhydride ring with a chlorination agent, e.g., thionyl chloride (where $X^a = X^b = Cl$).

The mixtures of the compounds represented by the general formulae (9) to (12) or the compounds represented by the general formulae (13) to (16) can be used for polymerization of the polyimide precursor according to the present invention. However, there is no harm in using each of isolated compounds. The use of the mixture do not exert an influence on the properties after the imidization.

The diamine used for producing the polyimide precursor according to the present invention can be selected freely within the bounds of not significantly impairing the polymerization reactivity in the production of the precursor and the characteristics required of the resulting polyimide. Specific examples of usable diamines include aromatic diamines, e.g., 3,5-diaminobenzotrifluoride, 2,5-diaminobenzotrifluoride, 3,3'-bistrifluoromethyl-4,4'-diaminobiphenyl, 3,3'-bistrifluoromethyl-5,5'-diaminobiphenyl, bis(trifluoromethyl)-4,4'-diaminodiphenyl, bis(fluorinated alkyl)-4,4'-diaminodiphenyl, dichloro-4,4'-diaminodiphenyl, dibromo-4,4'-diaminodiphenyl, bis(fluorinated alkoxy)-4,4'-diaminodiphenyl, diphenyl-,4,4'-diaminodiphenyl, 4,4'bis(4-aminotetrafluorophenoxy)tetrafluorobenzene, 4,4'-bis(4-aminotetrafluorophexy)octafluorobiphenyl, 4,4'-binaphthylamine, o-,m-,p-phenylenediamine, 2,4-diaminotoluene, 2,5-diaminotoluene, 2,4-diaminoxylene, 2,4-diaminodurene, dimethyl-4,4'-diaminodiphenyl, dialkyl-4,4'-diaminodiphenyl, dimethoxy-4,4'-diaminodiphenyl, diethoxy-4,4'-diaminodiphenyl, 4,4'-diaminodiphenylmethane, 4,4'-diaminodiphenyl ether, 3,4'-diaminodiphenyl ether, 4,4'-diaminodiphenylsulfone, 3,3'-diaminodiphenylsulfone, 4,4'-diaminobenzophenone, 3,3'-diaminobenzophenone, 1,3-bis(3-aminophenoxy)benzene, 1,3-bis(4-aminophenoxy)benzene, 1,4-bis(4-aminophenoxy)benzene, 4,4'-bis(4-aminophenoxy)biphenyl, bis(4-(3-aminophenoxy)phenyl)sulfone, bis(4-(4-aminophenoxy)phenyl)sulfone, 2,2-bis(4-(4-aminophenoxy)phenyl)propane, 2,2-bis(4-(4-aminophenoxy)phenyl)hexafluoropropane, 2,2-bis(4-(3-aminophenoxy)phenyl)propane, 2,2-bis(4-(3-aminophenoxy)phenyl)hexafluoropropane, 2,2-bis(4-(4-amino-2-trifluoromethylphenoxy)phenyl) hexafluoropropane, 2,2-bis(4-(3-amino-5-trifluoromethylphenoxy)phenyl)hexafluoropropane, 2,2-bis(4-aminophenyl)hexafluoropropane, 2,2-bis(3-aminophenyl)hexafluoropropane, 2,2-bis(3-amino-4-hydroxyphenyl)hexafluoropropane, 2,2-bis(3-amino-4-methylphenyl)hexafluoropropane, 4,4'-bis(4-aminophenoxy)octafluorobiphenyl, and 4,4'-diaminobenzanilide. At least two types thereof can also be used in combination.

Examples of aliphatic diamines include 4,4'-methylenebis (cyclohexylamine), isophoronediamine, trans-1,4-diaminocyclohexane, cis-1,4-diaminocyclohexane, 1,4-cyclohexanebis(methylamine), 2,5-bis(aminomethyl)bicyclo[2.2.1] heptane, 2,6-bis(aminomethyl)bicyclo[2.2.1]heptane, 3,8-bis(aminomethyl)tricyclo[5.2.1.0]decane, 1,3-diaminoadamantane, 2,2-bis(4-aminocyclohexyl)propane, 2,2-bis(4-aminocyclohexyl)hexafluoropropane, 1,3-propanediamine, 1,4-tetramethylenediamine, 1,5-pentamethylenediamine, 1,6-hexamethylenediamine, 1,7-heptamethylenediamine, 1,8-octamethylenediamine, and 1,9-nonamethylenediamine. At least two types thereof can be used in combination, and they can be used together with the above-described aromatic diamines.

Furthermore, siloxane-containing diamines, e.g., 1,3-bis (3-aminopropyl)-1,1,3,3-tetramethyldisiloxane, can also be used.

Among these diamines, single core phenyldiamine compounds, e.g., o-,m-,p-phenylenediamine; and diaminodiphenyl compounds, e.g., 4,4'-diaminodiphenyl, 4,4'-diaminodiphenylsulfone, 4,4'-diaminodiphenylmethane, and 4,4'-diaminodiphenyl ether, are preferable as aromatic diamine. Most of all, p-phenylenediamine, 4,4'-diaminodiphenyl ether, and 4,4'-diaminodiphenyl are more preferable because of ease of availability and good properties of the resulting resins. As for aliphatic diamines, alicyclic diamines, e.g., 4,4'-methylenebis(cyclohexylamine), trans-1,4-diaminocyclohexane, and isophoronediamine are more preferable because of a ring structure and ease of availability. Furthermore, trans-1,4-diaminocyclohexane is more preferable because of good properties of the resulting resins.

These diamines may be refined before being subjected to the reaction. As for the refining method, recrystallization, sublimation, an activated carbon treatment, distillation, and the like can be conducted at will. These refining methods can be repeated, and also be conducted in combination.

It is preferable that the purities of these diamines are high because polymerization activity is enhanced. The purities of commonly used diamines are 95% or more, preferably 97% or more, and more preferably 99% or more.

The polyimide precursor according to the present invention can be obtained by polymerizing tetracarboxylic dianhydride represented by the above-described general formula (1) or (2)

and substantially equal mole of diamine. More specifically, production can be conducted by the following method.

The reaction is conducted by mixing the diamine and the tetracarboxylic dianhydride represented by the general formula (1) or (2) in the presence of a solvent.

At this time, preferably, the ratio of usage of the tetracarboxylic dianhydride to the diamine is 1:0.8 to 1.2 in terms of molar ratio. As in the common polycondensation reaction, the molecular weight of the resulting polyamic acid increases as this molar ratio approaches 1:1.

The method for charging the diamine and the acid anhydride into a reactor can be selected at will. Examples of applicable methods include a method in which a diamine is dissolved in a solvent, and a powder of tetracarboxylic dianhydride represented by the general formula (1) or (2) is slowly added thereto, a method in which, conversely, a diamine is slowly added to a solution of tetracarboxylic dianhydride, and furthermore a method in which a diamine and a powder of tetracarboxylic dianhydride are added simultaneously to a reactor in which a solvent has been charged in advance. Most of all, the method in which a diamine is dissolved in a solvent, and a powder of tetracarboxylic dianhydride is slowly added thereto is favorably adopted because of the solubility of the reagents in the solvent.

If the reaction temperature is too low, unfavorably, the solubility of the reagent is reduced and a sufficient reaction speed cannot be obtained. If the reaction temperature is too high, unfavorably, it becomes difficult to control the proceeding of the reaction. The adopted lower limit is −20° C., preferably −10° C., and more preferably 0° C. The adopted upper limit is 150° C., preferably 100° C., and more preferably 60° C.

The reaction time adopted is not specifically limited. However, in order to achieve a sufficient conversion factor of the reagent, the lower limit is 10 minutes, preferably 30 minutes, and more preferably 1 hour. The upper limit is not particularly specified. It is not necessary to excessively extend the reaction time insofar as the reaction is completed. For example, the adopted upper limit is 100 hours, preferably 50 hours, and more preferably 30 hours.

The polymerization reaction is conducted by using a solvent. Regarding the solvent used at this time, there is no problem insofar as a diamine and a tetracarboxylic dianhydride represented by the general formula (1) or (2), which are raw material monomers, do not react with the solvent and these raw materials dissolve in the solvent. Therefore, the structure of the solvent is not specifically limited. Specific examples of favorably adopted solvents include amide solvents, e.g., N,N-dimethylformamide, N,N-dimethylacetamide, and N-methylpyrrolidone; circular ester solvents, e.g., γ-butyrolactone, γ-valerolactone, δ-valerolactone, γ-caprolactone, ∈-caprolactone, and α-methyl-γ-butyrolactone; carbonate solvents, e.g., ethylene carbonate and propylene carbonate; lactam solvents, e.g., caprolactam; ether solvents, e.g., dioxane; glycol solvents, e.g., triethylene glycol; phenol solvents, e.g., m-cresol, p-cresol, 3-chlorophenol, 4-chlorophenol, 4-methoxyphenol, and 2,6-dimethylphenol; acetophenone; 1,3-dimethyl-2-imidazolidinone; sulfolane; dimethylsulfoxide; and tetramethylurea. Furthermore, other general organic solvents, i.e. phenol, o-cresol, butyl acetate, ethyl acetate, isobutyl acetate, propylene glycol methyl acetate, ethylcellosolve, butylcellosolve, 2-methylcellosolve acetate, ethylcellosolve acetate, butylcellosolve acetate, tetrahydrofuran, dimethoxyethane, diethoxyethane, dibutyl ether, diethylene glycol dimethyl ether, methyl isobutyl ketone, diisobutyl ketone, cyclohexanone, methyl ethyl ketone, acetone, butanol, ethanol, xylene, toluene, chlorobenzene, terpene, mineral spirit, and petroleum naphtha solvent, can be added and used. Most of all, aprotic solvents, e.g., N,N-dimethylformamide, N,N-dimethylacetamide, N-methyl-2-pyrrolidone, dimethylsulfoxide, and γ-butyrolactone, are preferable because the solubility of the raw materials is high.

Regarding the usage of the solvent, preferably, the solvent is used in an amount suitable for controlling the total weight concentration of the tetracarboxylic dianhydride and the diamine, which are the raw materials, within the following range. That is, the lower limit of this concentration is 0.1 percent by weight, preferably 1 percent by weight, and more preferably 5 percent by weight. The upper limit is not specifically limited. However, from the viewpoint of the solubility of the tetracarboxylic dianhydride, 80 percent by weight, preferably 50 percent by weight, and more preferably 30 percent by weight are adopted. The polymerization is conducted within the above-described concentration and, thereby, a homogeneous solution of polyimide precursor with a high degree of polymerization can be obtained.

In order to provide the polyimide with the film toughness, it is preferable that the degree of polymerization of the polyimide precursor is as high as possible. If polymerization is conducted at a concentration lower than the above-described concentration range, a satisfactory degree of polymerization of the polyimide precursor cannot be obtained, and a finally obtained polyimide film may become fragile unfavorably. Particularly in the case where an alicyclic diamine is used as the diamine, if the concentration becomes higher, a long polymerization time may be required until formed salts are dissolved and eliminated and, thereby, the productivity may be reduced.

In this reaction, inorganic salts may be used as the catalyst, if necessary. Examples of inorganic salts used at this time include halogenated alkali metal salts, e.g., LiCl, NaCl, and LiBr; halogenated alkaline earth metals, e.g., $CaCl_2$, and halogenated metals, e.g., $ZnCl_2$. Among them, metal chlorides, e.g., LiCl, $CaCl_2$, and $ZnCl_2$, are particularly preferable.

Preferably, agitation is conducted while the reaction proceeds.

Regarding the weight average molecular weight of the thus obtained polyimide precursor according to the present invention, the lower limit is 3,000, and preferably 5,000. The upper limit is 150,000, and preferably 100,000. The molecular weight can be measured by, for example, gel permeation chromatography.

The logarithmic viscosity of the resulting polyimide precursor is not specifically limited. However, regarding the preferable logarithmic viscosity, the lower limit is 0.3 dL/g, preferably 0.5 dL/g, and more preferably 0.7 dL/g. On the other hand, the upper limit is 5.0 dL/g, preferably 3.0 dL/g, and more preferably 2.0 dL/g. The logarithmic viscosity can be measured by using, for example, an Ostward viscometer.

Foreign matter particles contained in the solution can be removed by filtrating the solution of the polyimide precursor obtained by the reaction. The removal of foreign matter particles is important particularly in the case where the resulting resin is used for optical purposes. Regarding the amount of foreign matters in the polyimide precursor according to the present invention, the number of insoluble fine particles having projected area equivalent circle diameters of 5 to 20 μm is usually 5,000 or less per kilogram of precursor, preferably 3,000 or less, and more preferably 1,000 or less. For example, the number of foreign matters can be counted by a microscope method in which the sizes and the number of insoluble fine particles are measured on an image of an microscope. Specifically, the measurement can be conducted easily by using, for example, a particle diameter image processing apparatus, e.g., XV-1000 produced by KEYENCE CORPORATION.

The polyimide precursor according to the present invention can also be synthesized from a diacid halide of dialkyl ester of the corresponding tetracarboxylic acid and a diamine through low temperature solution polycondensation following a known method (for example, a method described in High Performance Polymers, 10, 11 (1998)). Specifically, the reaction of the diamines and the tetracarboxylic acid derivatives represented by the above-described general formulae (9) to (16) ($X^a=X^b=$a halogen atom) is conducted in the presence of a solvent.

The method for charging the diamines and the tetracarboxylic acid derivatives represented by the above-described general formulae (9) to (16) (hereafter referred to as tetracarboxylic acid derivatives (9) to (16)) into a reactor can be selected at will. Examples of applicable methods include a method in which a diamine is dissolved in a solvent, and a tetracarboxylic acid derivative is slowly added thereto, a method in which, conversely, a diamine is slowly added to a solution of tetracarboxylic acid derivative, and furthermore a method in which a diamine and a tetracarboxylic acid derivative are added simultaneously to a reactor in which a solvent has been charged in advance. Most of all, the method in which a diamine is dissolved in a solvent, and a tetracarboxylic acid derivative is slowly added thereto is favorably adopted because of ease of reaction control.

If the reaction temperature is too low, unfavorably, the solubility of the reagent is reduced and a sufficient reaction speed cannot be obtained. If the reaction temperature is too high, unfavorably, it becomes difficult to control the proceeding of the reaction. Regarding the reaction temperature adopted, the low limit is −20° C., preferably −10° C., and more preferably 0° C. The upper limit is 150° C., preferably 100° C., and more preferably 80° C.

The reaction time adopted is not specifically limited. However, the adopted lower limit is 10 minutes, preferably 30 minutes, and more preferably 1 hour. The upper limit is not particularly specified. However, the adopted upper limit is 150 hours, preferably 100 hours, and preferably 50 hours.

This polymerization reaction is conducted by using a solvent. Regarding the solvent used at this time, the solvent used for the above-described reaction of the diamine and the tetracarboxylic dianhydride can be used.

Regarding the usage of the solvent, preferably, the solvent is used in an amount suitable for controlling the total weight concentration of the tetracarboxylic acid derivatives (9) to (16) and the diamines, which are the raw materials, within the following range. That is, the lower limit of this concentration is 0.1 percent by weight, preferably 1 percent by weight, and more preferably 5 percent by weight. The upper limit is not specifically limited. However, from the viewpoint of the solubility of the tetracarboxylic acid derivative, 80 percent by weight, preferably 50 percent by weight, and more preferably 30 percent by weight are adopted.

In this reaction, the basic substance may be used. The basic substances usable here are tertiary amines and inorganic basic substances. Specifically, aromatic tertiary amines, e.g., pyridine; aliphatic tertiary amines, e.g., triethylamine and N-methylpiperidine; and inorganic basic substances, e.g., potassium carbonate, sodium carbonate, and sodium salts and sodium hydrogen salts of phosphorus, can be used. Most of all, pyridine and triethylamine are preferable because of ease of availability and the operability. It is preferable that these basic substances are added in advance by being dissolved in a solvent to be used in the reaction. The usage of the basic substance can be changed at will in accordance with the amount of acid contained in the tetracarboxylic acid derivatives (9) to (16). As a matter of course, the basic substance may not be used in the case where there is no acid generated by the reaction in the tetracarboxylic acid derivative. Regarding the usage of basic substance in the case where an acid is generated, the lower limit of the number of moles is 2 times the number of moles of the tetracarboxylic acid derivative used for the polymerization, and preferably 3 times. The upper limit is 10 times, and preferably 5 times.

Preferably, agitation is conducted while the reaction proceeds.

The polymerization reaction between the diamines and the tetracarboxylic acid derivatives (9) to (16) can also be conducted by an interfacial polycondensation method. The interfacial polycondensation method is characterized by a solvent to be used. That is, the diamines dissolve in an aqueous solution in which the basic substance, e.g., a tertiary amine, has been dissolved. On the other hand, the tetracarboxylic acid derivatives (9) to (16) (in the case where $X^a=X^b=$a chlorine atom) dissolve in nonpolar organic solvents insoluble in water. Examples of nonpolar organic solvents used at this time include aromatic solvents, e.g., toluene and xylene, and aliphatic hydrocarbon solvents, e.g., cyclohexane, hexane, and heptane.

In the case where the polymerization reaction is conducted by the interfacial polycondensation method, these two solutions are mixed and agitated vigorously, so that a polyimide precursor can be obtained. At this time, there is no harm even when the amounts of charge of diamine and tetracarboxylic acid derivative are not equal moles.

Furthermore, the polyimide precursor according to the present invention can be produced by using the tetracarboxylic acid derivatives (9) to (16) (in the case where $X^a=X^b=$a hydroxyl group) and equal mole of diamine in the presence of a condensation agent. For example, it is also possible to conduct polycondensation directly in the presence of pyridine by using triphenyl phosphite which serves as the condensation agent and the number of moles of which is equal to the diamine. Likewise, polycondensation can be conducted directly by using N,N-dicyclohexylcarbodiimide as another condensation agent.

The production of the polyimide precursor according to the present invention can also be conducted by subjecting disilylated diamine and the tetracarboxylic dianhydride represented by the formula (1) or (2) or the tetracarboxylic acid derivatives (9) to (16) (in the case where $X^a=X^b=$a chlorine atom) to the low temperature solution polycondensation, as in the above description, following the known method (the Symposium on Macromolecules Preprints, 49, 1917 (2000)).

In the production of the polyimide according to the present invention, in addition to the tetracarboxylic acid compound according to the present invention, another acid dianhydride or tetracarboxylic acid may be mixed and copolymerized with the diamine. The acid dianhydride usable at that time is not specifically limited. Examples thereof include aromatic acid dianhydrides having one benzene ring, e.g., pyromellitic acid; aromatic acid dianhydrides having two benzene rings, e.g., 3,3',4,4'-biphenyltetracarboxylic dianhydride (BPDA), 2,3',3,4'-biphenyltetracarboxylic dianhydride (a-BPDA), 3,3',4,4'-diphenylsulfonetetracarboxylic dianhydride (DSDA), 3,3',4,4'-benzophenonetetracarboxylic dianhydride (BTDA), 2,2',3,3'-benzophenonetetracarboxylic dianhydride, 3,3',4,4'-oxydiphthalic anhydride (ODPA), bis(2,3-dicarboxyphenyl)ether dianhydride (a-ODPA), bis(3,4-dicarboxyphenyl)ether dianhydride, bis(3,4-dicarboxyphenyl) methane dianhydride, 2,2'-bis(3,4-dicarboxyphenyl)propane dianhydride (BDCP), 2,2'-bis(2,3-dicarboxyphenyl)propane dianhydride, 2,2'-bis(3,4-dicarboxyphenyl)hexafluoropropane dianhydride (BDCF), and 2,2'-bis(2,3-dicarboxyphenyl)hexafluoropropane dianhydride; aromatic acid dianhydrides having a naphthalene skeleton, e.g., 2,3,6,7-naphthalenetetracarboxylic dianhydride, 1,2,5,6-naphthalenetetracarboxylic dianhydride, and 1,4,5,8-naphthalenetetracarboxylic dianhydride; and aromatic acid dianhydrides having an anthracene skeleton, e.g., 2,3,6,7-anthracenetetracarboxylic dianhydride and 1,2,5,6-anthracenetetracarboxylic dianhydride.

On the other hand, examples of alicyclic acid anhydrides usable additionally can include chain aliphatic tetracarboxylic dianhydrides, e.g., 1,2,3,4-butanetetracarboxylic dianhydride and ethylene tetracarboxylic dianhydride; and dianhydrides of tetracarboxylic acid having an alicyclic structure, e.g., 1,2,3,4-cyclobutanetetracarboxylic dianhydride, 1,3-dimethyl-1,2,3,4-cyclobutanetetracarboxylic dianhydride, 1,2,4,5-cyclopentanetetracarboxylic dianhydride, 1,2,3,4-cyclopentanetetracarboxylic dianhydride, 1,2,4,5-cyclohexanetetracarboxylic dianhydride, bicyclo[2.2.2]oct-7-ene-2,3,5,6-tetracarboxylic dianhydride, dicyclohexyl-3,4,3',4'-tetracarboxylic dianhydride (hydrogenated BPDA), 2,3,5-tricarboxycyclopentylacetic dianhydride, 3,4-dicarboxy-1,2,3,4-tetrahydro-1-naphthalenesuccinic dianhydride, and bicyclo[3,3,0]octane-2,4,6,8-tetracarboxylic dianhydride.

The ratio of usage of acid dianhydride to the tetracarboxylic acid compound according to the present invention can be set at will in accordance with the properties of the resin to be obtained. However, the usage of the tetracarboxylic acid compound according to the present invention is preferably 5 percent by mole or more, and it is more preferable that the usage is 10 percent by mole or more.

The polyimide precursor in a solution state can be isolated, if necessary. For example, the solution of the polyimide precursor is added to a poor solvent, e.g., water, methanol, or acetone, so as to precipitate the polyimide precursor. The solvent is removed by drying or the like from a solid obtained by filtration or the like, so that the polyimide precursor can be isolated as a powder. If necessary, the resulting powder is dissolved in the above-described reaction solvent or the like so as to come into a solution again. It is also possible to refine the polyimide precursor according to the present invention by repeating this operation.

[Method for Producing Polymer According to the Present Invention (Imidization Reaction)]

Examples of methods for synthesizing a polymer containing the structure represented by the above-described general formula (7) as at least a part thereof include (i) a method for obtaining the polymer from the polyimide precursor and (ii) a method for obtaining the polymer not through the polyimide precursor. As for (i) the method for obtaining the polymer from the polyimide precursor, there are a heating imidization method and a chemical imidization method. However, the method for producing the polymer according to the present invention is not specifically limited to the methods described below.

(i) Method for Obtaining Polymer from Polyimide Precursor

The polymer containing the structure represented by the above-described general formula (7) as at least a part thereof can be produced by subjecting the polyimide precursor according to the present invention and obtained by the above-described method to a cyclization and imidization reaction.

At this time, the polymer containing the structure represented by the general formula (7) as at least a part thereof can be made into the form of a film, a powder, a compact, or a solution.

The film of the polymer containing the structure represented by the above-described general formula (7) as at least a part thereof can be produced as described below, for example.

A polymerization solution (varnish) of the above-described polyimide precursor is applied by being spread on a substrate, e.g., glass, copper, aluminum, silicon, a quartz plate, a stainless steel sheet, and a kapton film. Examples of application methods include a method in which the polyimide solution obtained as described above is dropped on the above-described substrate, the solution is extended by scraping on a support or the like with a fixed height and, thereby, the solution with a uniform height is applied. At this time, apparatuses, e.g., a doctor blade, may be used. Other application methods, e.g., a spin coating method, a printing method, and an ink-jet method, can be adopted without limitation insofar as the solution having a predetermined thickness can be applied.

A solvent is used in the application of the polyimide precursor on the substrate. The viscosity is adjusted to fit the application by adjusting the usage of the solvent. The lower limit of the viscosity at that time is 1 poise, and preferably 5 poises. The upper limit is 100 poises, and preferably 80 poises.

Since the solvent is contained in the coating film applied as described above, drying is conducted. Regarding the drying temperature adopted at that time, the lower limit is usually 20° C., preferably 40° C., and more preferably 60° C. On the other hand, the upper limit is usually 200° C., preferably 150° C., and more preferably 100° C.

The drying time adopted is not specifically limited insofar as the solvent is removed to some extent. However, the lower limit is usually 10 minutes, preferably 30 minutes, and more preferably 1 hour. The upper limit is not particularly specified. However, the adopted upper limit is usually 50 hours, preferably 30 hours, and more preferably 10 hours.

The drying may be conducted under reduced pressure. The degree of the reduced pressure adopted at that time is usually 0.05 MPa or less, preferably 0.01 MPa or less, and more preferably 0.001 MPa or less.

The amount of remaining solvent after the drying is usually 70 percent by weight or less, preferably 50 percent by weight or less, and more preferably 30 percent by weight or less.

The thus obtained dried polyimide precursor film on the substrate is heated at high temperatures in a vacuum, in an inert gas, e.g., nitrogen, or in the air so as to imidize. This method is referred to as heat-imidization.

Regarding the heating temperature adopted at this time, the lower limit is usually 180° C., preferably 200° C., and more preferably 250° C. On the other hand, the upper limit is usually 500° C., preferably 400° C., and more preferably 350° C. If the heating temperature is 180° C. or lower, unfavorably, cyclization reaction of the cyclization and imidization reaction may become insufficient. If the heating temperature is too high, the resulting polyimide film may be colored unfavorably.

It is desirable that the imidization is conducted in a vacuum or in an inert gas. However, there is no harm in conducting in the air unless the temperature of the imidization is too high.

The degree of the reduced pressure adopted in the case where the heat-imidization is conducted under reduced pressure is usually 0.05 MPa or less, preferably 0.01 MPa or less, and more preferably 0.001 MPa or less.

As for the heating time, the time required for sufficient proceeding of the cyclization and imidization is adopted. The lower limit is usually 5 minutes, preferably 10 minutes, and more preferably 20 minutes. The upper limit is not particularly specified. However, the adopted upper limit is usually 20 hours, preferably 10 hours, and more preferably 5 hours.

It is also possible to conduct chemical imidization by immersing the polyimide precursor film in a solution containing a dehydration reagent. Preferably, this reaction is conducted in the presence of a tertiary amine. Examples of tertiary amines usable at this time include aromatic tertiary amines, e.g., pyridine, and aliphatic tertiary amines, e.g., triethylamine and N-methylpiperidine. Among them, pyridine and triethylamine are preferable because of ease of availability and good reactivity.

Regarding the usage of tertiary amine, the lower limit of the number of moles is usually 0.1 times the number of moles of the amic group contained in the polyimide precursor, preferably 0.5 times, and more preferably 1.0 time. The lower limit is usually 30 times, preferably 20 times, and more preferably 10 times.

Examples of usable dehydration reagents include acid anhydrides, e.g., acetic anhydride, propionic anhydride, and trifluoromethanesulfonic anhydride, and carbodiimides, e.g., N,N-dicyclohexylcarbodiimide. Among them, acetic anhydride, trifluoromethanesulfonic anhydride, and carbodiimides, e.g., N,N-dicyclohexylcarbodiimide, are preferable. Furthermore, acetic anhydride is more preferable from the viewpoint of ease of availability and economic efficiency.

Regarding the usage of dehydration reagent used at that time, the lower limit of the number of moles is usually 1.0 time the number of moles of the amic group contained in the polyimide precursor, preferably 2.0 times, and more preferably 4.0 times. The upper limit is not particularly specified. However, the upper limit is usually 50 times, preferably 30 times, and more preferably 20 times. The treatment with these dehydration reagents may be conducted at room temperature. In the case where the proceeding of the reaction is slow, heating may be conducted for the use.

As described above, it is preferable that the heating or the dehydration reagent are used in the cyclization and imidization reaction. However, the reaction can also be conducted by using heating and the dehydration reagent in combination.

Regarding another form of the heat-imidization, the solution (varnish) of the polymer, according to the present invention, containing the structure represented by the above-described general formula (7) as at least a part thereof can easily be produced by heating the polymerization solution of the polyimide precursor according to the present invention without treating the polymerization solution or in a solution after the polymerization solution is diluted with the same solvent appropriately.

The concentration of the solution in the heat-imidization is not specifically limited. However, the lower limit is usually 1 percent by weight in terms of polyimide precursor according to the present invention, preferably 5 percent by weight, and more preferably 10 percent by weight. The upper limit is usually 80 percent by weight, preferably 60 percent by weight, and more preferably 50 percent by weight.

Regarding the heating temperature at this time, the lower limit is usually 100° C., preferably 120° C., and more preferably 150° C. On the other hand, the upper limit can be set at will insofar as the desired product is not colored at that temperature. The upper limit is usually 300° C., preferably 250° C., and more preferably 200° C.

At this time, in order to remove water and the like, which are byproducts of the cyclization and imidization reaction, by azeotropic distillation, an azeotropic solvent, e.g., toluene or xylene, may be added and the reaction may be conducted while generated water is removed together with the solvent by distillation.

The reaction may be conducted after a basic substance is added as a catalyst of the cyclization and imidization reaction. Examples of base catalysts usable in the present invention can include aromatic amines, e.g., pyridine, γ-picoline, and pyrazine.

Furthermore, chemical imidization can be conducted by adding a dehydration reagent to a solution of the polyimide precursor. This reaction is usually conducted in the presence of the dehydration reagent and the basic substance.

Examples of dehydration reagents usable in the chemical imidization include acid anhydrides of lower carboxylic acids, e.g., acetic anhydride and trifluoroacetic anhydride; anhydrides of aromatic dicarboxylic acids, e.g., trimellitic anhydride and pyromellitic anhydride; and alkylcarbodiimides, e.g., N,N-dicyclohexylcarbodiimide. Regarding the usage thereof, the lower limit of the number of moles is usually 1.0 time the number of moles of the amic group contained in the polyimide precursor, preferably 2.0 times, and more preferably 4.0 times. The upper limit is not particularly specified. However, the upper limit is usually 50 times on a mole basis, preferably 30 times, and more preferably 20 times. If the usage of dehydration reagent is too small, a problem occurs in that the proceeding of the reaction becomes slow. If the usage is too large, the dehydration reagent remains in the desired product.

On the other hand, the type of usable basic substance is not specifically limited. Organic tertiary amines, e.g., pyridine, triethylamine, tributylamine, N,N-dimethylaniline, and dimethylaminopyridine, and inorganic basic substances, e.g., potassium carbonate and sodium carbonate, can be used. Most of all, pyridine and triethylamine are preferable from the viewpoint that they can be available inexpensively and the reaction operation becomes easy because of liquid and good solubility.

Regarding the usage of the basic substance, the lower limit of the number of moles is usually 0.1 time the number of moles of the amic group contained in the polyimide precursor, preferably 0.5 times, and more preferably 1.0 time. The upper limit is usually 30 times on a mole basis, preferably 20 times, and more preferably 10 times. If the usage of basic substance is too small, a problem occurs in that the proceeding of the reaction becomes slow. If the usage is too large, the basic substance remains in the desired product.

As for the reaction solvent, the solvents used in the above-described synthesis of the polyimide precursor can be used.

Regarding the reaction temperature adopted, the low limit is usually −10° C., preferably −5° C., and more preferably 0° C. The upper limit is usually 80° C., preferably 60° C., and more preferably 40° C.

The lower limit of the reaction time is usually 5 minutes, and preferably 10 minutes. The upper limit is not particularly specified. However, the upper limit is usually 100 hours, and preferably 24 hours.

The reaction is usually conducted at normal pressure. If necessary, the reaction can be conducted under pressure or under reduced pressure.

The reaction atmosphere is usually a nitrogen atmosphere.

The imidization factor by this imidization reaction can be controlled by adjusting the amount of catalyst, the reaction temperature, and the reaction time.

The polymer which is obtained by the above-described method and which contains the structure represented by the general formula (7) as at least a part thereof is made into a solution. A reagent, e.g., benzoyl chloride or acetic anhydride and pyridine, is added to the resulting solution or the solution obtained by the reaction and, thereby, terminal amide groups can be protected as amide groups. Consequently, coloring of the polyimide can be prevented and the stability is improved favorably.

In the method in which imidization is conducted in the presence of the dehydration reagent and the basic substance in the above-described manner, polyisoimide which is an isomer of polyimide may be incorporated. The ratio of incorporation of the polyisoimide is usually 50% or more, and preferably 80% or more. The polyimide incorporated with the polyisoimide is made into a powder or is made into a film by being dissolved into the solvent again and being applied to a substrate or the like. Thereafter, heating is conducted and, thereby, the incorporated polyisoimide can be isomerized to a polyimide.

Regarding the temperature at this time, the lower limit of usually 100° C., preferably 200° C., and more preferably 300° C. can be adopted. On the other hand, the upper limit of usually 500° C., preferably 400° C., and more preferably 350° C. can be adopted. Regarding the reaction time at that time, the lower limit is usually 5 minutes, and preferably 10 minutes. The upper limit is not particularly specified. However, the upper limit is usually 100 hours, and preferably 24 hours.

(ii) Method for Obtaining Polymer not Through Polyimide Precursor

As for the method for obtaining the polymer not through the polyimide precursor, there is a method in which the tetracarboxylic acid compound represented by the above-described general formula (1) or (2) is used as a raw material, and this is reacted with diamines to conduct cyclization and imidization reaction directly, so as to produce the polymer according to the present invention.

In this method, cyclization and imidization is conducted directly without isolating the polyimide precursor, which is an intermediate, in midstream. Regarding the reaction condition at that time, the above-described condition of heat-imidization for producing the polymer containing the structure represented by the general formula (7) as at least a part thereof from the polyimide precursor can be adopted appropriately.

[Method for Changing Form of Polymer According to the Present Invention]

Regarding the thus obtained polymer containing the structure represented by the above-described general formula (7) as at least a part thereof, polymers having various forms can easily be produced from a solution (varnish) prepared by dissolving the above-described polymer into a solvent.

For example, the polymer containing the structure represented by the above-described general formula (7) as at least a part thereof can be isolated as a powder by being dropped into a large amounts of poor solvent and filtrated. The poor solvent usable at this time is not specifically limited. Examples thereof can include water, methanol, acetone, hexane, butylcellosolve, heptane, methyl ethyl ketone, methyl isobutyl ketone, ethanol, toluene, and benzene. The specific polymer put into the poor solvent and precipitated is recovered by filtration and, thereafter, drying is conducted at ambient temperature or by heating under normal pressure or reduced pressure, so that a powder can be obtained.

If the operation in which the polymer converted to the powder is dissolved into the organic solvent again and is precipitated and recovered again is repeated 2 to 10 times, impurities in the polymer can be reduced. It is preferable that at least three types of poor solvent, e.g., alcohols, ketones, and hydrocarbons, are used as the poor solvent at this time because the efficiency of refining further increases.

The thus obtained powder polymer can be converted to a solution (varnish) by being dissolved into the solvent again.

As for the solvent usable at that time, the solvents used in the synthesis of the polyimide precursor can be used.

In addition to this, for the purpose of improving the uniformity of coating film, solvents having low surface tensions can also be used. Examples thereof include ethylcellosolve, butylcellosolve, ethylcarbitol, butylcarbitol, ethylcarbitol acetate, ethylene glycol, 1-methoxy-2-propanol, 1-ethoxy-2-propanol, 1-butoxy-2-propanol, 1-phenoxy-2-propanol, propylene glycol monoacetate, propylene glycol diacetate, propylene glycol-1-monomethyl ether-2-acetate, propylene glycol-1-monoethyl ether-2-acetate, dipropylene glycol, 2-(2-ethoxypropoxy)propanol, methyl lactate, ethyl lactate, n-propyl lactate, n-butyl lactate, and isoamyl lactate. These solvents may be used alone or mixtures of a plurality of types may be used.

The amount of mixing of the solvent for the purpose of improving the uniformity of coating film is preferably 10 to 80 percent by weight in the entire solvents, and more preferably 20 to 60 percent by weight. Regarding the concentration of the polymer at this time, the lower limit is usually 1 percent by weight, preferably 5 percent by weight, and more preferably 10 percent by weight. The upper limit is usually 80 percent by weight, preferably 60 percent by weight, and more preferably 50 percent by weight.

The thus obtained polyimide solution (varnish) can be used as a coating material of various materials, for film formation, and for films.

Foreign matter particles contained in the polymer can be removed by filtrating the solution of the polymer. The removal of foreign matter particles is important for optical purposes. Regarding the amount of foreign matters in the polymer, according to the present invention, containing the structure represented by the general formula (7) as at least a part thereof, the number of insoluble fine particles having projected area equivalent circle diameter of 5 to 20 μm is usually 5,000 or less per kilogram of precursor, preferably 3,000 or less, and more preferably 1,000 or less. The method for measuring the number of insoluble fine particles is as described above.

A polymer compact in a desired shape can be obtained by heat-compressing the powder of the polymer containing the structure represented by the above-described general formula (7) as at least a part thereof, according to the present invention. Regarding the heating temperature at this time, the lower limit is usually 150° C., preferably 200° C., and more preferably 250° C. On the other hand, the upper limit is usually 450° C., preferably 400° C., and more preferably 350° C. If the polymer powder once isolated is dissolved again into, for example, the solvent used in the polymerization, the powder can be returned to the vanish of the polymer containing the structure represented by the general formula (7) as at least a part thereof.

Furthermore, if this vanish of the polymer containing the structure represented by the general formula (7) as at least a part thereof is applied to a substrate and dried, a film of the polymer containing the structure represented by the general formula (7) as at least a part thereof can be formed.

In this case, the application method is not specifically limited. For example, a method in which a solution of the polymer is dropped on an optical substrate, e.g., a quartz plate, a stainless steel sheet, and a kapton film, the solution is extended by scraping on a support with a fixed height and, thereby, the solution with a uniform height is applied is mentioned. At this time, apparatuses, e.g., a doctor blade, may be used.

Examples of other application methods include a spraying method, a dip coating method, a spin coating method, a printing method, and an ink-jet method. However, a transfer printing method is industrially widely used from the viewpoint of the productivity, and this is favorably used in the present invention as well.

The thus applied polymer containing the structure represented by the general formula (7) as at least a part thereof contains still much solvent. Therefore, the solvent is removed by heating. Regarding the temperature at that time, the lower limit is usually 70° C., preferably 100° C., and more preferably 150° C. The upper limit is usually 350° C., preferably 300° C., and more preferably 250° C. Regarding the heating, the temperature may be raised stepwise, or be raised continuously.

These steps may be conducted under reduced pressure or in an inert gas atmosphere.

The degree of the reduced pressure adopted in the case where the steps are conducted under reduced pressure is usually 0.05 MPa or less, preferably 0.01 MPa or less, and more preferably 0.001 MPa or less.

If necessary, the thus obtained film can be patterned by a method of wet etching, dry etching, laser ablation, or the like, so that an optical component formed into a predetermined shape can be produced.

Optical elements, e.g., films and optical components, produced by using the thus obtained polymer, according to the present invention, containing the structure represented by the general formula (7) as at least a part thereof exhibit small birefringence and are achromatic and transparent. Therefore, the properties thereof are very good even when film thicknesses are large.

The thickness in the formation of the film of the polymer, according to the present invention, containing the structure represented by the general formula (7) as at least a part thereof can be controlled by changing the thickness of the solution applied. The lower limit is usually 0.1 µm, preferably 1 µm, and more preferably 5 µm. The upper limit is usually 1,000 µm, preferably 700 µm, and more preferably 500 µm.

The polymer, according to the present invention, containing the structure represented by the general formula (7) as at least a part thereof exhibits excellent solvent solubility. Therefore, the solution thereof can be worked into desired forms, e.g., sheets and fibers, in accordance with the uses. The film can be used in the form of not only a single layer, but also a multilayer.

The polymer, according to the present invention, containing the structure represented by the general formula (7) as at least a part thereof and the precursor thereof can be blended with additives, e.g., an oxidation stabilizer, an inorganic and/or an organic filler, a silane coupling agent, a photosensitizer, a photopolymerization initiator, a flame retardant, and a sensitizing agent, if necessary.

Furthermore, other resins can be mixed in order to achieve properties, e.g., improvement in strength, enhancement of heat resistance, and reduction in water absorption property, which are required of the resin.

The resin used at that time is not specifically limited insofar as the resin can be mixed homogeneously with the polymer, according to the present invention, containing the structure represented by the general formula (7) as at least a part thereof. Examples thereof include optical transparent resins, e.g., polyimides, polyetherimides, polyesterimides having other compositions, polyethersulfones, triacetyl cellulose, polycarbonates, polyesters, poly(meth)acrylates, and polycycloolefins.

[Properties of Polymer According to the Present Invention]

Among the resins having the above-described excellent properties, e.g., heat resistance, transparency, and absorbing property, in combination, specific properties of the polymer, according to the present invention, containing the structure represented by the general formula (7) as at least a part thereof will be described below.

Regarding the range of the glass transition temperature Tg (° C.) of this polymer, the lower limit is usually 200° C., and preferably 250° C., and the upper limit is usually 500° C., preferably 450° C., and more preferably 400° C., so that high heat resistance is exhibited.

Furthermore, 5% weight loss temperature serving as another index of heat resistance in an inert gas atmosphere is usually 350° C. or higher, preferably 400° C. or higher, and more preferably 420° C. or higher. In an air atmosphere, it is usually 350° C. or higher, preferably 380° C. or higher, and more preferably 400° C. or higher.

The features of the polymer, according to the present invention, containing the structure represented by the general formula (7) as at least a part thereof include high transparency. Regarding the transparency, in a graph of ultraviolet-visible light absorption spectrum measured by using a polyimide film having a thickness of 30 µm, an average transmittance within the wavelength range of 250 to 800 nm is usually 50% or more, preferably 60% or more, and more preferably 70% or more. The transmittance of monochromatic light of 400 nm is usually 70% or more, preferably 75% or more, more preferably 80% or more, and particularly preferably 85% or more. The cut off wavelength is usually 350 nm or less, preferably 330 nm or less, and more preferably 310 nm or less. The lower limit of the cut off wavelength is usually 220 nm, and preferably 250 nm.

As is described later in the section of EXAMPLES, the cut off wavelength can be determined by measuring the transmittance of visible-ultraviolet light with wavelengths of 200 nm to 800 nm by using Spectrophotometer for ultraviolet and visible region (UV-3100S) produced by SHIMADZU CORPORATION regarding the film having a film thickness of 30 µm and examining the wavelength (cut off wavelength) at which the transmittance becomes 0.5% or less.

The features of the polymer, according to the present invention, containing the structure represented by the general formula (7) as at least a part thereof include that excellent optical isotropy is exhibited and the birefringence is small. The birefringence is usually 0.05 or less, preferably 0.01 or less, and more preferably 0.005 or less.

The pencil hardness (JIS-K5400) of the polymer, according to the present invention, containing the structure represented by the general formula (7) as at least a part thereof is usually within the range of B to 7H, and preferably within the range of H to 4H.

Regarding the refractive index of the polymer, according to the present invention, containing the structure represented by the general formula (7) as at least a part thereof, the upper limit is usually 1.75, preferably 1.70, and more preferably 1.68. The lower limit is 1.50, preferably 1.53, and more preferably 1.55. It is well known that the refractive index is reduced by introducing fluorine atoms into a resin. Likewise, the refractive index is reduced by introducing fluorine atoms into the polymer according to the present invention. In that case, the upper limit of the refractive index is usually 1.65, preferably 1.63, and more preferably 1.60. The lower limit is usually 1.45, preferably 1.48, and more preferably 1.50.

The dielectric constant of the polymer, according to the present invention, containing the structure represented by the general formula (7) as at least a part thereof at 1 MHz is usually 3.2 or less, preferably 3.0 or less, and more preferably 2.9 or less. It is well known that the dielectric constant is reduced by introducing fluorine atoms into a resin. Likewise, the dielectric constant is reduced by introducing fluorine atoms into the polymer according to the present invention. In that case, the dielectric constant is usually 3.0 or less, preferably 2.8 or less, and more preferably 2.7 or less. Furthermore, there is a feature that within the range of 1 to 20 GHz, the dielectric loss tangent exhibits low frequency dependence and shows almost constant value within the range of 0.005 to 0.02. Therefore, very excellent high frequency characteristics are exhibited.

Regarding the amount of foreign matter particles in the polymer, according to the present invention, containing the structure represented by the general formula (7) as at least a part thereof, the number of insoluble fine particles having projected area equivalent circle diameter of 5 to 20 μm is usually 5,000 or less per kilogram of precursor, preferably 3,000 or less, and more preferably 1,000 or less, as described above.

The water absorption coefficient after the polymer, according to the present invention, containing the structure represented by the general formula (7) as at least a part thereof is immersed in water at 25° C. for 24 hours is usually 2.0 percent by weight or less, preferably 1.5 percent by weight or less, and more preferably 1.0 percent by weight or less.

As is described later in the section of EXAMPLES, a film formed having a film thickness of 30 μm is vacuum-dried at 80° C. for 3 hours, the film is immersed in water at 25° C. for 24 hours, the film is pulled up and sandwiched between dry paper (pulp 100%) having good water absorption property, followed by standing for 1 minute, so as to allow the water adhered to the film surface to soak into the paper, the paper is changed two times so as to repeat the same operation, and the weight is measured, so that the water absorption coefficient can be determined from an increment of the weight between before and after the immersion.

The coefficient of linear thermal expansion of the polymer, according to the present invention, containing the structure represented by the general formula (7) as at least a part thereof is usually 100 ppm/K or less, preferably 50 ppm/K or less, and more preferably 30 ppm/K or less.

The polymer, according to the present invention, containing the structure represented by the general formula (7) as at least a part thereof exhibits high solubility in a solvent. In particular, the polymer dissolves well into the solvent used in the above-described synthesis of the polyimide precursor and, therefore, can be converted to a solution easily.

The features of the polymer, according to the present invention, containing the structure represented by the general formula (7) as at least a part thereof include high restoration property. That is, if the above-described film is produced, the film is flexible, the film can be bent, and when the film is returned to the original state, a flat film is restored. Usually, the film of the polymer, according to the present invention, containing the structure represented by the general formula (7) as at least a part thereof can be produced to exhibit excellent flexibility in such a way that no cracking occurs even if 180 degree bending is conducted.

The tensile strength of the film formed from the polymer, according to the present invention, containing the structure represented by the general formula (7) as at least a part thereof is usually 10 MPa or more, preferably 30 MPa or more, and more preferably 50 MPa or more.

The tensile modulus of the film formed from the polymer, according to the present invention, containing the structure represented by the general formula (7) as at least a part thereof is usually 0.1 GPa or more, preferably 0.5 GPa or more, and more preferably 1.0 GPa or more.

Regarding the tensile elongation of the film formed from the polymer, according to the present invention, containing the structure represented by the general formula (7) as at least a part thereof, the lower limit is usually 0.1%, preferably 0.5% or more, and more preferably 1.0%. The upper limit is usually 100% or less, preferably 50% or less, and more preferably 30% or less.

The polymer according to the present invention satisfies a high glass transition temperature, low birefringence, achromatic transparency, low water absorption property, and low dielectric property in combination. Taking advantage of these excellent well-balanced characteristics, the polymer can be used as a material in a semiconductor field, an optical material field, an optical communication field, a display field, electric and electronic equipment fields, a transportation equipment field, an aerospace field, and the like.

For example, optical material field includes precision optical components, e.g., lenses and diffraction gratings; disk substrates, e.g., holograms, CDs, MDs, DVDs, and optical disks; and optical adhesives. Display uses include LCD substrates, polarizer support films, transparent resin sheets, retardation films, light diffusing films, prism sheets, LCD adhesives, LCD spacers, LCD electrode substrates, color filter transparent protective films, color filters, and transparent protective films. Display material uses other than the LCD include projector screens, plasma display substrates and films, optical filters, and organic EL coating materials. The optical communication field and the optical element fields include optical fibers, optical waveguides, optical dividers, optical multiplexers, optical switching elements, optical modulators, optical filters, wavelength dividers, optical amplifiers, optical attenuators, and light wavelength converters. The electric and electronic equipment fields include insulating tapes, various laminates, flexible printed circuit boards, multilayer printed circuit board adhesive films, printed circuit board cover films, semiconductor integrated circuit element surface protective films, wire coating agents, and sealing agents of optical semiconductors, e.g., flash memory, CCD, PD, and LD. The semiconductor field includes buffer coat films, passivation films, interlayer insulating films, base polymers of photosensitive polymers, semiconductor coating agents, and underfill agents. The aerospace field includes coating materials for special aerospace components, e.g., solar cells and heat control systems. In addition to them, coating materials and base film substrates of solar cells, adhesives, and other coating materials taking advantage of the characteristics of the present agent are included.

In the case where the polymer according to the present invention is applied to these uses, application can be conducted within the range of the knowledge of a person skilled in the concerned technical area. Specific examples thereof include coating of various materials; uses in the forms of single layer and multilayer films, sheets, fibers, and compacts; addition of oxidation stabilizers, fillers, silane coupling agents, photosensitizers, photopolymerization initiators, flame retardants, and sensitizing agents thereto; and mixing with other resins.

Most of all, the polymer according to the present invention can be dissolved into a solvent so that a film can be formed by application at low temperatures. Furthermore, the polymer is optically transparent and has a high light transmittance and very small birefringence, whereas other optical resins do not have such characteristic balance. Therefore, the polymer is suitable for the use as various components for liquid crystal displays. For example, the polymer can be used as a raw material resin for producing crystal display components, e.g., alignment films, adhesives, polarizers, color filters, resin black matrix materials, and viewing angle compensating films.

EXAMPLES

The present invention will be specifically described below with reference to examples.

The analysis methods adopted in the following examples are as described below.

<Infrared Absorption Spectrum>

The infrared absorption spectrum of the polyimide thin film was measured with Fourier Transform Infrared Spectrometer (FT-IR8000 produced by JASCO Corporation) by a transmission method.

<Intrinsic Viscosity>

The intrinsic viscosity of 0.5 percent by weight polyimide precursor solution was measured with Ubbelohde viscometer at 30° C.

<Glass Transition Temperature: Tg>

The glass transition temperature of the polyimide film was determined from the change in the amount of tensile elongation at a temperature raising rate of 10° C./min on the basis of the tensile measurement with Thermomechanical Analyzer (TMA4000) produced by Bruker AXS K.K.

<Cut Off Wavelength (Transparency)>

Regarding the polyimide film having a thickness of 30 μm, the transmittance of the visible-ultraviolet light within the wavelength range of 200 to 800 nm was measured with Spectrophotometer for ultraviolet and visible region (UV-3100S) produced by SHIMADZU CORPORATION. The wavelength at which the transmittance becomes 0.5% or less (cut off wavelength) was taken as the index of transparency. A shorter cut off wavelength refers to that the transparency of the polyimide film is better.

<Light Transmittance (Transparency)>

Regarding the polyimide film having a film thickness of 30 μm, the transmittance of light of 400 nm was measured with Spectrophotometer for ultraviolet and visible region (UV-3100S) produced by SHIMADZU CORPORATION. A higher transmittance refers to that the transparency of the polyimide film is better.

<Coefficient of Linear Thermal Expansion: CTE>

The coefficient of linear thermal expansion of the polyimide film was determined as an average value within the range of 100° C. to 200° C. from the elongation of a test piece at load 0.5 g/film thickness 1 μm and a temperature raising rate of 10° C./min on the basis of the thermomechanical analysis with Thermomechanical Analyzer (TMA4000) produced by Bruker AXS K.K.

<Water Absorption Coefficient>

After the polyimide film (film thickness 30 μm) was vacuum-dried at 80° C. for 3 hours, the film was immersed in water at 25° C. for 24 hours. The film was sandwiched between dry paper (pulp 100%) having good water absorption property, followed by standing for 1 minute, so as to allow the water adhered to the film surface to soak into the paper. The paper was changed two times so as to repeat the same operation. Thereafter, the weight is measured, and the water absorption coefficient (%) was determined from an increment of the weight.

In the following examples, synthesis of 1,4-bis(4'-oxa-3', 5'-dioxotricyclo[5.2.1.0$^{2,6}$]-decan-8'-ylcarboxy)benzene represented by the following structural formula will be described as an example of production of the tetracarboxylic dianhydride according to the present invention.

[Chemical formula 29]

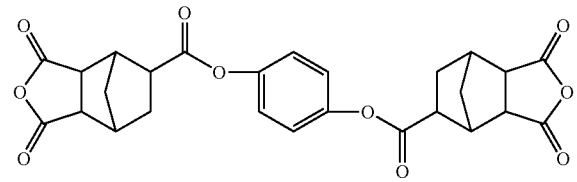

Norbornane-2-exo,3-exo,5-exo-tricarboxylic acid trimethyl ester serving as the raw material in the synthesis of the above-described compound can be synthesized by the method described in Japanese Patent No. 3342938 and the like.

Example 1

An aqueous solution in which 30.0 g (111 mmol) of norbornane-2-exo,3-exo,5-exo-tricarboxylic acid trimethyl ester, 30.0 g of sulfolane, and 10.9 g of sulfuric acid were dissolved in 50.0 g of water was put in a reaction container provided with a nitrogen introduction pipe and a condenser, and heating was conducted at 104° C. for 5 hours in nitrogen atmosphere. In the meantime, 17 g per hour of water was added while distilled methanol and water were removed to the outside of the system. Cooling was conducted after the reaction, 150 g of water was added, and extraction was conducted with toluene (200 ml×4 times). After 70 g of sodium chloride was added to the water layer, extraction was conducted with a mixture solvent (200 mL×2 times, 100 mL×once) of tetrahydrofuran/ethyl acetate (1/1) (volume ratio). The resulting tetrahydrofuran/ethyl acetate layer was washed with a saturated saline solution (100 mL×once). Subsequently, the tetrahydrofuran/ethyl acetate layer was concentrated until the total amount became 57 g, 40 mL of toluene was added, and precipitated crystal was filtrated. The resulting crystal was crude norbornane-2-exo,3-exo,5-exo-tricarboxylic acid and the yield of the crude compound was 19.3 g (76%). This crude compound was blended with 60 mL of tetrahydrofuran and 60 mL of toluene, and was dissolved by heating in a water bath at 80° C., while 26 g of distilled solvent was removed to the outside of the system. Thereafter, standing was conducted at room temperature and precipitated crystal was filtrated, so that 14.2 g (primary crystal) of norbornane-2-exo,3-exo,5-exo-tricarboxylic acid was obtained. The filtrate was further concentrated, so that 4.5 g of crystal (secondary crystal) was obtained (total recovery factor of primary crystal and secondary crystal 98%). This compound was identified as the desired product from $^1$H-NMR thereof. Furthermore, this compound was converted to a trimethyl ester with trimethylsilyldiazomethane and analyzed by gaschromatography. As a result, it was made clear that the purity was 100%.

Example 2

After 20.1 g (87.7 mmol) of norbornane-2-exo,3-exo,5-exo-tricarboxylic acid obtained by a method in Example 1, 32 mg (0.44 mmol; 0.005 molar equivalent relative to tricarboxylic acid) of dimethylformamide, and 100 mL of toluene serving as a solvent were put in a reaction container provided with a nitrogen introduction pipe and a condenser, heating was conducted in such a way that the inner temperature became 70° C. Then, 31.3 g (263 mmol; 3.0 molar equivalent relative to tricarboxylic acid) of thionyl chloride was added thereto, and reflux was conducted for 2 hours in a nitrogen atmosphere. Subsequently, excess thionyl chloride and 81 g of toluene were removed by distillation under reduced pressure. The residual solution was blended with 200 mL of heptane so as to precipitate a crystal. The resulting crystal was filtrated and, thereby, 16.0 g (crude yield 80%) of white crystal of crude 5-exo-chloroformyl-norbornane-2-exo,3-exo-dicarboxylic anhydride was obtained. This crystal was allowed to recrystallize from a mixed solvent of 20 mL of toluene and 20 mL of ethyl acetate and, thereby, 12.5 g (recovery factor 80%) of primary crystal and 1.4 g (recovery factor 9%) of secondary crystal were obtained. The spectrum data of the resulting crystal were as described below. The melting point measured with a melting point measuring apparatus was 130° C.

Figure 2:
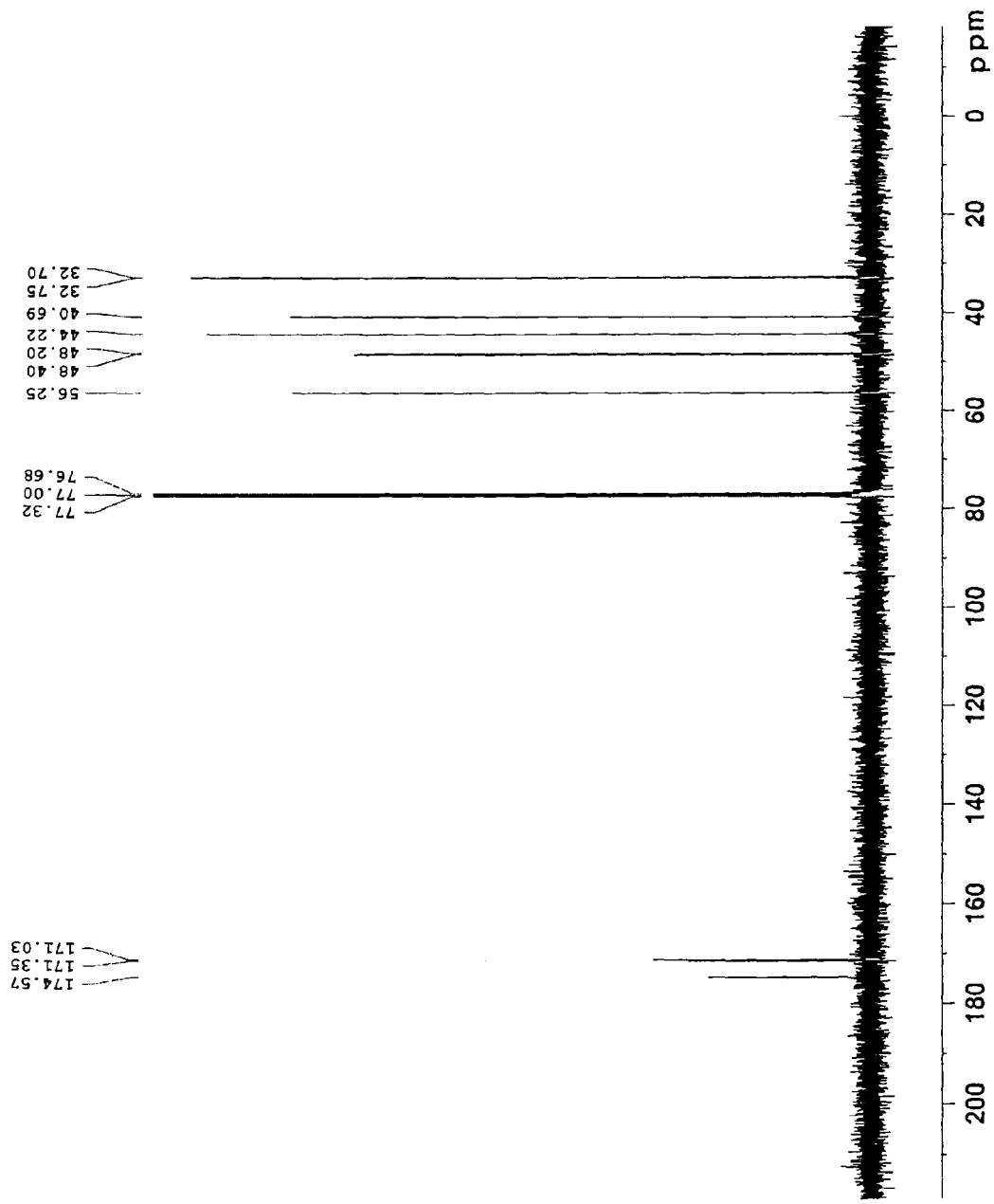
FIG. 2 is a diagram showing a $^{13}$C-NMR spectrum (CDCl$_3$) of 5-exo-chloroformyl-norbornane-2-exo,3-exo-dicarboxylic anhydride produced in Example 2.
Figure 3:
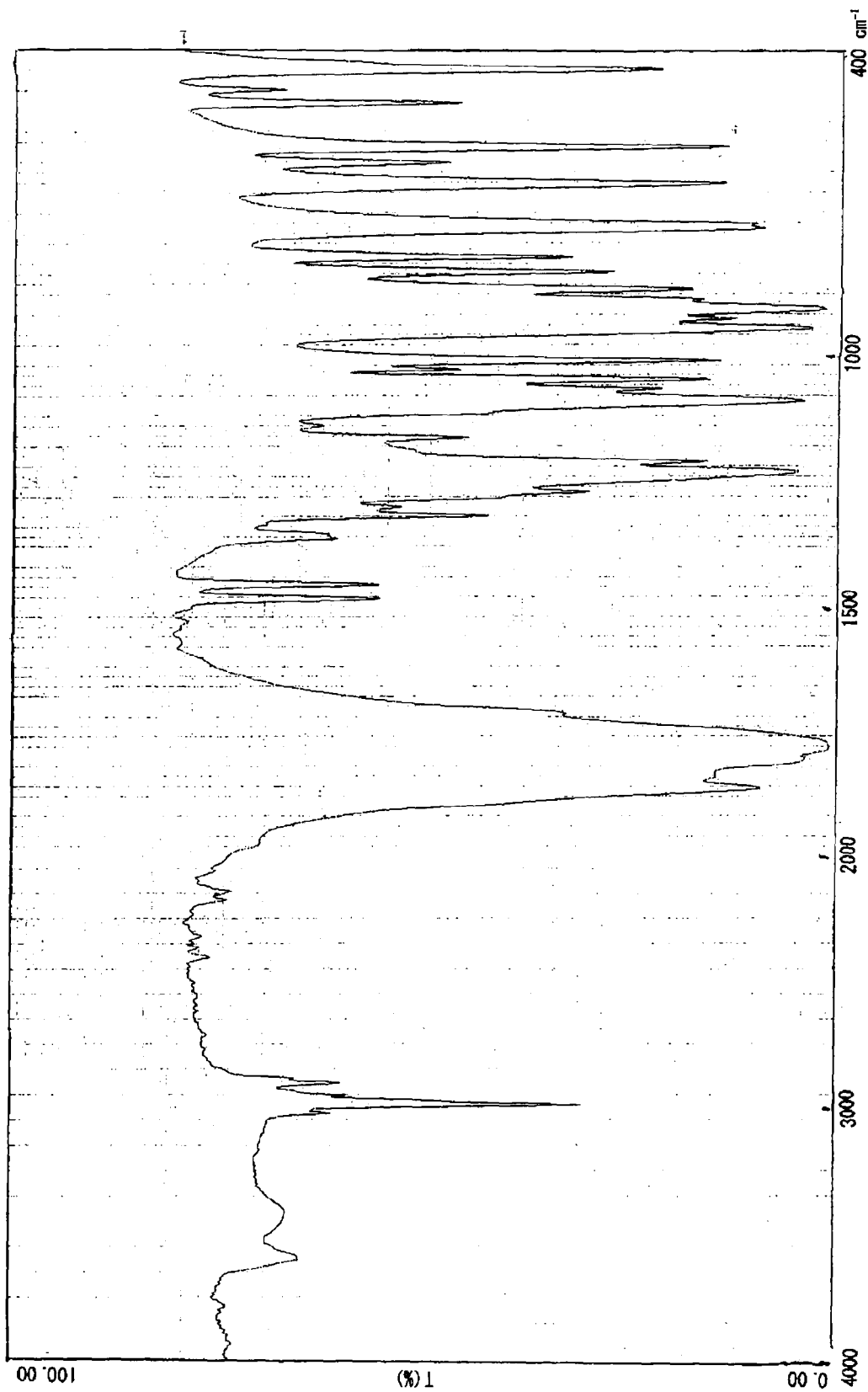
FIG. 3 is a diagram showing an IR spectrum (KBr) of 5-exo-chloroformyl-norbornane-2-exo,3-exo-dicarboxylic anhydride produced in Example 2.
Figure 4:
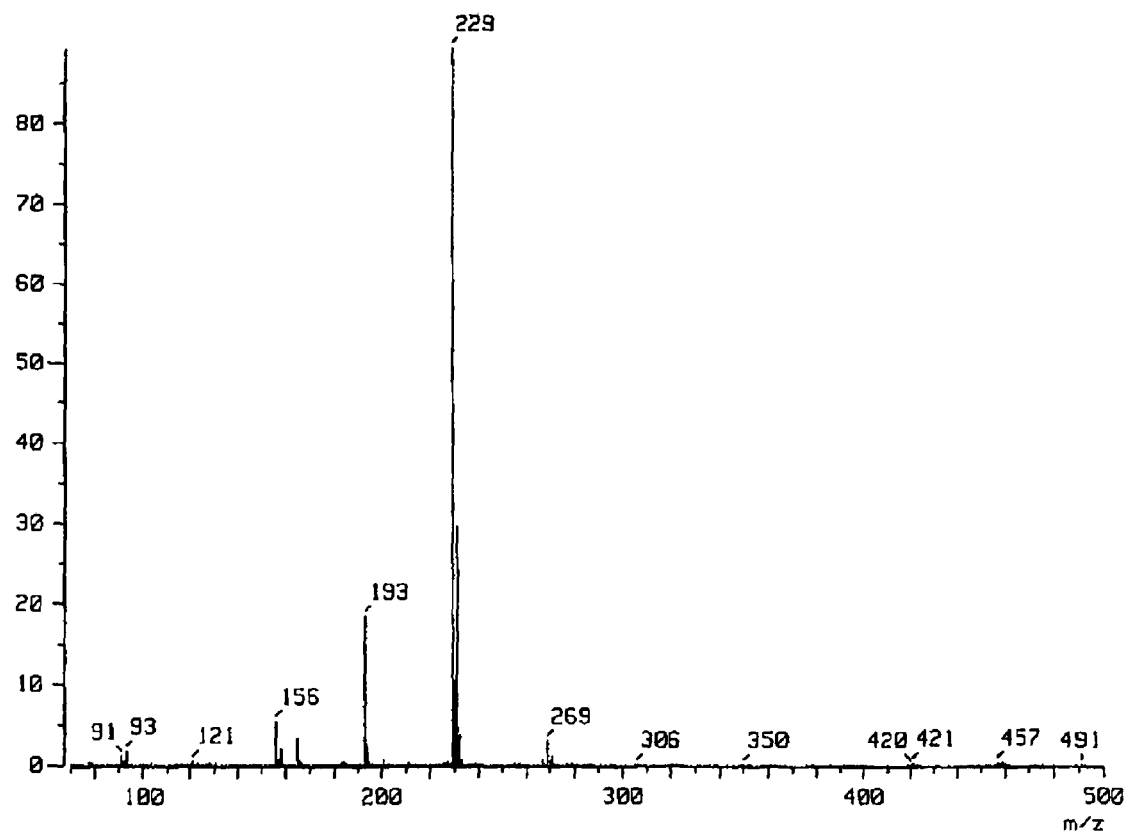
FIG. 4 is a diagram showing a Mass spectrum of 5-exo-chloroformyl-norbornane-2-exo,3-exo-dicarboxylic anhydride produced in Example 2.

$^1$H-NMR spectrum (400 MHz, CDCl$_3$): shown in FIG. 1.
$^{13}$C-NMR spectrum (CDCl$_3$): shown in FIG. 2.
IR spectrum (KBr): shown in FIG. 3
Mass spectrum (CI): shown in FIG. 4

Example 3

In a nitrogen atmosphere, 2.89 g (26.3 mmol) of hydroquinone, 16.6 g of pyridine, and 70 mL of tetrahydrofuran were put in a reaction container so as to dissolve. The resulting mixture was cooled to 2° C. in an ice bath. Thereafter, a solution in which 12.0 g (52.5 mmol; 2.0 molar equivalent relative to hydroquinone) of 5-exo-chloroformyl-norbornane-2-exo,3-exo-dicarboxylic anhydride was dissolved by adding 50 mL of tetrahydrofuran was dropped over 15 minutes with a dropping funnel, and agitation was further conducted for 5 hours so as to obtain a white precipitate. The resulting white precipitate was separated by filtration and was suspended in 150 mL of water, followed by filtration. Furthermore, hydrochloric acid salts were removed completely by washing with water sufficiently. The resulting product was vacuum-dried at 150° C. for 20 hours, so that 11.1 g (recovery factor 85%) of white powder was obtained.

The resulting product was identified as 1,4-bis(4'-oxa-3',5'-dioxotricyclo[5.2.1.0$^{2,6}$]-decan-8'-ylcarboxy)benzene represented by the above-described structural formula from measurements of the following spectra of the product. The melting point measured with a melting point measuring apparatus was 273° C. to 275° C.

Figure 5:
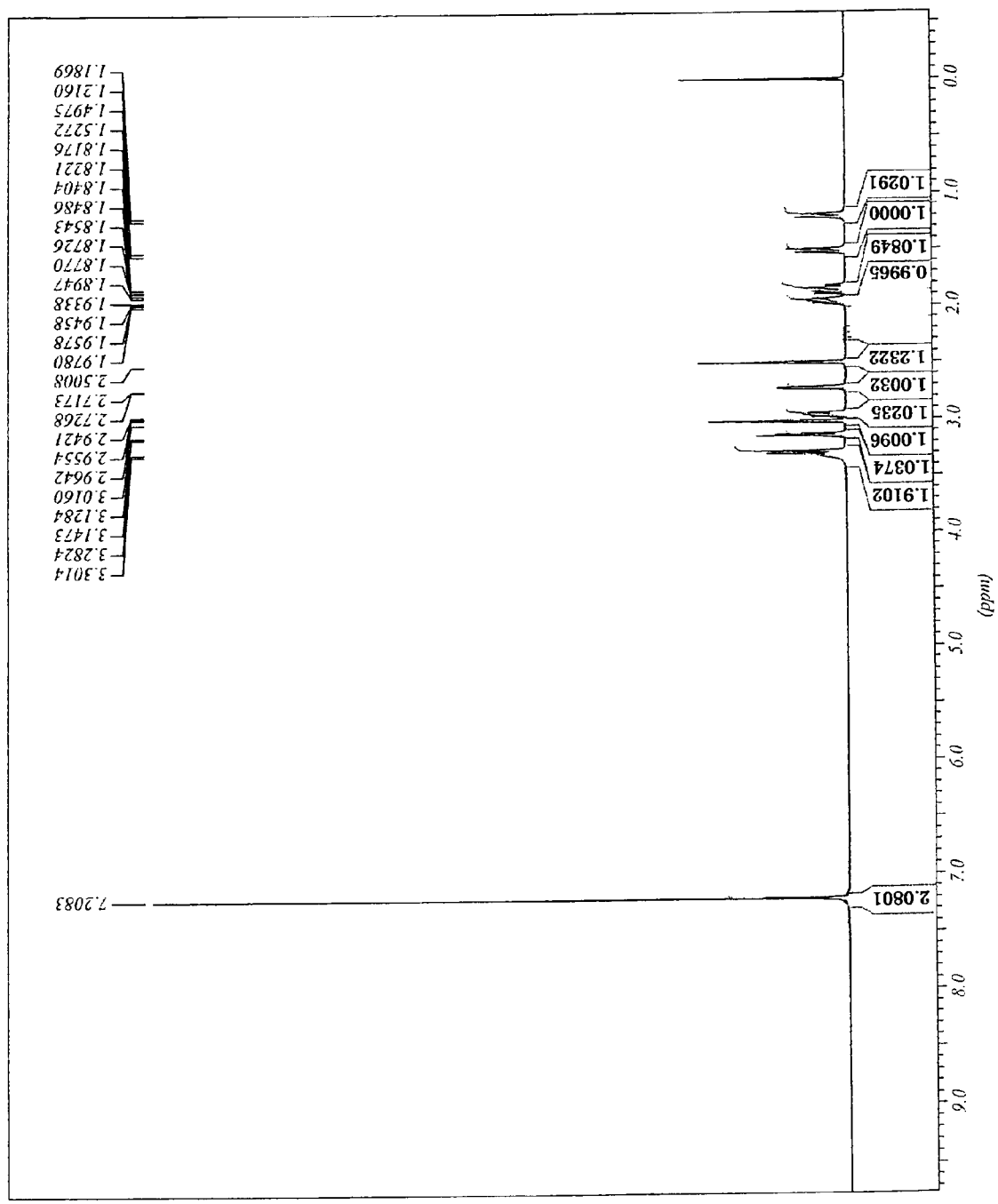
FIG. 5 is a diagram showing a $^1$H-NMR spectrum (DMSO-d$_6$, 400 MHz) of 1,4-bis(4'-oxa-3',5'-dioxotricyclo[5.2.1.0$^{2,6}$]-decan-8'-ylcarboxy)benzene produced in Example 3.
Figure 6:
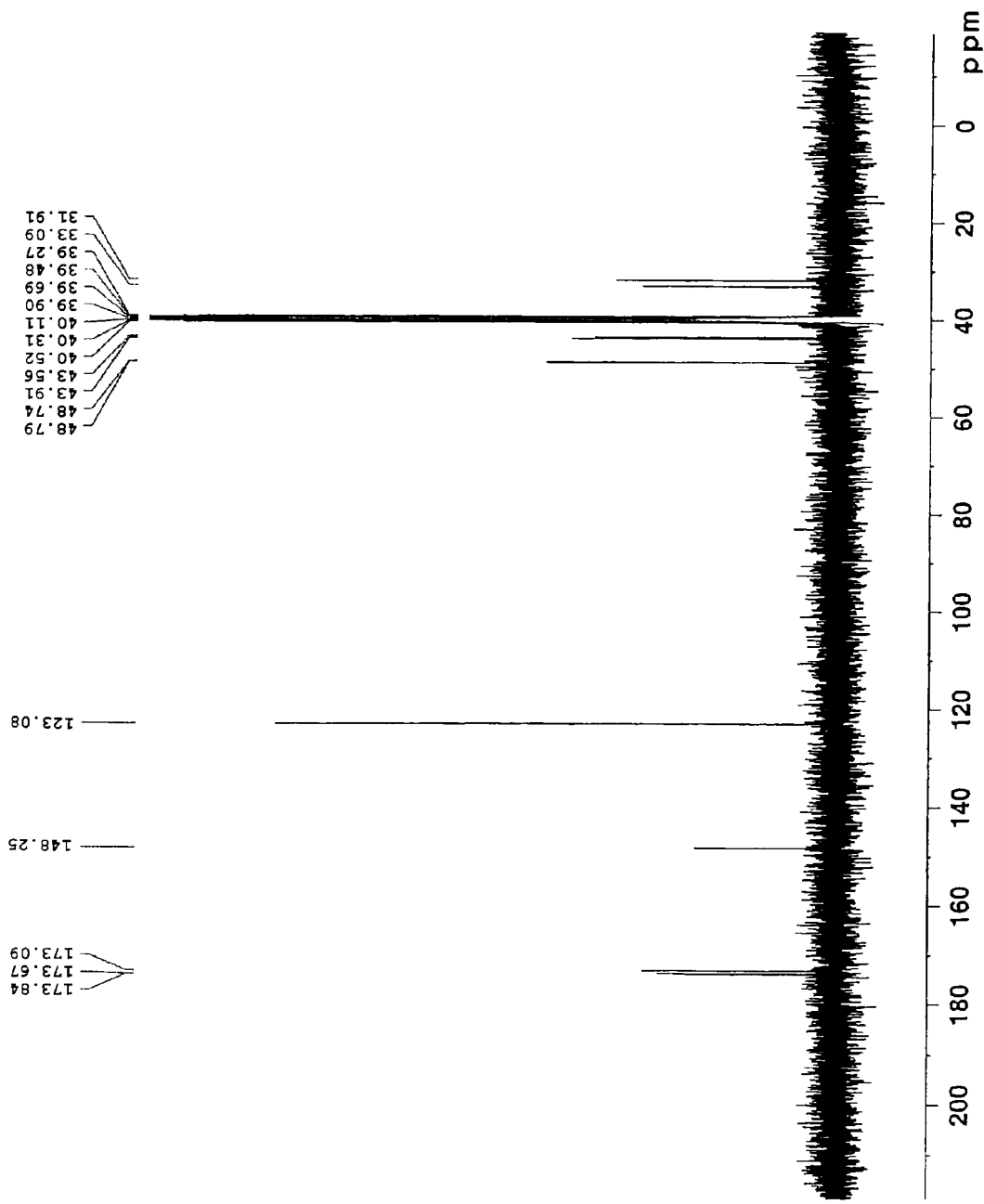
FIG. 6 is a diagram showing a $^{13}$C-NMR spectrum (DMSO-d$_6$) of 1,4-bis(4'-oxa-3',5'-dioxotricyclo[5.2.1.0$^{2,6}$]-decan-8'-ylcarboxy)benzene produced in Example 3.
Figure 7:
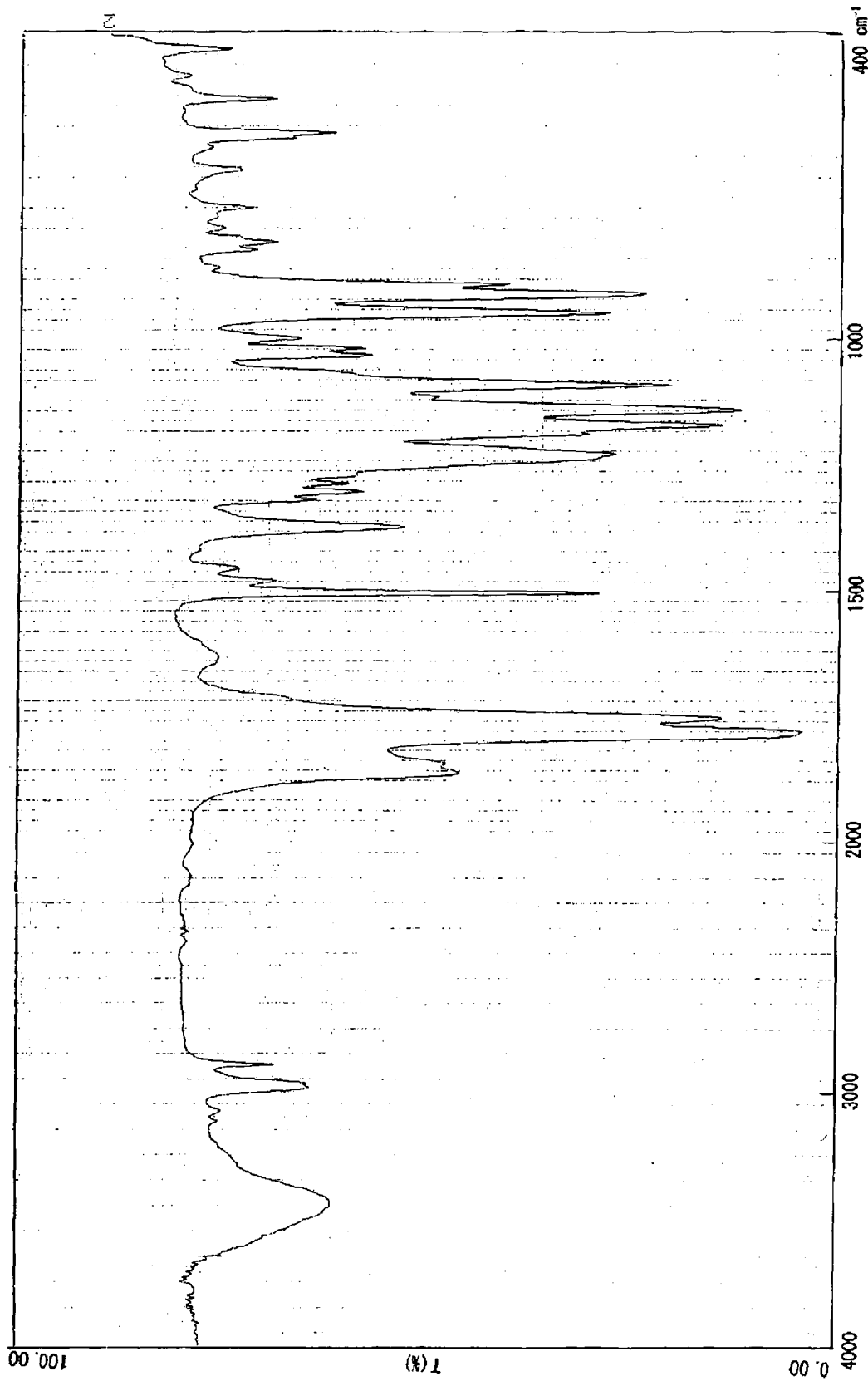
FIG. 7 is a diagram showing an IR spectrum (KBr) of 1,4-bis(4'-oxa-3',5'-dioxotricyclo[5.2.1.0$^{2,6}$]-decan-8'-ylcarboxy)benzene produced in Example 3.
Figure 8:
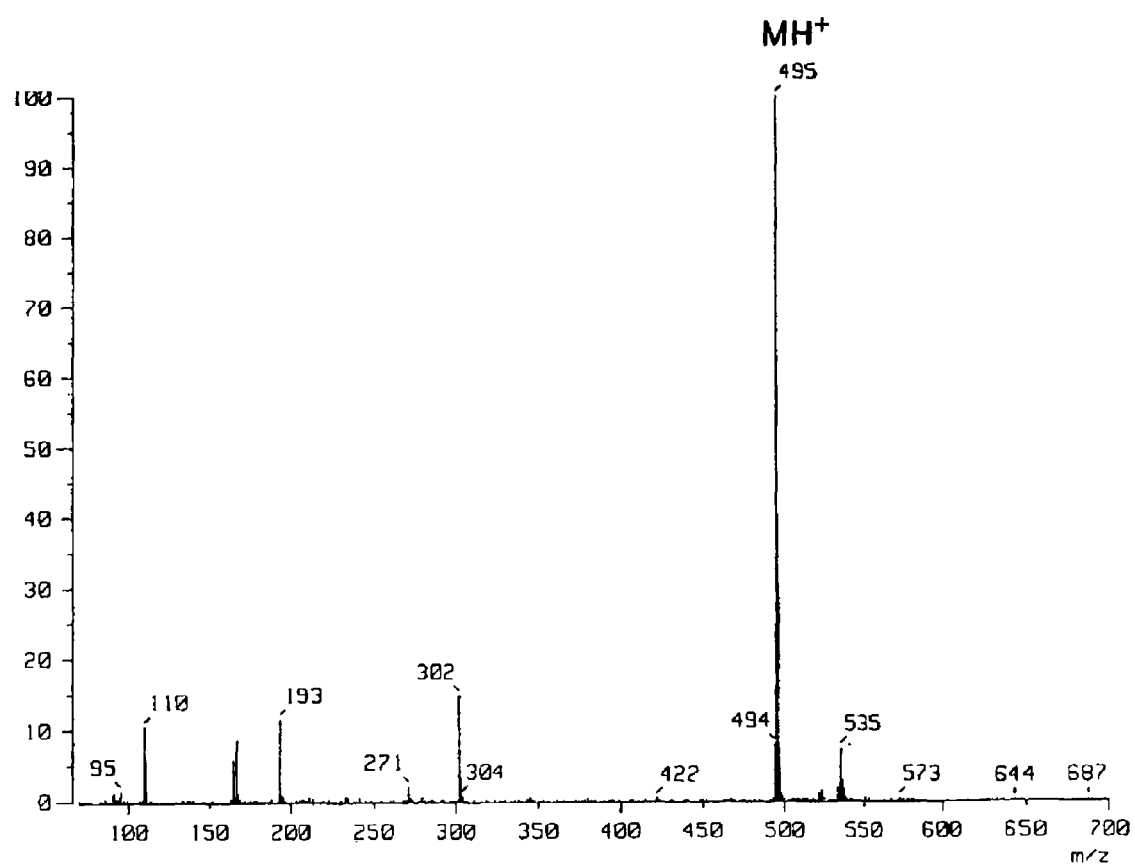
FIG. 8 is a diagram showing a Mass spectrum of 1,4-bis(4'-oxa-3',5'-dioxotricyclo[5.2.1.0$^{2,6}$]-decan-8'-ylcarboxy)benzene produced in Example 3.

$^1$H-NMR spectrum (400 MHz, DMSO): shown in FIG. 5.
$^{13}$C-NMR spectrum (DMSO): shown in FIG. 6.
IR spectrum (KBr): shown in FIG. 7
Mass spectrum (CI): shown in FIG. 8

Production of a polyimide by using 1,4-bis(4'-oxa-3',5'-dioxotricyclo[5.2.1.0$^{2,6}$]-decan-8'-ylcarboxy)benzene obtained in Example 3 and film formation will be described below.

Example 4

Production of a polyimide having a structure described below and film formation were conducted.

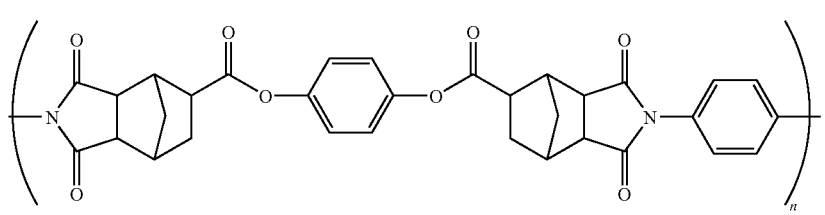

[Chemical formula 30]

In a 50 mL three-necked flask under a nitrogen atmosphere, 0.219 g (2.02 mmol) of p-phenylenediamine was dissolved in 3.85 g of N,N-dimethylacetamide (DMAc), 1.001 g (2.02 mmol) of tetracarboxylic dianhydride powder produced in Example 3 was added to the resulting solution, and agitation was conducted at room temperature. In the meantime, DMAc was added whenever the viscosity of the reaction solution increased so as to adjust the viscosity. The agitation was continued for 6 hours in total, so that a transparent viscous polyimide precursor solution was obtained. The final concentration thereof was 11.9 percent by weight, and the intrinsic viscosity was 1.31 dL/g.

The above-described reaction solution was applied to a glass substrate, and a polyimide film was prepared by a heat-imidization method. The resulting film was dried at 60° C. for 0.5 hours in a nitrogen atmosphere. Thereafter, a heat treatment was conducted under reduced pressure of 0.001 MPa at 80° C. for 1 hour and then at 300° C. for 1 hour. Peeling from the glass substrate was conducted and, thereby, a transparent film having a film thickness of 30 μm was obtained.

Regarding the film properties of the resulting polyimide film, the glass transition temperature was 295° C. (TMA measurement value) and, therefore, relatively high heat resistance was exhibited. The transmittance of light of 400 nm was 85.4% where the cut off wavelength was 283 nm and, therefore, very high transparency was exhibited. Furthermore, the coefficient of linear thermal expansion (CTE) of the polyimide film was 45.3 ppm/K at 100° C. to 200° C., and the water absorption coefficient was 0.5%. This film was not cracked even when 180 degree bending was conducted.

Figure 9:
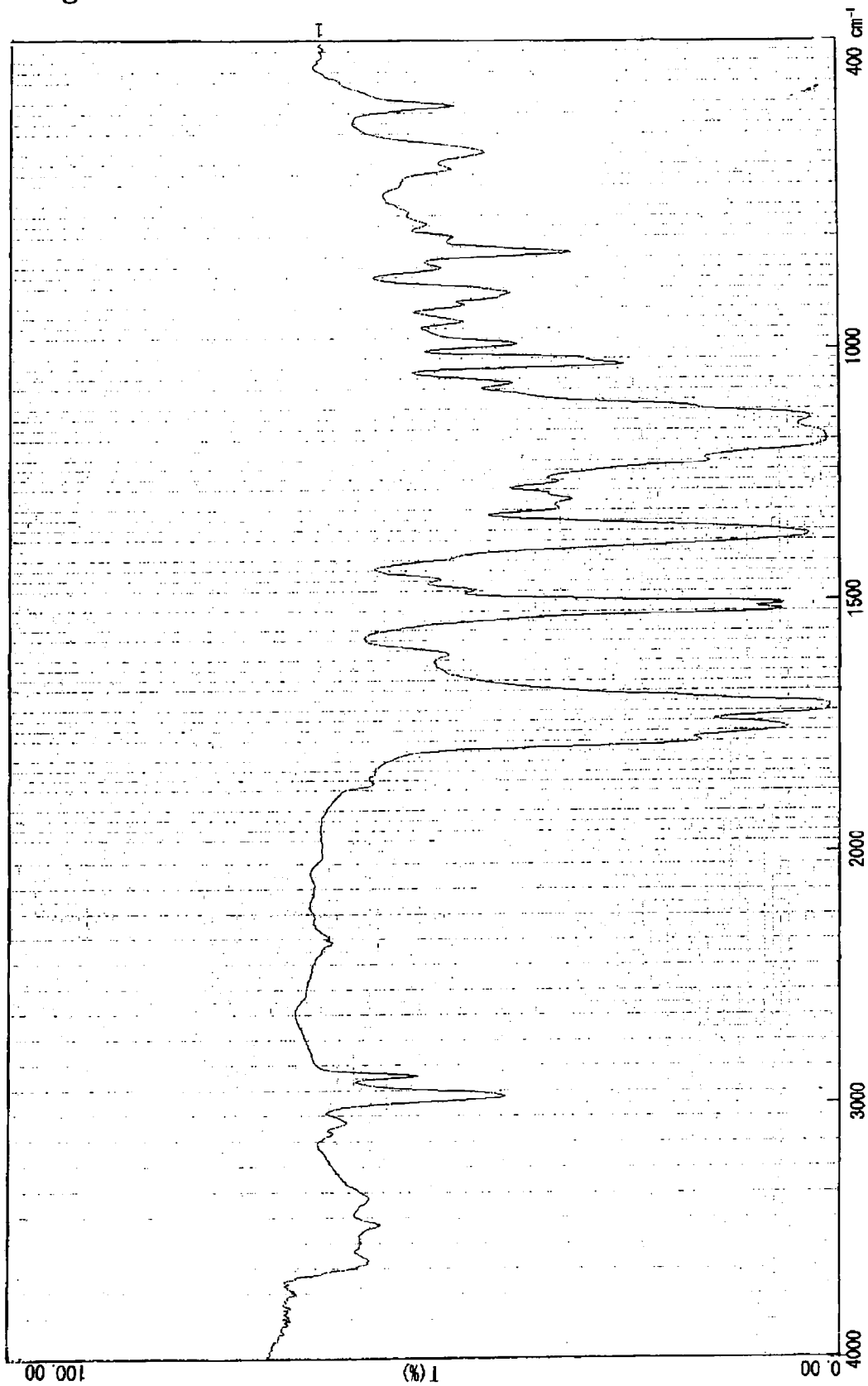
FIG. 9 is a diagram showing an IR spectrum of a polyimide film produced in Example 4.
Figure 10:
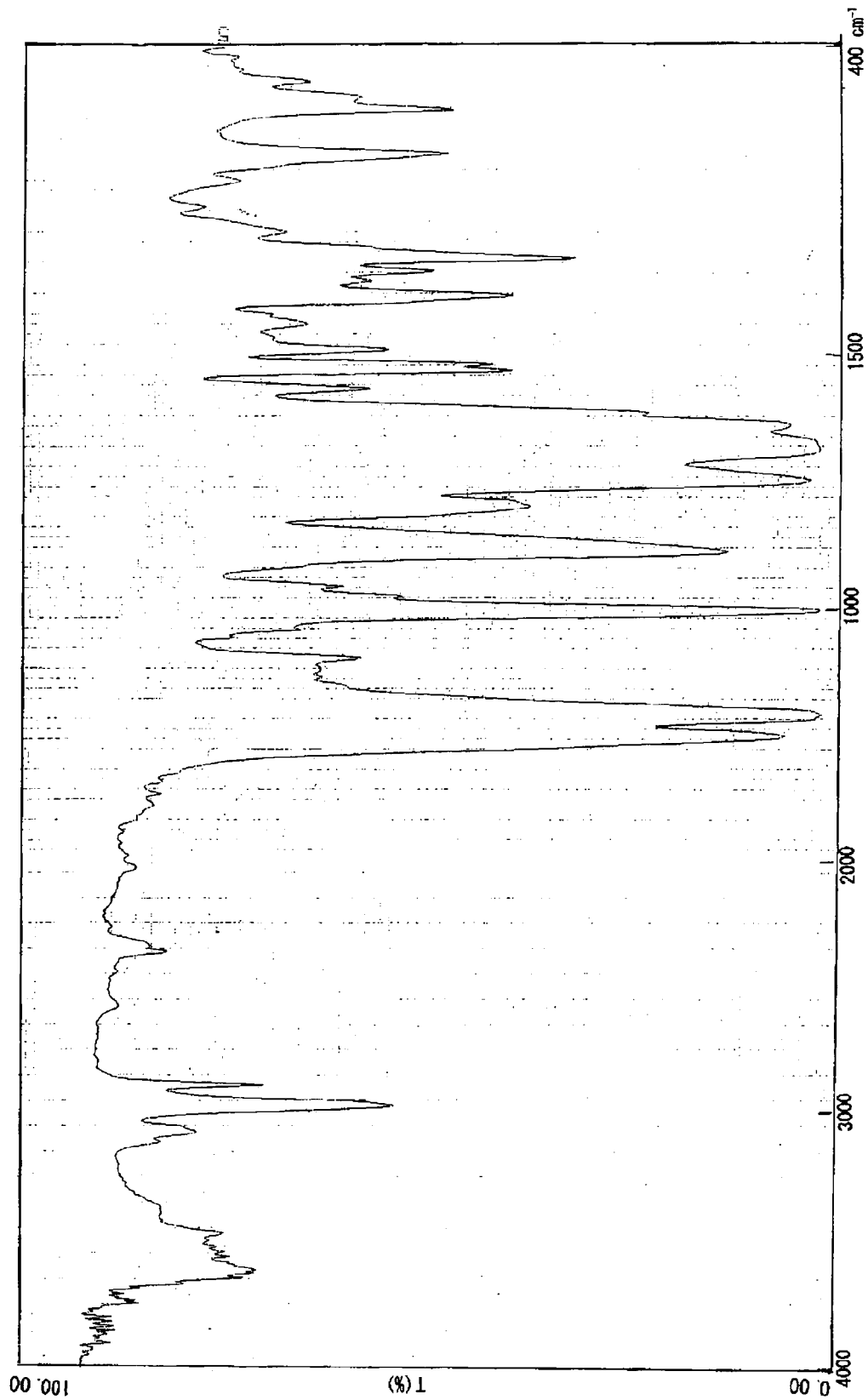
FIG. 10 is a diagram showing an IR spectrum of a polyimide film produced in Example 5.

The IR spectrum of the resulting polyimide thin film is shown in FIG. 9.

Example 5

Production of a polyimide having a structure described below and film formation were conducted.

[Chemical formula 31]

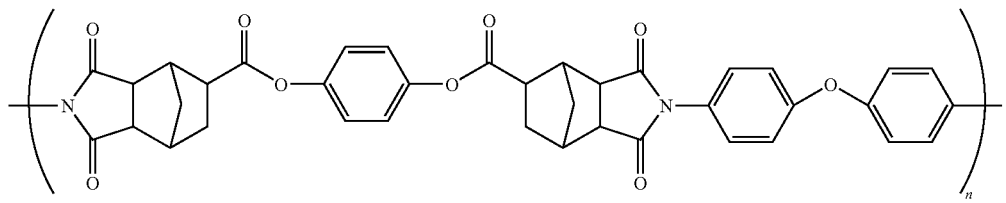

In a 50 mL three-necked flask under a nitrogen atmosphere, 0.304 g (1.52 mmol) of 4,4'-oxydianiline was dissolved in 3.11 g of N,N-dimethylacetamide (DMAc), 0.750 g mmol) of tetracarboxylic dianhydride powder produced in Example 3 was added to the resulting solution, and agitation was conducted at room temperature. In the meantime, DMAC was added whenever the viscosity of the reaction solution increased so as to adjust the viscosity. The agitation was continued for 4 hours in total, so that a transparent viscous polyimide precursor solution was obtained. The final concentration thereof was 14.8 percent by weight, and the intrinsic viscosity was 1.13 dL/g.

Subsequently, 11.72 g of DMAc, 0.77 g of pyridine, and 1.59 g of acetic anhydride were added, and agitation was conducted at room temperature for 1 hour. The contents were added to 180 ml of methanol, and precipitated solids were filtrated. Thereafter, washing was conducted with methanol, and vacuum-drying was conducted at 40° C. for 1 hour, so that 0.86 g of white powder was obtained.

A solution (about 20 percent by weight) in which the resulting powder was dissolved in DMAc was applied to a glass substrate, and drying was conducted at 60° C. for 0.5 hours in a nitrogen atmosphere. Thereafter, a heat treatment was conducted under reduced pressure of 0.001 MPa at 80° C. for 1 hour. The heat-treated coating film was peeled from the glass substrate. A heat treatment was conducted under reduced pressure of 0.001 MPa at 300° C. for 1 hour while both ends were fixed to a metal plate and, thereby, a transparent film having a film thickness of 30 μm was obtained.

Regarding the film properties of the resulting polyimide film, the glass transition temperature was 266° C. (TMA measurement value) and, therefore, relatively high heat resistance was exhibited. The transmittance of light of 400 nm was 85.8% where the cut off wavelength was 299 nm and, therefore, very high transparency was exhibited. Furthermore, the coefficient of linear thermal expansion (CTE) of the polyimide film was 58.9 ppm/K at 100° C. to 200° C. This film was not cracked even when 180 degree bending was conducted.

The present invention has been described in detail with reference to the specific forms. However, it is apparent to one skilled in the art that various modifications thereof could be made without departing from the spirit or scope of the invention.

The present invention contains subject matter related to Japanese Patent Application No. 2005-330427 filed in the Japanese Patent Office on Nov. 15, 2005, Japanese Patent Application No. 2006-046955 filed in the Japanese Patent Office on Feb. 23, 2006, Japanese Patent Application No. 2006-091426 filed in the Japanese Patent Office on Mar. 29, 2006, and Japanese Patent Application No. 2006-186825 filed in the Japanese Patent Office on Jul. 6, 2006, the entire contents of which are incorporated herein by reference.

The invention claimed is:

1. A tetracarboxylic acid compound represented by the following formula (1) or (2)

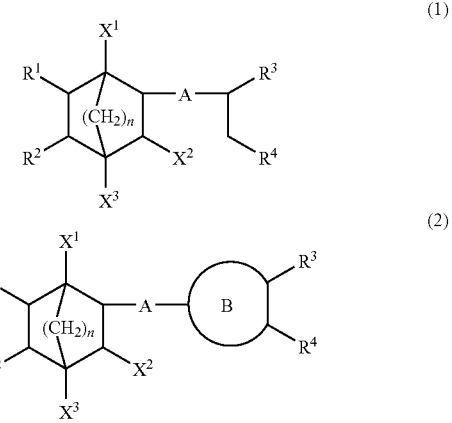

wherein the formulae (1) and (2), A represents a divalent group;

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group, these groups may optionally further have substituents, and the carbon number of the carbon-containing group is 10 or less;

$R^1$, $R^2$, $R^3$, and $R^4$ represent independently a carboxyl group (—C(O)OH), or $R^1$ and $R^2$ represent an acid anhydride group (—C(O)OC(O)—) formed therefrom and/or $R^3$ and $R^4$ represent an acid anhydride group (—C(O)OC(O)—) formed therefrom;

n represents an integer of 1 or 2;

wherein the formula (2), a ring B represents a substituted or unsubstituted $C_3$-$C_{20}$ cyclic group.

2. The tetracarboxylic acid compound according to claim 1, wherein the compound represented by formula (2) is represented by the following formula (2A), (2B), or (2C);

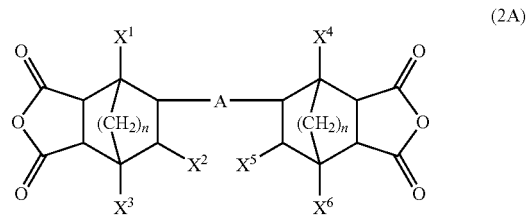

-continued (2B)

$$\text{(structure 2B: bicyclic with X}^1\text{, X}^2\text{, X}^3\text{, X}^4\text{, X}^5\text{, X}^6\text{, (CH}_2)_n\text{, linked by A, one side anhydride, other side two COOH)}$$

(2C)

$$\text{(structure 2C: two rings with X}^1\text{–X}^6\text{, (CH}_2)_n\text{, linked by A, all four substituents COOH)}$$

wherein the formulae (2A), (2B), and (2C), each of A, $X^1$, $X^2$, $X^3$, and n represents the same as that in the formula (2);

$X^4$, $X^5$, and $X^6$ represent independently a hydrogen atom, a halogen atom, a nitrile group, a nitro group, an alkyl group, an alkenyl group, an alkynyl group, an alkoxy group, an amino group, or an amide group, these groups may further have substituents, and the carbon number of the carbon-containing group is 10 or less;

m represents an integer of 1 or 2.

3. The tetracarboxylic acid compound according to claim 2, wherein A in formulae (2A), (2B), and (2C) is represented by the following formula (3)

$$-\overset{O}{\underset{\|}{C}}-D-\overset{O}{\underset{\|}{C}}- \tag{3}$$

wherein the formula (3), D represents a divalent group.

4. The tetracarboxylic acid compound according to claim 3, wherein A in formulae (2A), (2B), and (2C) is represented by the following formula (3A) or (3B)

$$-\overset{O}{\underset{\|}{C}}-O-D^1-O-\overset{O}{\underset{\|}{C}}- \tag{3A}$$

$$-\overset{O}{\underset{\|}{C}}-\overset{H}{\underset{|}{N}}-D^2-\overset{H}{\underset{|}{N}}-\overset{O}{\underset{\|}{C}}- \tag{3B}$$

wherein the formulae (3A) and (3B), $D^1$ and $D^2$ represent a divalent group.

5. The tetracarboxylic acid compound according to claim 2, wherein $X^1$, $X^2$, $X^3$, $X^4$, $X^5$, and $X^6$ in formulae (2A), (2B), and (2C) represent a hydrogen atom, and A represents a divalent group including at least one cyclic structure.

6. An acid halide represented by the following formula (4)

(4)

$$\text{(structure 4: cyclic with X}^1\text{, X}^2\text{, X}^3\text{, R}^1\text{, R}^2\text{, (CH}_2)_n\text{, and C(O)X group)}$$

wherein the formula (4), $X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group, these groups may further have substituents, and the carbon number of the carbon-containing group is 10 or less;

$R^1$ and $R^2$ represent independently a carboxyl group (—C(O)OH) or $R^1$ and $R^2$ represent an acid anhydride group (—C(O)OC(O)—) formed therefrom;

n represents an integer of 1 or 2; and

X represents a chlorine atom or a bromine atom.

7. A method for producing the tetracarboxylic acid compound according to any one of claims 1 to 5, comprising:

reacting an acid halide represented by the following formula (4)

(4)

$$\text{(structure 4 repeated)}$$

wherein the formula (4), $X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group, these groups may further have substituents, and the carbon number of the carbon-containing group is 10 or less;

$R^1$ and $R^2$ represent independently a carboxyl group (—C(O)OH) or $R^1$ and $R^2$ represent an acid anhydride group (—C(O)OC(O)—) formed therefrom;

n represents an integer of 1 or 2; and

X represents a chlorine atom or a bromine atom, with a divalent alcohol or amine or a monovalent alcohol or amine, which has a carboxylic anhydride group.

8. A polyimide precursor comprising a structural unit represented by the following formula (5) as at least a part thereof (5)

$$\text{(polymer structural unit with HN, R}^{11}\text{O, (CH}_2)_n\text{, X}^1\text{, X}^2\text{, X}^3\text{, linked through O-D}^1\text{-O to B group with NH-Q and OR}^{12}\text{)}$$

wherein the formula (5), $D^1$ represents a divalent group;

ring B represents a substituted or unsubstituted $C_3$-$C_{20}$ cyclic group;

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group;

Q represents a divalent aromatic group or a divalent aliphatic group;

$R^{11}$ and $R^{12}$ represent independently a hydrogen atom or an alkyl group or a silyl group, which has the carbon number of 1 to 10; and n represents an integer of 1 or 2.

9. A polyimide precursor comprising a structural unit represented by the following formula (6) as at least a part thereof;

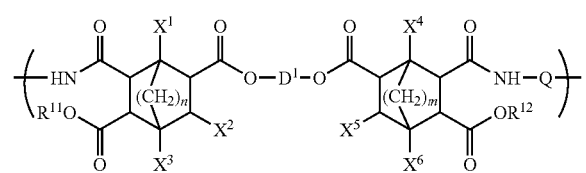
(6)

wherein the formula (6), $D^1$ represents a divalent group;

$X^1$, $X^2$, $X^3$, $X^4$, $X^5$, $X^6$ represent independently a hydrogen atom, a halogen atom, a nitrile group, a nitro group, an alkyl group, an alkenyl group, an alkynyl group, an alkoxy group, an amino group, or an amide group;

Q represents a divalent aromatic group or a divalent aliphatic group;

$R^{11}$ and $R^{12}$ represent independently a hydrogen atom or an alkyl group or a silyl group, which has the carbon number of 1 to 10; and n and m represent independently an integer of 1 or 2.

10. A polyimide comprising a structural unit represented by the following formula (7) as at least a part thereof;

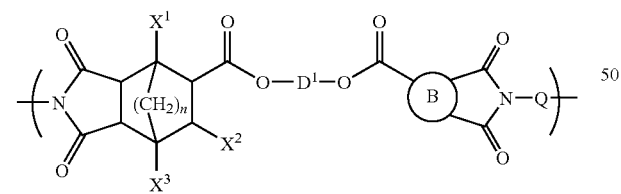
(7)

wherein the formula (7), $D^1$ represents a divalent group;

B represents a substituted or unsubstituted $C_3$-$C_{20}$ cyclic group;

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group;

Q represents a divalent aromatic group or a divalent aliphatic group; and n represents an integer of 1 or 2.

11. A polyimide comprising a structural unit represented by the following formula (8) as at least a part thereof

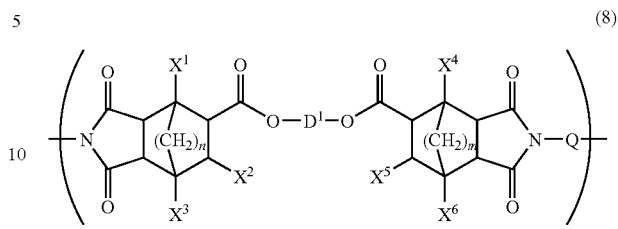
(8)

wherein the formula (8), $D^1$ represents a divalent group;

$X^1$, $X^2$, $X^3$, $X^4$, $X^5$, and $X^6$ represent independently a hydrogen atom, a halogen atom, a nitrile group, a nitro group, an alkyl group, an alkenyl group, an alkynyl group, an alkoxy group, an amino group, or an amide group;

Q represents a divalent aromatic group or a divalent aliphatic group; and n and m represent independently an integer of 1 or 2.

12. A method for producing the polyimide according to claim 10, comprising reacting the tetracarboxylic acid compound represented by the following formula (1) or (2)

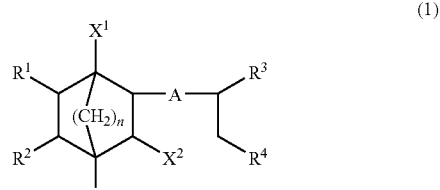
(1)

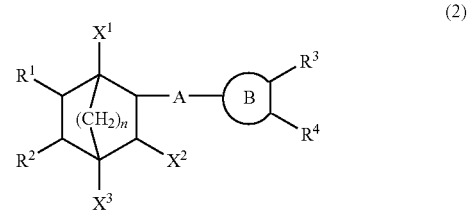
(2)

wherein A represents a divalent group;

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group;

$R^1$, $R^2$, $R^3$, and $R^4$ represent independently a carboxyl group (—C(O)OH), or $R^1$ and $R^2$ represent an acid anhydride group (—C(O)OC(O)—) formed therefrom and/or $R^3$ and $R^4$ represent an acid anhydride group (—C(O)OC(O)—) formed therefrom;

n represents an integer of 1 or 2;

wherein B represents a substituted or unsubstituted $C_3$-$C_{20}$ cyclic group which may have a substituent with one or more diamines and, thereafter, conducting a cyclization and imidization reaction.

13. A method for producing the polyimide according to claim 11, comprising:

reacting a tetracarboxylic acid compound represented by the following formula (1) or (2)

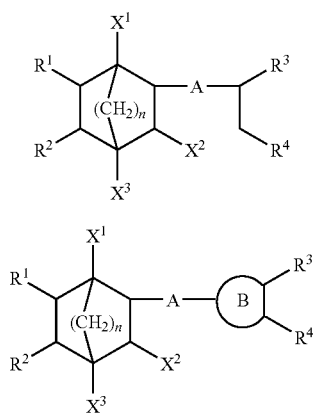

(1)

(2)

wherein A represents a divalent group;

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group;

$R^1$, $R^2$, $R^3$, and $R^4$ represent independently a carboxyl group (—C(O)OH), or $R^1$ and $R^2$ represent an acid anhydride group (—C(O)OC(O)—) formed therefrom and/or $R^3$ and $R^4$ represent an acid anhydride group (—C(O)OC(O)—) formed therefrom;

n represents an integer of 1 or 2;

wherein the formula (2), a ring B represents a substituted or unsubstituted $C_3$-$C_{20}$ cyclic group which may have a substituent with one or more diamines and, thereafter, conducting a cyclization and imidization reaction.

14. A method for producing the polyimide according to claim 10, comprising:

subjecting a polyimide precursor comprising a structural unit represented by the following formula (5)

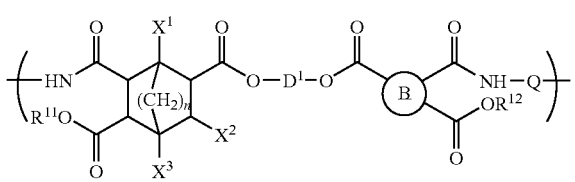

(5)

wherein $D^1$ represents a divalent group;

ring B represents a substituted or unsubstituted $C_3$-$C_{20}$ cyclic group;

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group;

Q represents a divalent aromatic group or a divalent aliphatic group;

$R^{11}$ and $R^{12}$ represent independently a hydrogen atom or an alkyl group or a silyl group, which has the carbon number of 1 to 10; and n represents an integer of 1 or 2, to a cyclization and imidization reaction.

15. A method for producing the polyimide according to claim 11, comprising:

subjecting a polyimide precursor comprising a structural unit represented by the following formula (5)

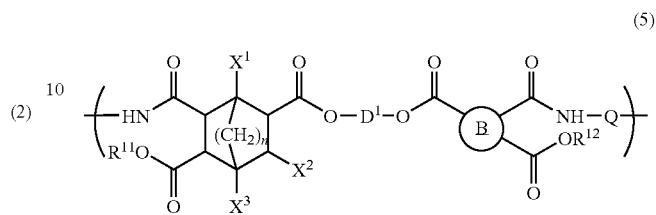

(5)

wherein $D^1$ represents a divalent group;

ring B represents a substituted or unsubstituted $C_3$-$C_{20}$ cyclic group;

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group;

Q represents a divalent aromatic group or a divalent aliphatic group;

$R^{11}$ and $R^{12}$ represent independently a hydrogen atom or an alkyl group or a silyl group, which has the carbon number of 1 to 10; and n represents an integer of 1 or 2, to a cyclization and imidization reaction.

16. A method for producing the polyimide according to claim 10, comprising:

subjecting the polyimide precursor comprising a structural unit represented by the following formula (6);

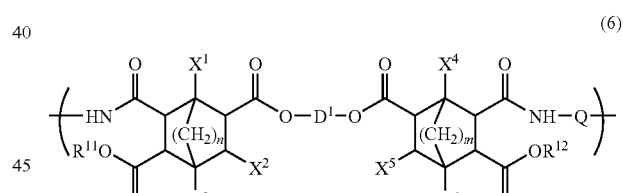

(6)

wherein $D^1$ represents a divalent group;

$X^1$, $X^2$, $X^3$, $X^4$, $X^5$, and $X^6$ represent independently a hydrogen atom, a halogen atom, a nitrile group, a nitro group, an alkyl group, an alkenyl group, an alkynyl group, an alkoxy group, an amino group, or an amide group;

Q represents a divalent aromatic group or a divalent aliphatic group;

$R^{11}$ and $R^{12}$ represent independently a hydrogen atom or an alkyl group or a silyl group, which has the carbon number of 1 to 10; and n and m represent independently an integer of 1 or 2; to a cyclization and imidization reaction.

17. A method for producing the polyimide according to claim 11, comprising:

subjecting the polyimide precursor comprising a structural unit represented by the following formula (6);

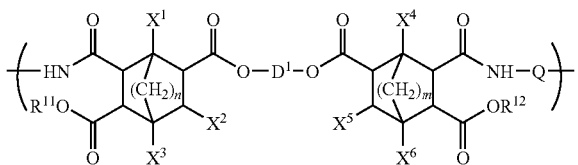

(6)

wherein $D^1$ represents a divalent group;

$X^1$, $X^2$, $X^3$, $X^4$, $X^5$, and $X^6$ represent independently a hydrogen atom, a halogen atom, a nitrile group, a nitro group, an alkyl group, an alkenyl group, an alkynyl group, an alkoxy group, an amino group, or an amide group;

Q represents a divalent aromatic group or a divalent aliphatic group;

$R^{11}$ and $R^{12}$ represent independently a hydrogen atom or an alkyl group or a silyl group, which has the carbon number of 1 to 10; and n and m represent independently an integer of 1 or 2, to a cyclization and imidization reaction.

18. The method for producing the polyimide according to claim 12, wherein the cyclization and imidization reaction is conducted by at least one of heating and a dehydration reagent.

19. A method for producing the polyimide according to claim 13, wherein the cyclization and imidization reaction is conducted by at least one of heating and a dehydration reagent.

20. A method for producing the polyimide according to claim 14, wherein the cyclization and imidization reaction is conducted by at least one of heating and a dehydration reagent.

21. A method for producing the polyimide according to claim 15, wherein the cyclization and imidization reaction is conducted by at least one of heating and a dehydration reagent.

22. A method for producing the polyimide according to claim 16, wherein the cyclization and imidization reaction is conducted by at least one of heating and a dehydration reagent.

23. A method for producing the polyimide according to claim 17, wherein the cyclization and imidization reaction is conducted by at least one of heating and a dehydration reagent.

24. A film produced from a resin comprising a structural unit represented by the following formula (7) as at least a part thereof

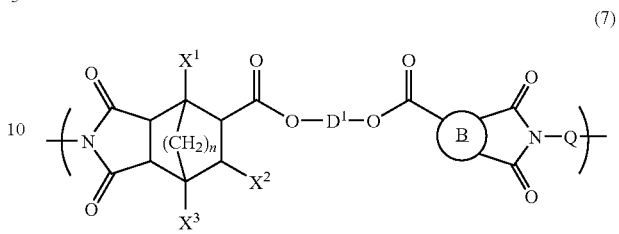

(7)

wherein the formula (7), $D^1$ represents a divalent group;

ring B represents a substituted or unsubstituted $C_3$-$C_{20}$ cyclic group;

$X^1$, $X^2$, and $X^3$ represent independently a hydrogen atom, a halogen atom, a nitrile group, a nitro group, an alkyl group, an alkenyl group, an alkynyl group, an alkoxy group, an amino group, or an amide group;

Q represents a divalent aromatic group or a divalent aliphatic group; and n represents an integer of 1 or 2.

25. The tetracarboxylic acid compound of claim 1, wherein the group A has the following chemical formula:

(3)

wherein D represents a divalent group.

26. The tetracarboxylic acid compound according to claim 1, wherein the group A is —(C═O)—O—$C_6H_4$—O—(C═O)—.

27. The tetracarboxylic acid compound according to claim 1, wherein B is a $C_3$-$C_{20}$ cyclic group selected from the group consisting of a benzene ring, a naphthalene ring, a cyclohexane ring, a cyclopentane ring, a norbornane ring, a bicyclo[2.2.1]heptane ring and a bicyclo[2.2.2]octane ring.

28. The tetracarboxylic acid compound according to claim 1, wherein the ring B represents a substituted or unsubstituted $C_3$-$C_{10}$ cyclic group.

* * * * *